US009763995B2

(12) United States Patent
Wang et al.

(10) Patent No.: US 9,763,995 B2
(45) Date of Patent: Sep. 19, 2017

(54) POLYMER CONJUGATES OF PROTEGRIN PEPTIDES

(71) Applicant: Nektar Therapeutics, San Francisco, CA (US)

(72) Inventors: Yujun Wang, Fremont, CA (US); Haim Moskowitz, San Diego, CA (US); Xiaofeng Liu, Belmont, CA (US); Steven O. Roczniak, Greensboro, NC (US); Mary J. Bossard, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/821,138

(22) Filed: Aug. 7, 2015

(65) Prior Publication Data

US 2016/0158311 A1 Jun. 9, 2016

Related U.S. Application Data

(63) Continuation of application No. 13/119,216, filed as application No. PCT/US2009/005210 on Sep. 17, 2009, now abandoned.

(60) Provisional application No. 61/192,586, filed on Sep. 19, 2008.

(51) Int. Cl.

| | |
|---|---|
| *A61K 38/00* | (2006.01) |
| *A61K 38/10* | (2006.01) |
| *A61K 47/48* | (2006.01) |
| *C07K 7/08* | (2006.01) |

(52) U.S. Cl.

CPC ........ *A61K 38/10* (2013.01); *A61K 47/48023* (2013.01); *A61K 47/48215* (2013.01); *C07K 7/08* (2013.01)

(58) Field of Classification Search

None

See application file for complete search history.

(56) References Cited

U.S. PATENT DOCUMENTS

| | | | | |
|---|---|---|---|---|
| 5,252,714 | A | 10/1993 | Harris et al. | |
| 5,612,460 | A | 3/1997 | Zalipsky | |
| 5,629,384 | A | 5/1997 | Veronese et al. | |
| 5,650,234 | A | 7/1997 | Dolence et al. | |
| 5,672,662 | A | 9/1997 | Harris et al. | |
| 5,708,145 | A | 1/1998 | Lehrer et al. | |
| 5,739,208 | A | 4/1998 | Harris | |
| 5,804,558 | A | 9/1998 | Lehrer et al. | |
| 5,840,900 | A | 11/1998 | Greenwald et al. | |
| 5,880,131 | A | 3/1999 | Greenwald et al. | |
| 5,932,462 | A | 8/1999 | Harris et al. | |
| 5,990,237 | A | 11/1999 | Bentley et al. | |
| 6,214,966 | B1 | 4/2001 | Harris | |
| 6,294,199 | B1 * | 9/2001 | Conley ................ | A61K 9/2013 424/400 |
| 6,348,558 | B1 | 2/2002 | Harris et al. | |
| 6,362,254 | B2 | 3/2002 | Harris et al. | |
| 6,376,470 | B1 | 4/2002 | Greenwald et al. | |
| 6,376,604 | B2 | 4/2002 | Kozlowski | |
| 6,413,507 | B1 | 7/2002 | Bentley et al. | |
| 6,448,369 | B1 | 9/2002 | Bentley et al. | |
| 6,495,659 | B2 | 12/2002 | Bentley et al. | |
| 6,602,498 | B2 | 8/2003 | Shen | |
| 6,653,442 | B1 | 11/2003 | Chang et al. | |
| 7,026,440 | B2 | 4/2006 | Bentley et al. | |
| 8,252,275 | B2 | 8/2012 | Bentley et al. | |
| 2002/0065397 | A1 | 5/2002 | Roberts et al. | |
| 2005/0009988 | A1 | 1/2005 | Harris et al. | |
| 2005/0014903 | A1 | 1/2005 | Kozlowski et al. | |
| 2005/0031576 | A1 * | 2/2005 | McManus ........ | A61K 47/48215 424/78.27 |
| 2006/0239960 | A1 | 10/2006 | Bossard et al. | |
| 2006/0293499 | A1 | 12/2006 | Bentley et al. | |
| 2007/0071764 | A1 | 3/2007 | Sullivan et al. | |
| 2011/0166063 | A1 | 7/2011 | Bossard et al. | |
| 2011/0171161 | A1 | 7/2011 | Wang et al. | |
| 2016/0022828 | A1 | 1/2016 | Bossard et al. | |

FOREIGN PATENT DOCUMENTS

| | | | |
|---|---|---|---|
| EP | 0 400 472 | | 12/1990 |
| EP | 1 797 901 | A1 | 6/2007 |
| JP | 2008-156283 | A | 7/2008 |
| WO | WO 95/00162 | | 1/1995 |
| WO | WO 95/03325 | | 2/1995 |
| WO | WO 96/37508 | | 11/1996 |
| WO | WO 01/62827 | | 8/2001 |
| WO | WO 2004/060299 | A2 | 7/2004 |
| WO | WO 2004/089280 | | 10/2004 |
| WO | WO 2005/116655 | | 12/2005 |

(Continued)

OTHER PUBLICATIONS

Chapman, "PEGylated antibodies and antibody fragments for improved therapy: a review," Advanced Drug Delivery Reviews, vol. 54, pp. 531-545, (2002).

Davis, "The origin of pegnology," Advanced Drug Delivery Reviews, vol. 54, pp. 457-458, (2002).

Harris, et al., "Poly(ethylene glycol) Chemistry and Biological Applications", ACS Symposium Series, 11 pages, (1997).

Hinds, et al., "Effects of PEG conjugation on insulin properties," Advanced Drug Delivery Reviews, vol. 54, pp. 505-530, (2002).

Kinstler, et al., "Mono-N-terminal poly(ethylene glycol)-protein conjugates," Advanced Drug Delivery Reviews, vol. 54, pp. 477-485, (2002).

Nesher, et al., "Reversible Pegylation Prolongs the Hypotensive Effect of Atrial Natriuretic Peptide", Bioconjugate Chem., vol. 19, pp. 342-348, (2008).

Ouchi, et al., "Design of Antitumor Agent-Terminated Poly(Ethylene Glycol) Conjugate as Macromolecular Prodrug," Polymer Preprints, pp. 582-583, (1997).

(Continued)

*Primary Examiner* — James H Alstrum Acevedo
*Assistant Examiner* — Sergio Coffa

(57) ABSTRACT

The invention provides peptides that are chemically modified by covalent attachment of a water-soluble oligomer. A conjugate of the invention, when administered by any of a number of administration routes, exhibits characteristics that are different from the characteristics of the peptide not attached to the water-soluble oligomer.

9 Claims, 25 Drawing Sheets

(56) References Cited

FOREIGN PATENT DOCUMENTS

| | | | |
|---|---|---|---|
| WO | WO 2006/019950 A2 | 2/2006 |
| WO | WO 2006/110776 | 10/2006 |
| WO | WO 2007/075534 A2 | 7/2007 |
| WO | WO 2008/011165 A2 | 1/2008 |
| WO | WO 2008/082669 A2 | 7/2008 |
| WO | WO 2010/033207 | 3/2010 |

OTHER PUBLICATIONS

Pasut, et al., "Protein, peptide and non-peptide drug PEGylation for therapeutic application," Expert Opin. Ther. Patents, vol. 14, No. 6, pp. 859-894, (2004).
Qu, et al., "Protegrin Structure and Activity Against Neisseria Gonorrhoeae," Inf. and Immun., vol. 65, No. 2, pp. 636-639, (Feb. 1997).
Reddy, et al., "Use of peginterferon alfa-2a (40 KD) (Pegasys®) for the treatment of hepatitis C," Advanced Drug Delivery Reviews, vol. 54, pp. 571-586, (2002).
Roberts, et al., "Chemistry for peptide and protein PEGylation," Advanced Drug Delivery Reviews, vol. 54, pp. 459-476, (2002).
Sato, "Enzymatic procedure for site-specific pegylation of proteins," Advanced Drug Delivery Reviews, vol. 54, pp. 487-504, (2002).
Sims, et al., "A Method for the Estimation of Polyethylene Glycol in Plasma Protein Fractions," Analytical Biochemistry, vol. 107, pp. 60-63, (1980).
Steinberg, et al., "Protegrin-1: a Broad-Spectrum, Rapidly Microbicidal Peptide with In Vivo Activity," Antimicrob. Agents and Chemother., vol. 41, No. 8, pp. 1738-1742, (Aug. 1997).
Tran, et al., "Microbicidal Properties and Cytocidal Selectivity of Rhesus Macaque Theta Defensins", Antimicrobial Agents and Chemotheraphy, vol. 52, No. 3, pp. 944-953, (Mar. 2008).
Veronese, et al., "Introduction and overview of peptide and protein pegylation," Advanced Drug Delivery Reviews, vol. 54, pp. 453-456, (2002).
Veronese, et al., "Polyethylene glycol-superoxide dismutase, a conjugate in search of exploitation," Advanced Drug Delivery Reviews, vol. 54, pp. 587-606, (2002).
Wang, et al., "Structural and biological characterization of pegylated recombinant interferon alpha-2b and its therapeutic implications," Advanced Drug Delivery Reviews, vol. 54, pp. 547-570, (2002).
Wold, "Posttranslational Protein Modifications: Perspective and Prospectives," Posttranslational Covalent Modifications of Proteins, Academic Press, Inc., pp. 1-15, (1983).
Zalipsky, "Chemistry of polyethylene glycol conjugates with biologically active molecules," Adv. Drug Del. Rev., vol. 16, pp. 157-182, (1995).
Zalipsky, et al., "Use of Functionalized Poly(Ethylene Glycol)s for Modification of Polypeptides", Poly(Ethylene Glycol) Chemistry: Biotechnical and Biomedical Applications, Eds. J.M. Harris, Plenum Press, New York, 13 pages, (1992).
PCT International Search Report and Written Opinion corresponding to PCT Application No. PCT/US2009/005210 date of mailing Nov. 16, 2009.
PCT International Preliminary Report on Patentability corresponding to PCT Application No. PCT/US2009/005210 date of mailing Mar. 31, 2011.
PCT International Search Report and Written Opinion corresponding to PCT Application No. PCT/US2009/005192 date of mailing Jan. 27, 2010.
PCT International Preliminary Report on Patentability corresponding to PCT Application No. PCT/US2009/005192 date of mailing Mar. 31, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, 46 pages, Catalogue 2003-1st, (Jan. 2003).
NOF Corporation, PEG Derivatives, Phospholipid and Drug Delivery Materials for Pharmaceuticals, 27 pages, Catalogue 2003-2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Australian Patent Examination Report No. 1 corresponding to Australian Patent Application No. 2009292643 date of issue Oct. 3, 2014.
European Communication corresponding to European Patent Application No. 09 789 334.1 dated Sep. 5, 2012.
European Communication corresponding to European Patent Application No. 09 789 327.5 dated Sep. 5, 2012.
European Communication corresponding to European Patent Application No. 09 789 334.1 dated Aug. 16, 2013.
European Communication corresponding to European Patent Application No. 09 789 327.5 dated Jul. 19, 2013.
European Summons to attend oral proceedings corresponding to European Patent Application No. 09789327.5 dated Oct. 14, 2014.
English Translation of Mexican Official Letter Summary corresponding to Mexican Patent Application No. MX/a/2011/003117 dated Aug. 2, 2013.
English Translation Mexican Official Letter corresponding to Mexican Patent Application No. MX/a/2011/003117 dated Sep. 23, 2014.
Canadian Office Communication corresponding to Canadian Patent Application No. 2,737,040 dated May 7, 2015.
European Communication corresponding to European Patent Application No. 09 789 327.5 dated Feb. 17, 2015.
European Communication corresponding to European Patent Application No. 14200659.2 dated Apr. 15, 2015.
English translation of Japanese Notice of Reasons for Rejection corresponding to Japanese Patent Application No. 2011-527822 mailing date Jan. 30, 2014.
English Translation Mexican Official Letter corresponding to Mexican Patent Application No. MX/a/2011/003117 dated Feb. 13, 2014.
Australian Patent Examination Report No. 2 in Australian Patent Application No. 2009292643 date of issue Nov. 14, 2015.
Canadian Office Communication in Canadian Patent Application No. 2,737,040 dated Jan. 12, 2016.

(56) References Cited

OTHER PUBLICATIONS

Canadian Office Communication in Canadian Patent Application No. 2,737,040 dated Aug. 16, 2016.
European Office Communication in European Patent Application No. 14 200 659.2-1453 dated Sep. 12, 2016.
European Office Communication in European Patent Application No. 09 789 334.1-1453 dated Feb. 10, 2015.
European Office Communication in European Patent Application No. 09 789 334.1-1453 dated Mar. 15, 2016.
English Translation of Japanese Notice of Reasons for Rejection in Japanese Patent Application No. 2011-527822 mailing date 30 Jan. 30, 2015.

* cited by examiner

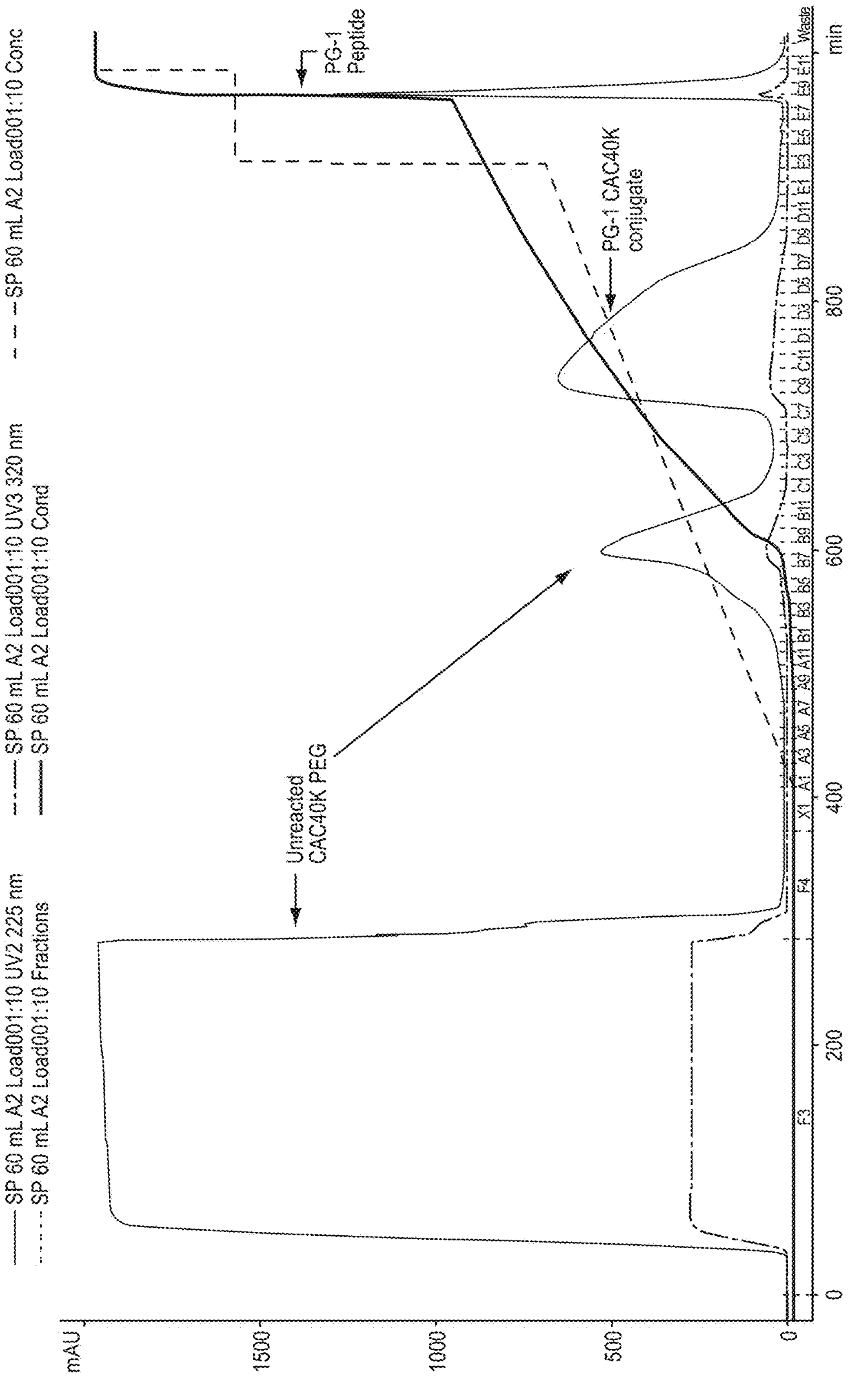
Figure PRO2.1

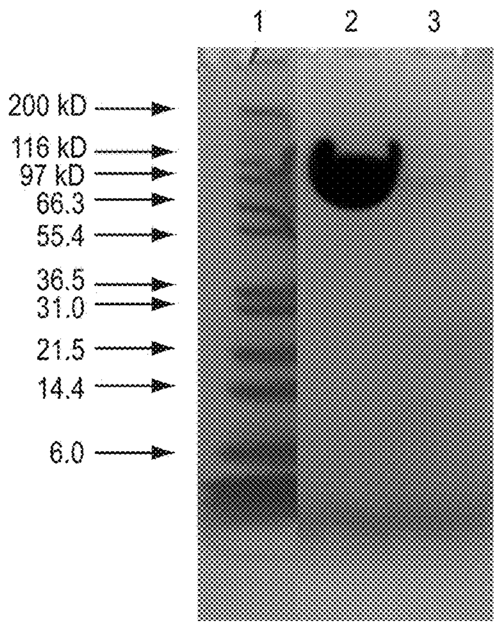
Figure PRO2.2
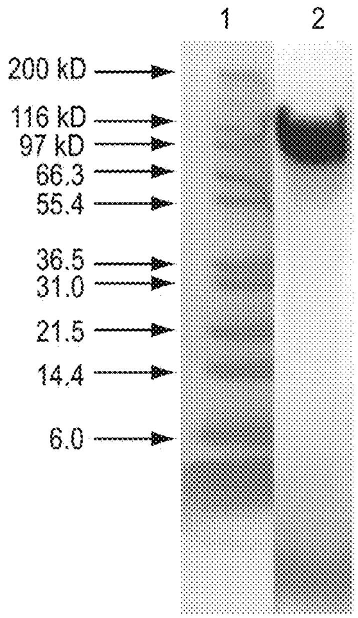
Figure PRO3.2

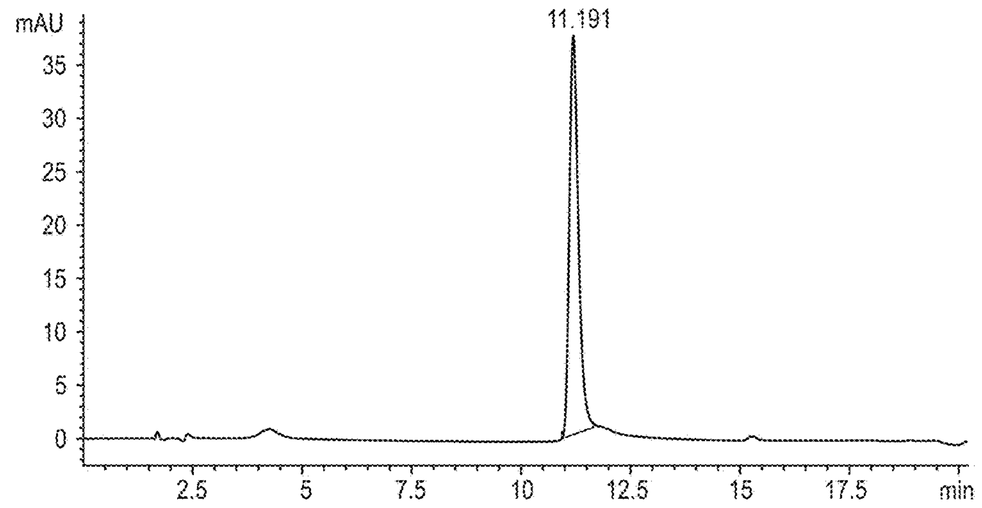
Figure PRO2.3
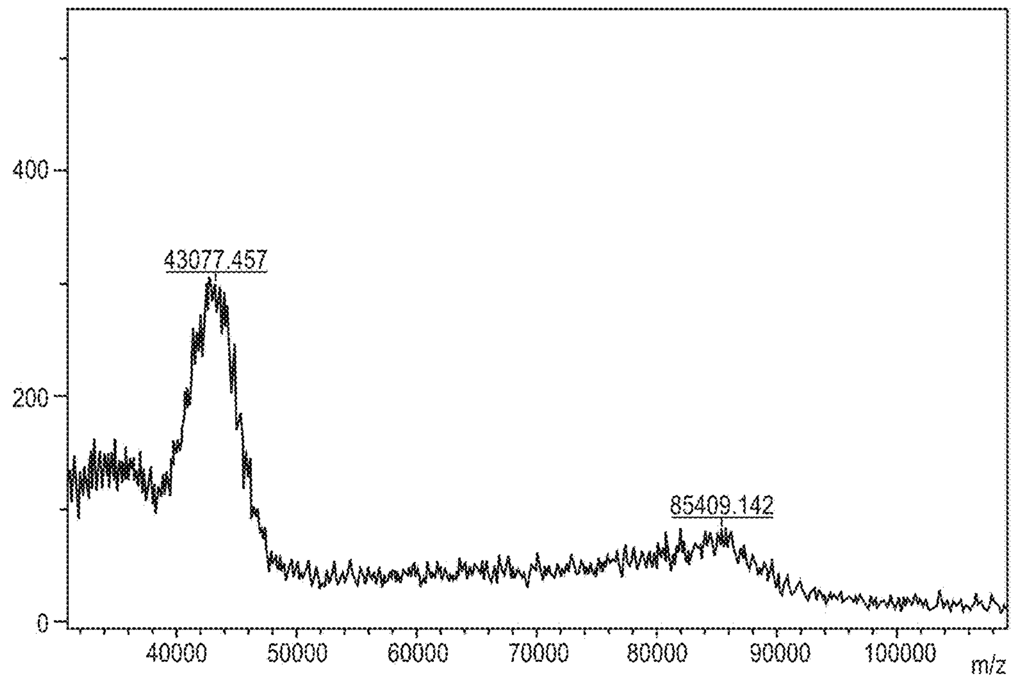
Figure PRO2.4

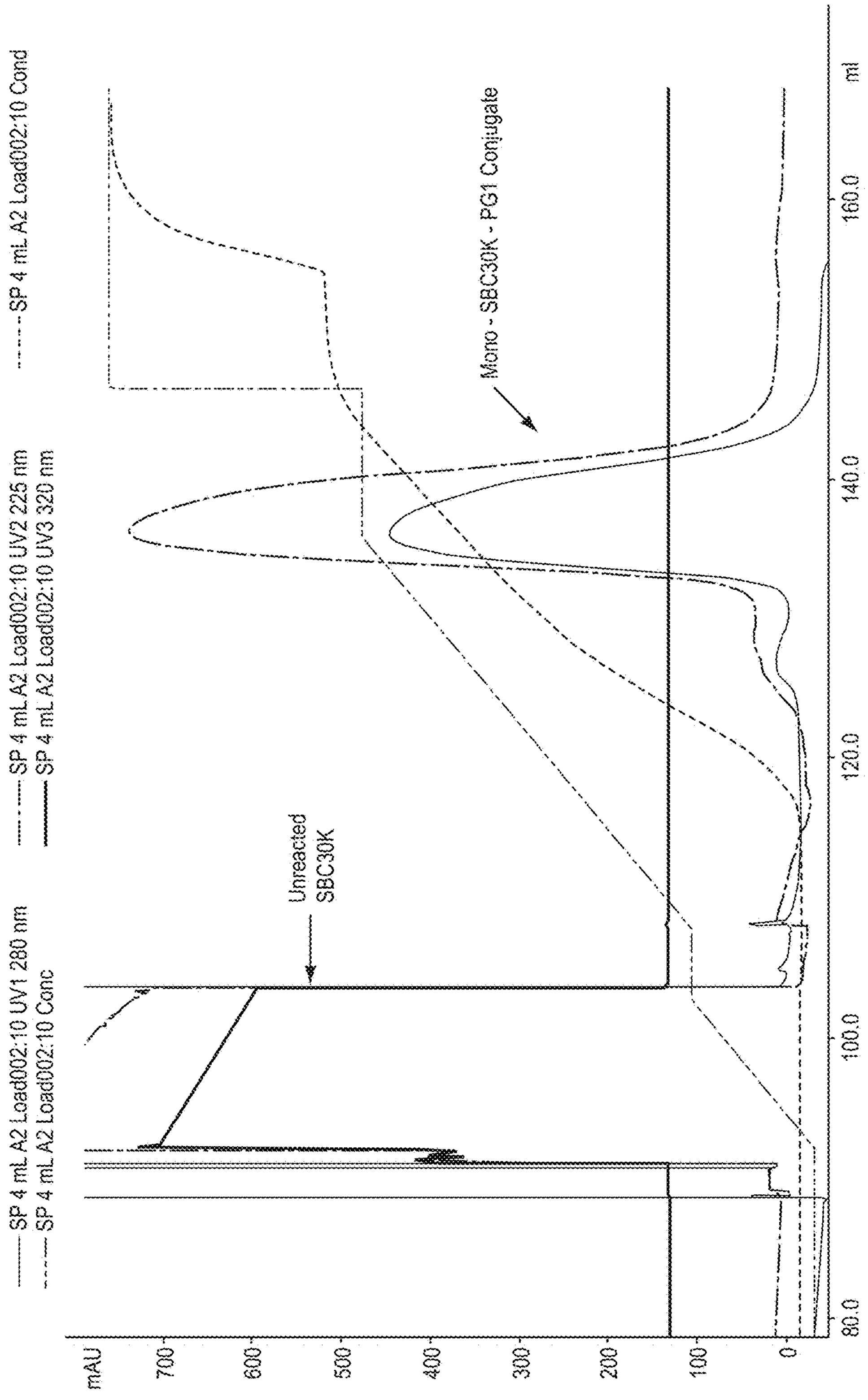
Figure PRO3.1

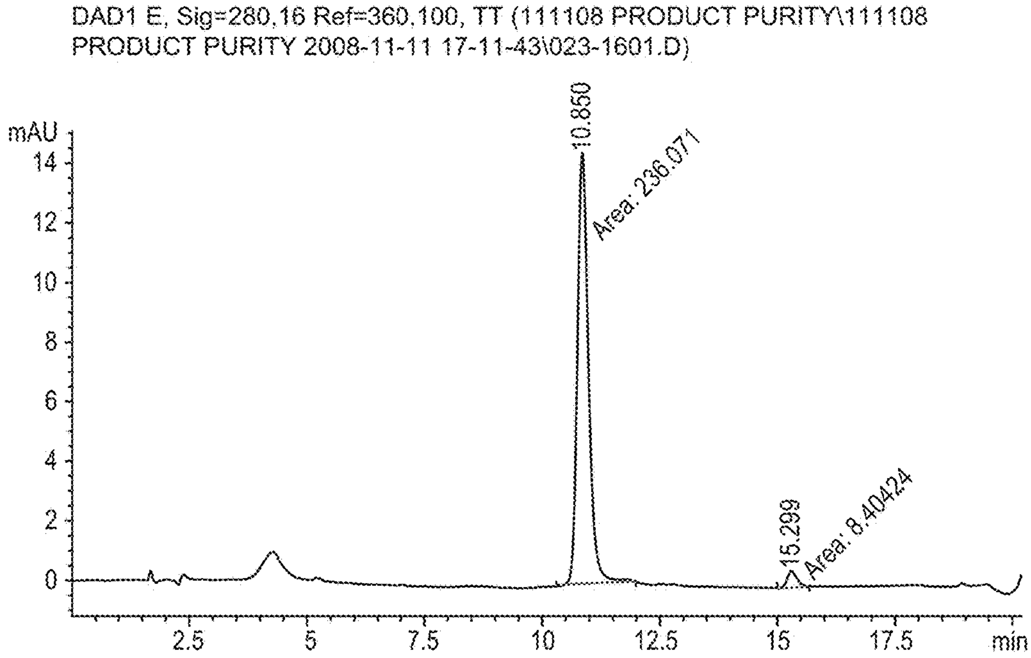
Figure PRO3.3
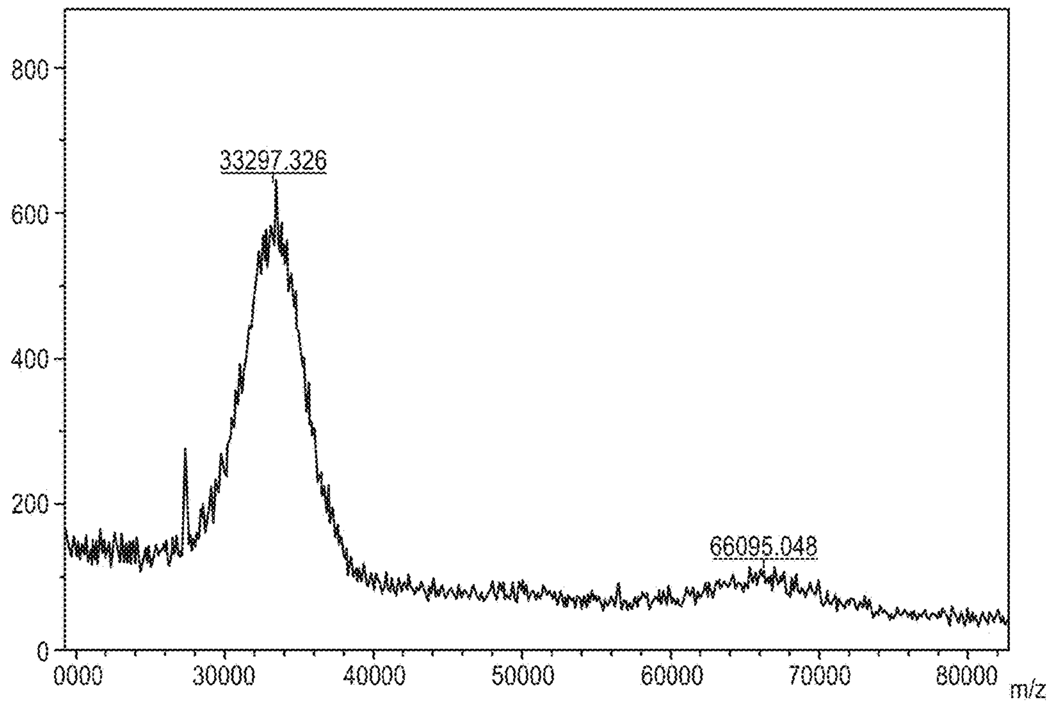
Figure PRO3.4

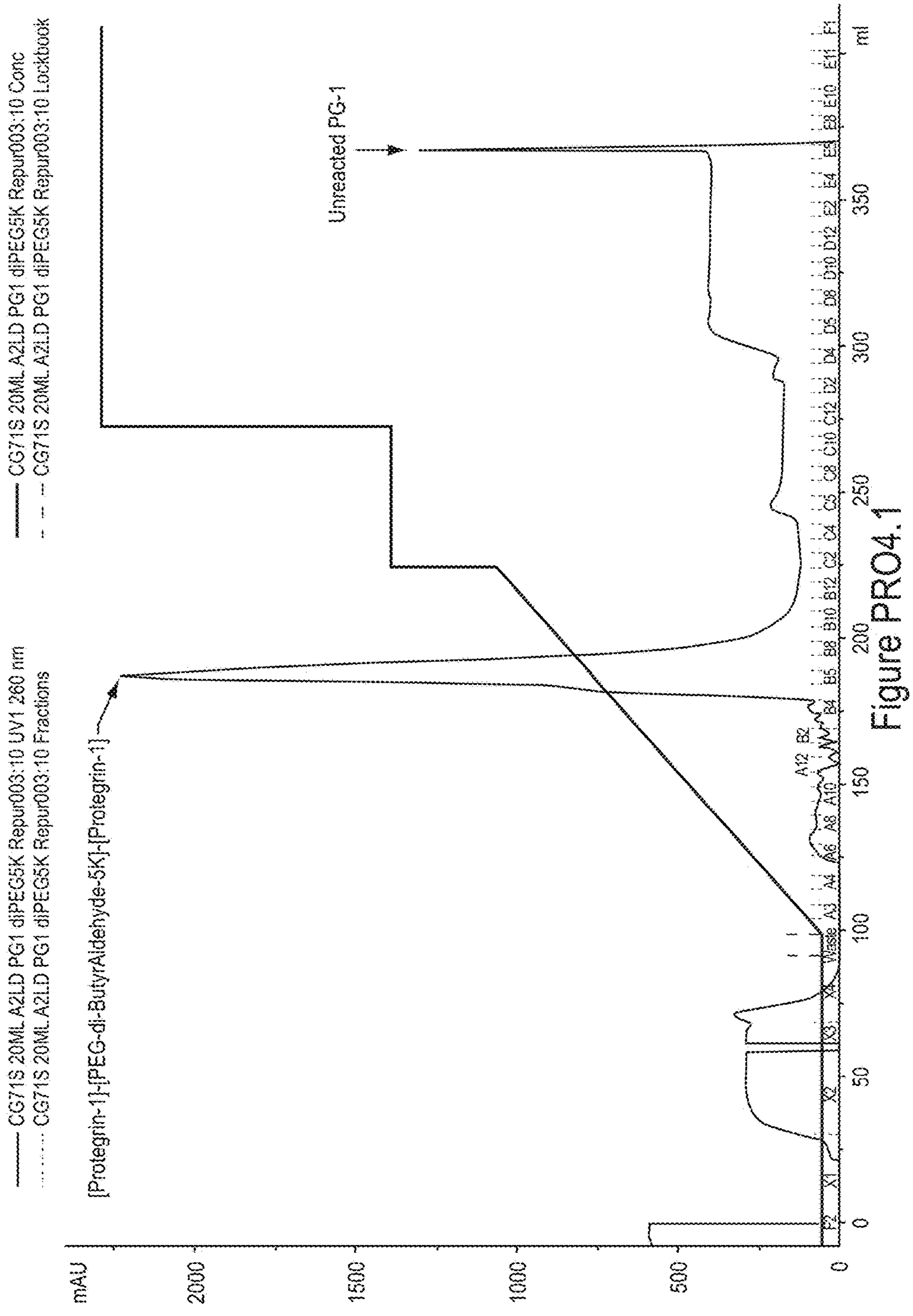
Figure PRO4.1

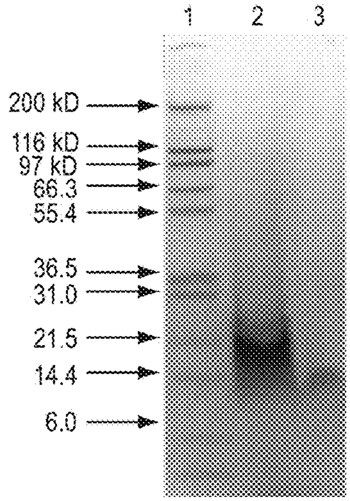
Figure PRO4.2
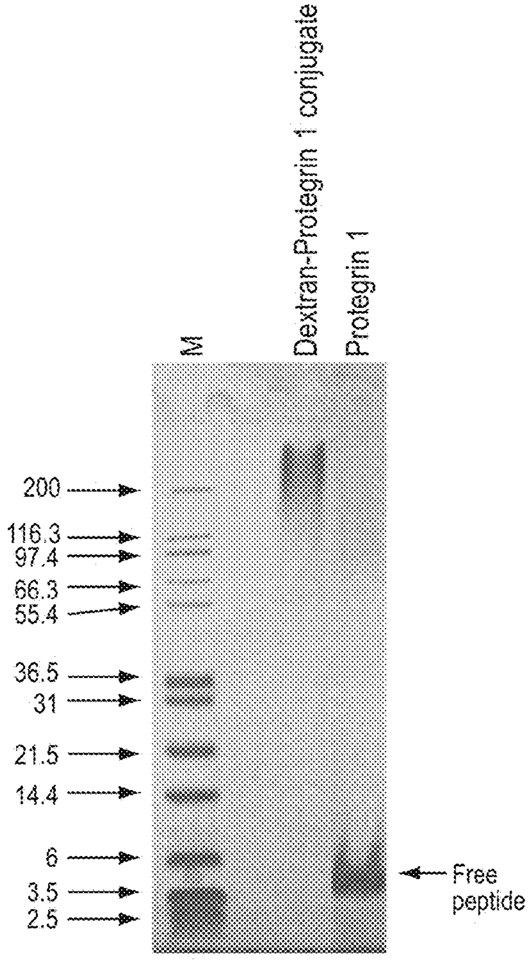
Figure PRO5.2

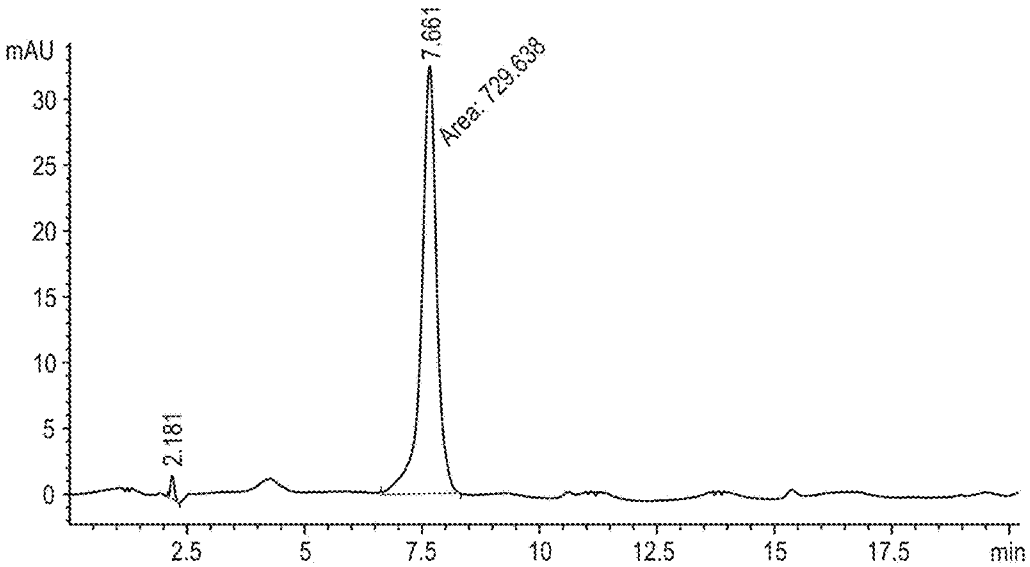
Figure PRO4.3
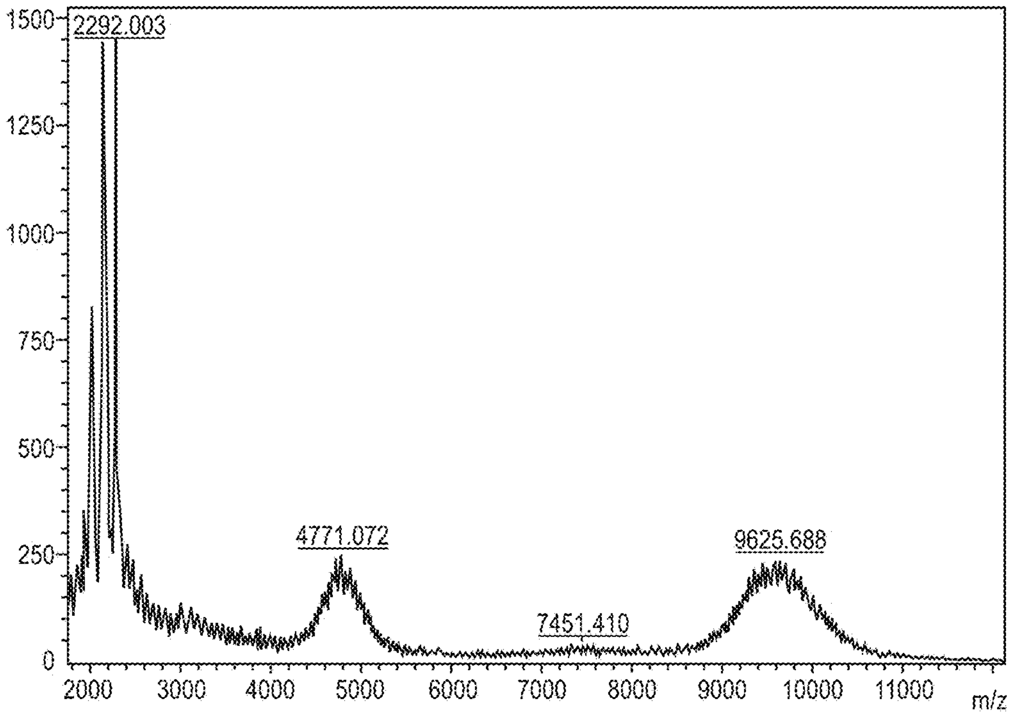
Figure PRO4.4

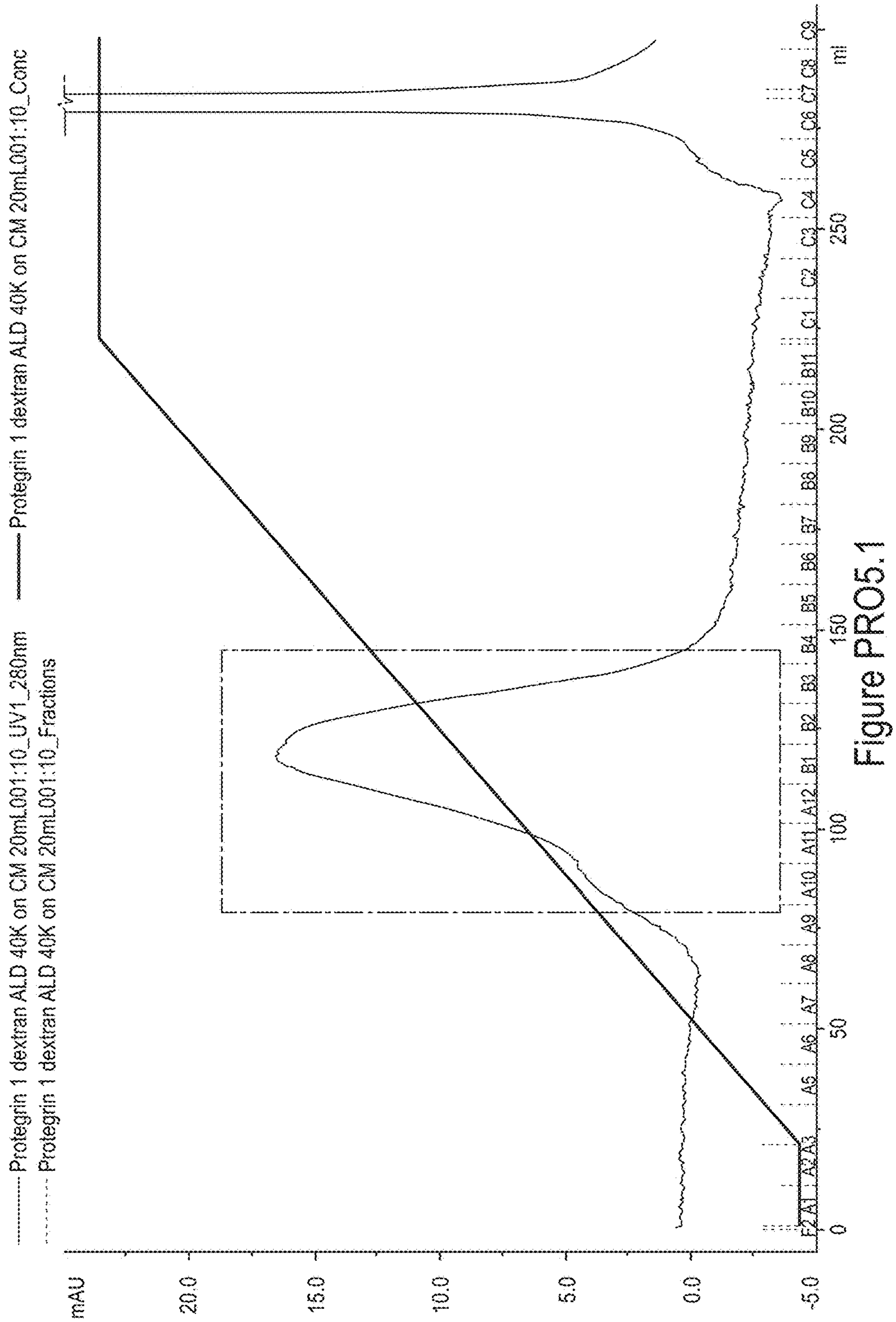
Figure PRO5.1

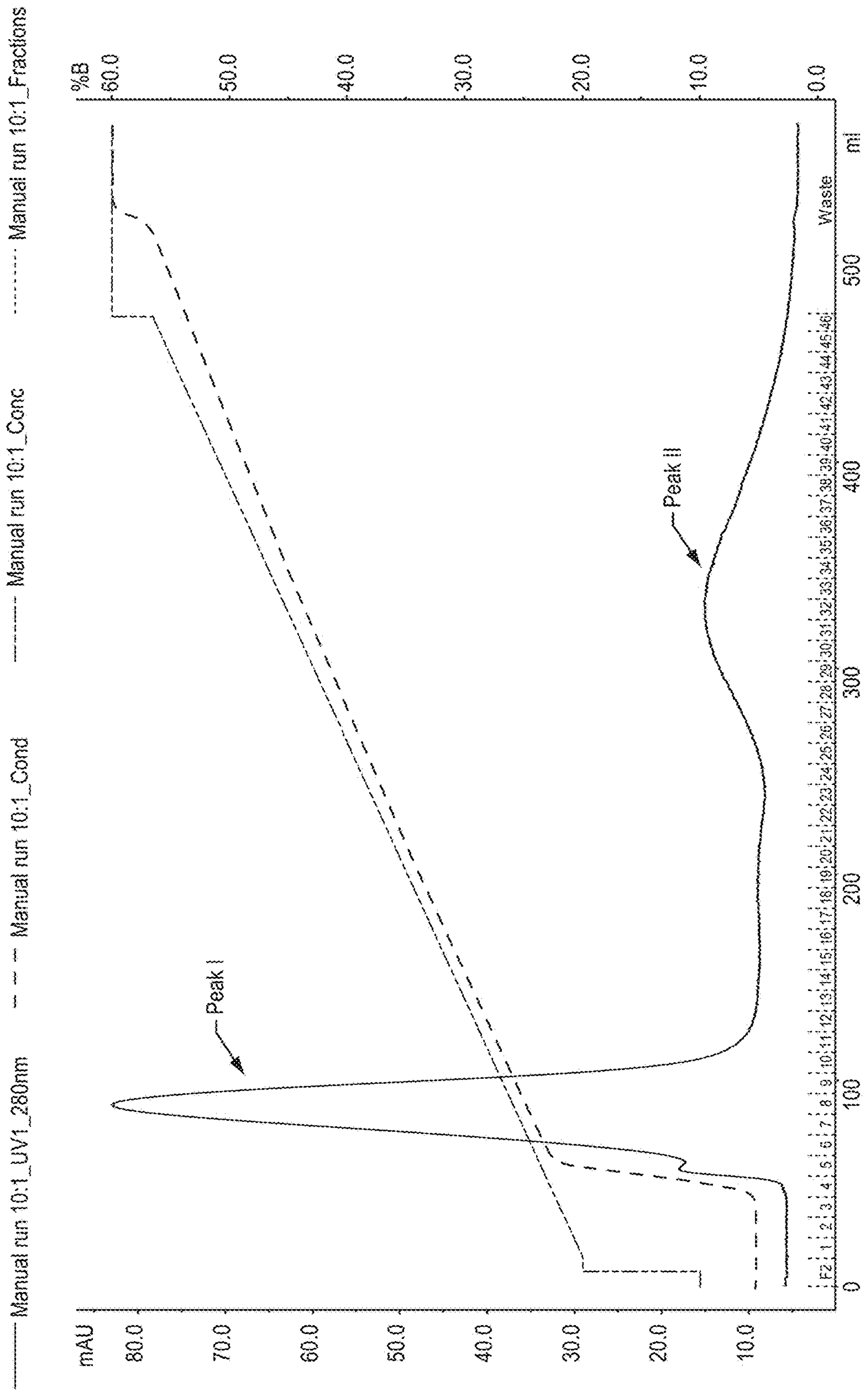
Figure PRO6.1

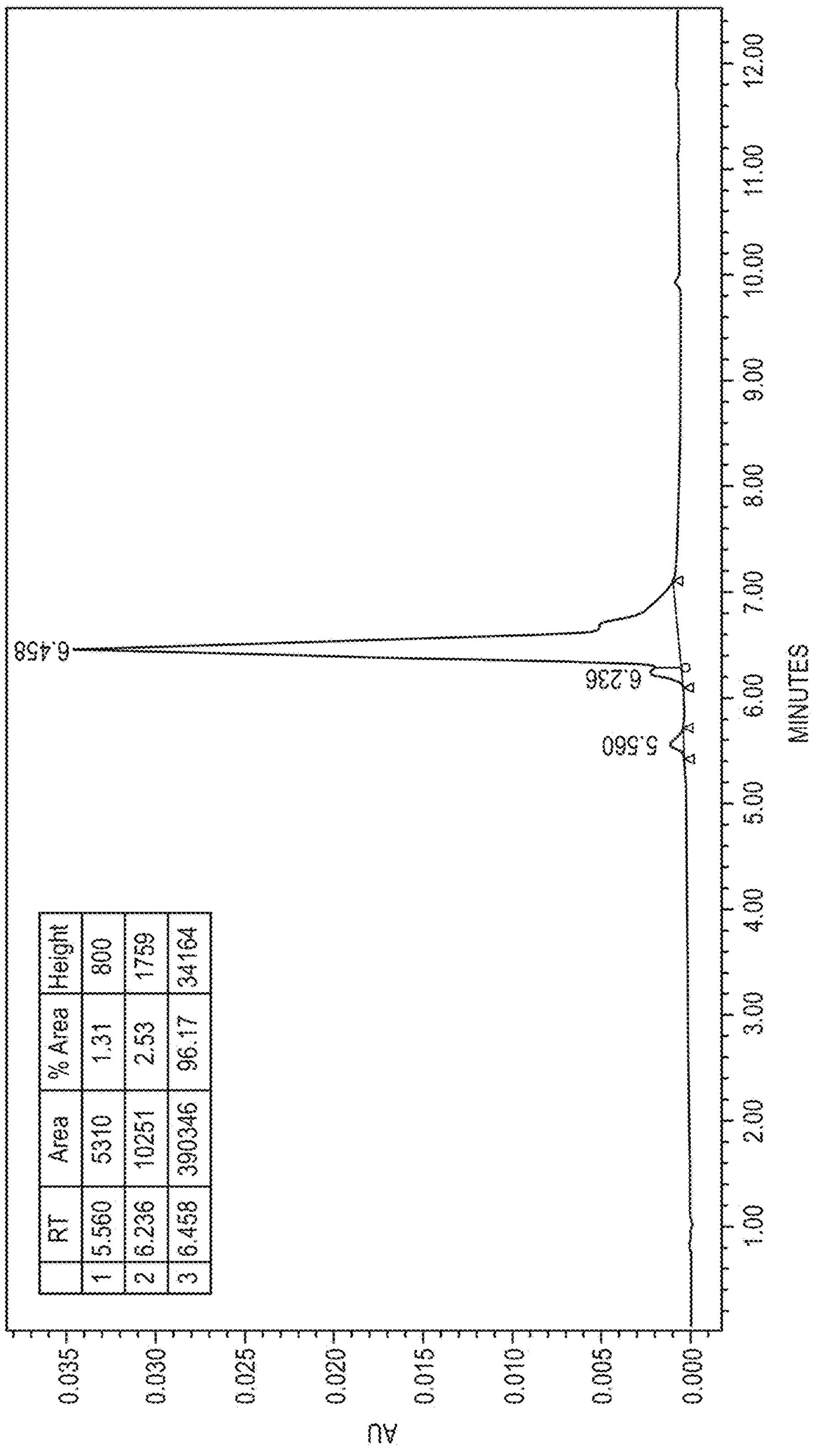
| | RT | Area | % Area | Height |
|---|---|---|---|---|
| 1 | 5.560 | 5310 | 1.31 | 800 |
| 2 | 6.236 | 10251 | 2.53 | 1759 |
| 3 | 6.458 | 390346 | 96.17 | 34164 |
Figure PRO6.2

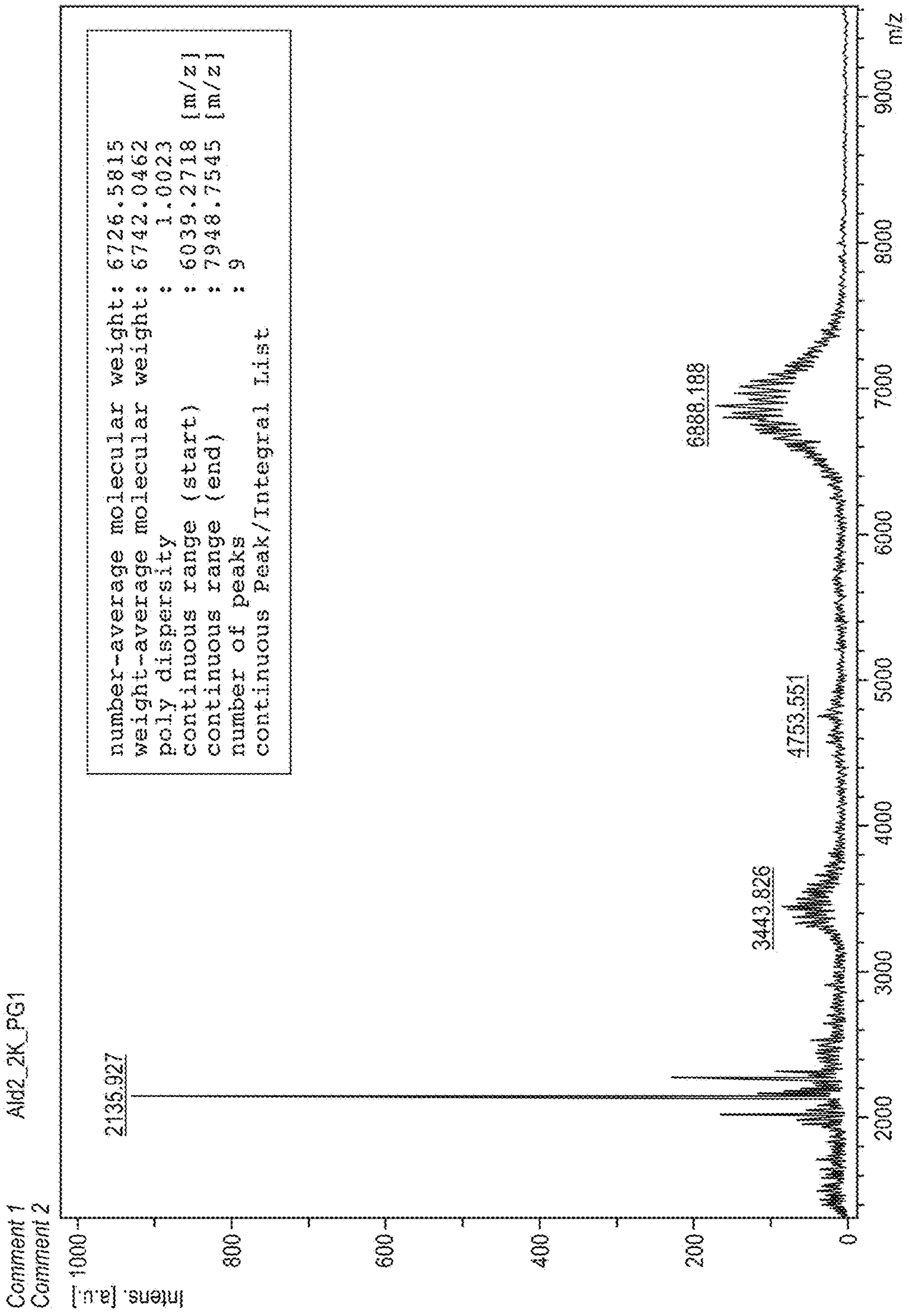
Figure PRO6.3

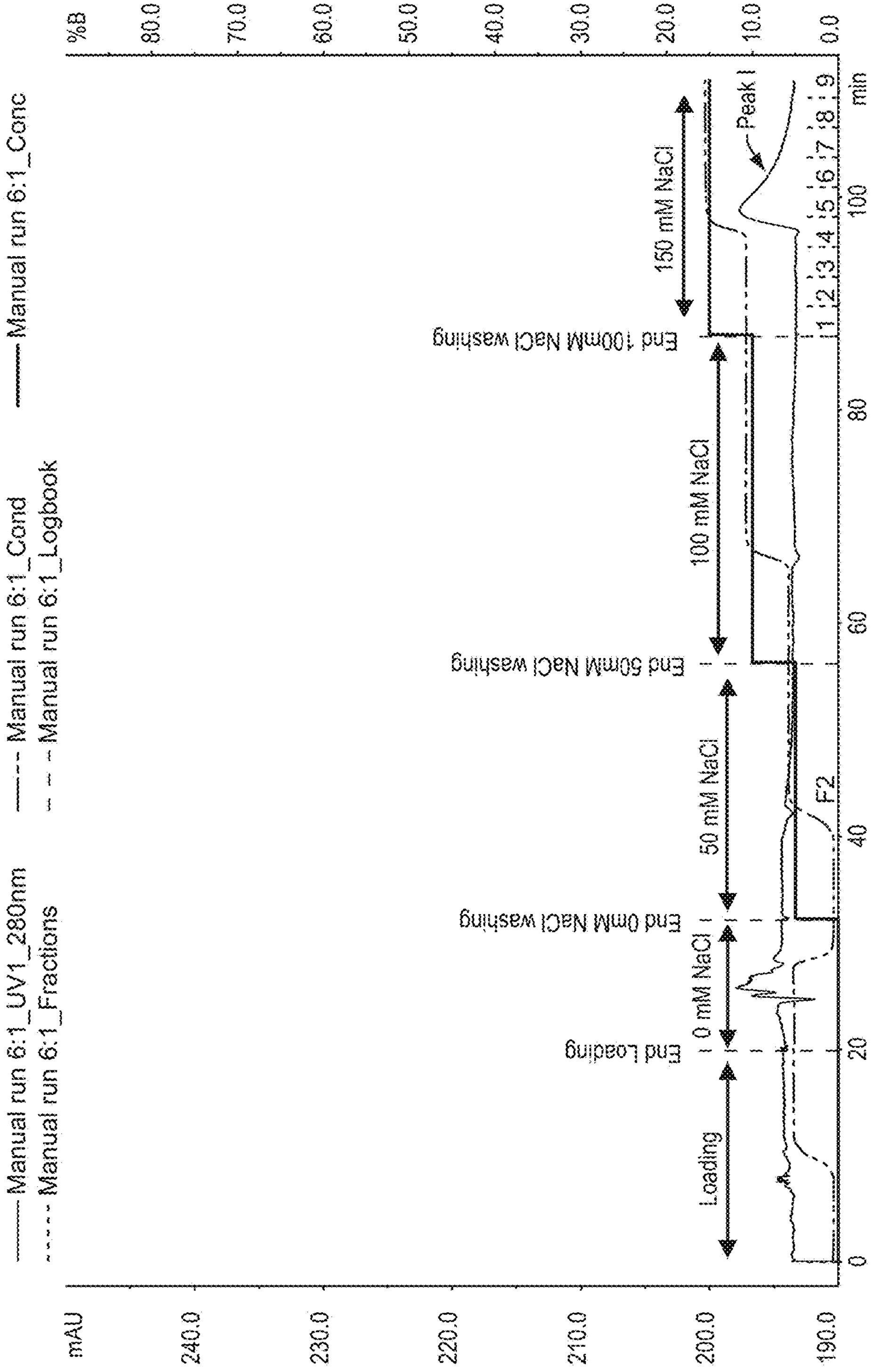
Figure PRO7.1.1

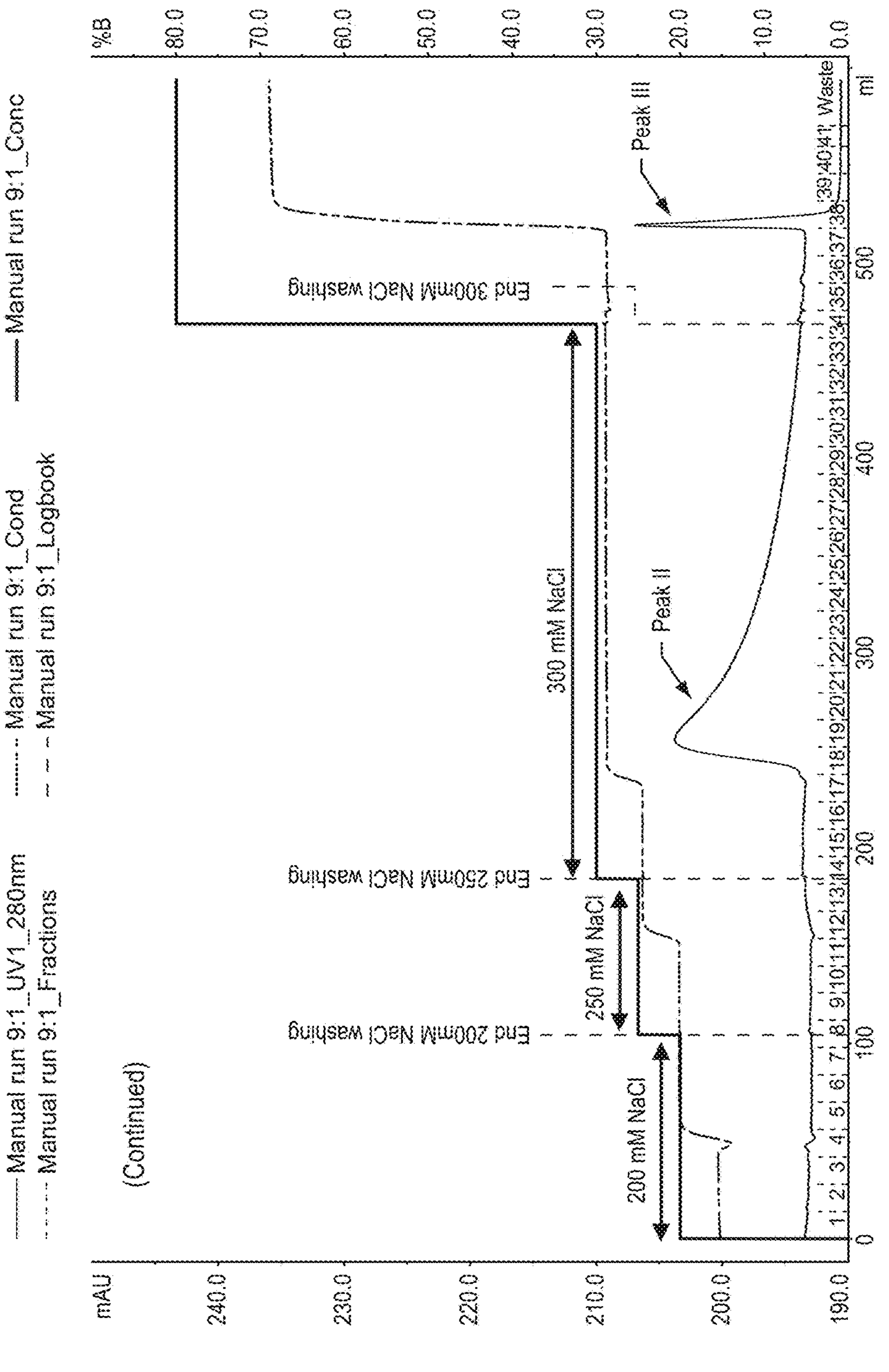
Figure 7.1.2

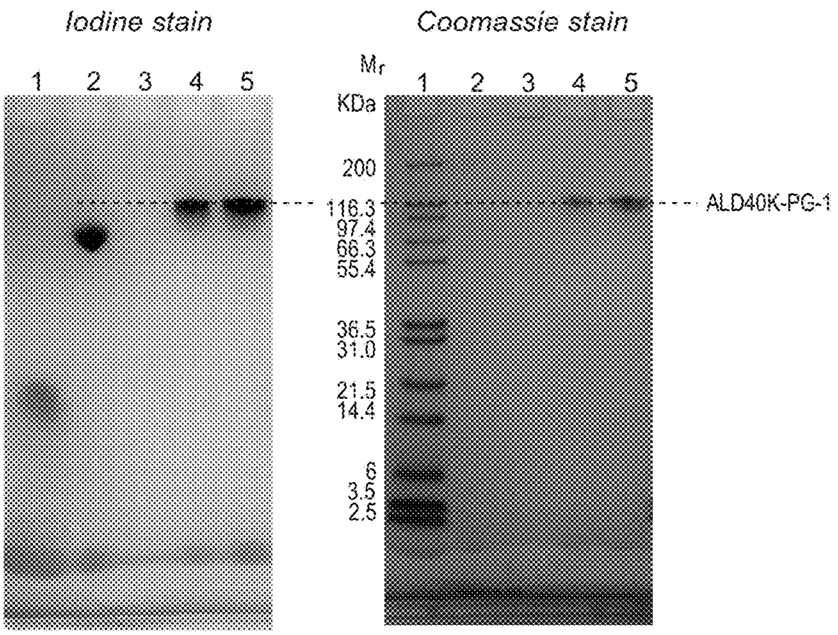
Figure PRO7.2

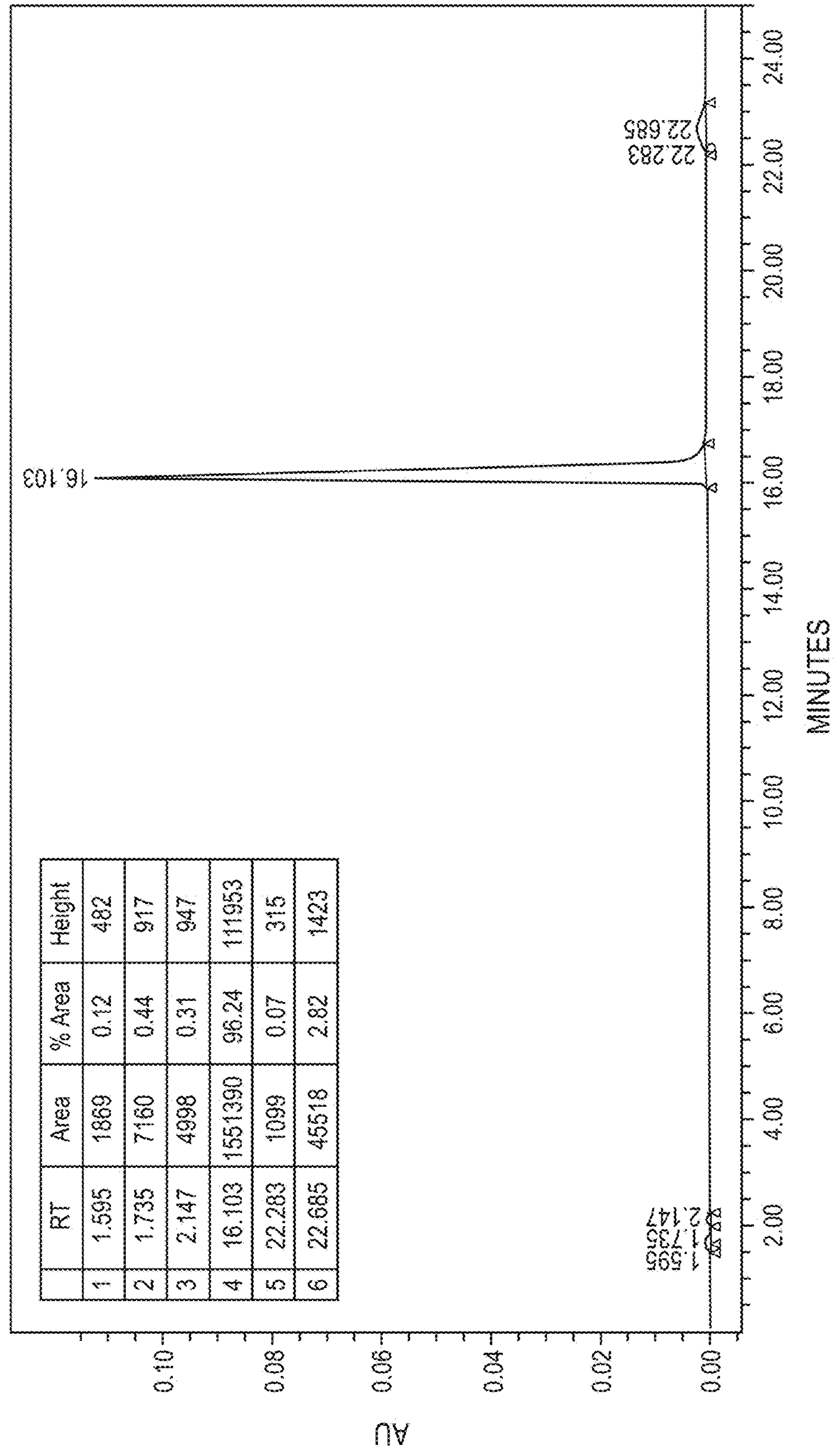
| | RT | Area | % Area | Height |
|---|---|---|---|---|
| 1 | 1.595 | 1869 | 0.12 | 482 |
| 2 | 1.735 | 7160 | 0.44 | 917 |
| 3 | 2.147 | 4998 | 0.31 | 947 |
| 4 | 16.103 | 1551390 | 96.24 | 111953 |
| 5 | 22.283 | 1099 | 0.07 | 315 |
| 6 | 22.685 | 45518 | 2.82 | 1423 |
Figure PRO7.3

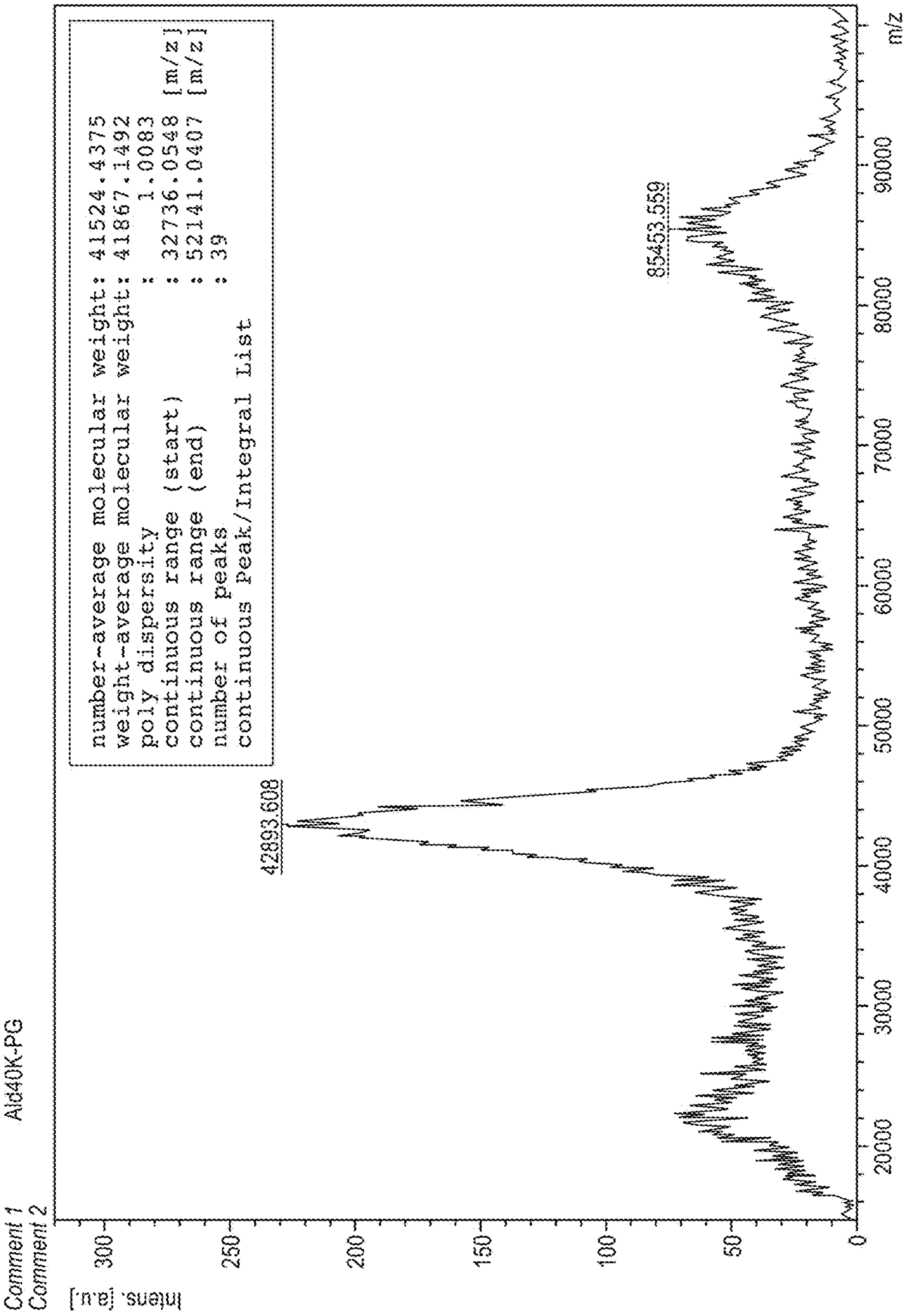
Figure PRO7.4

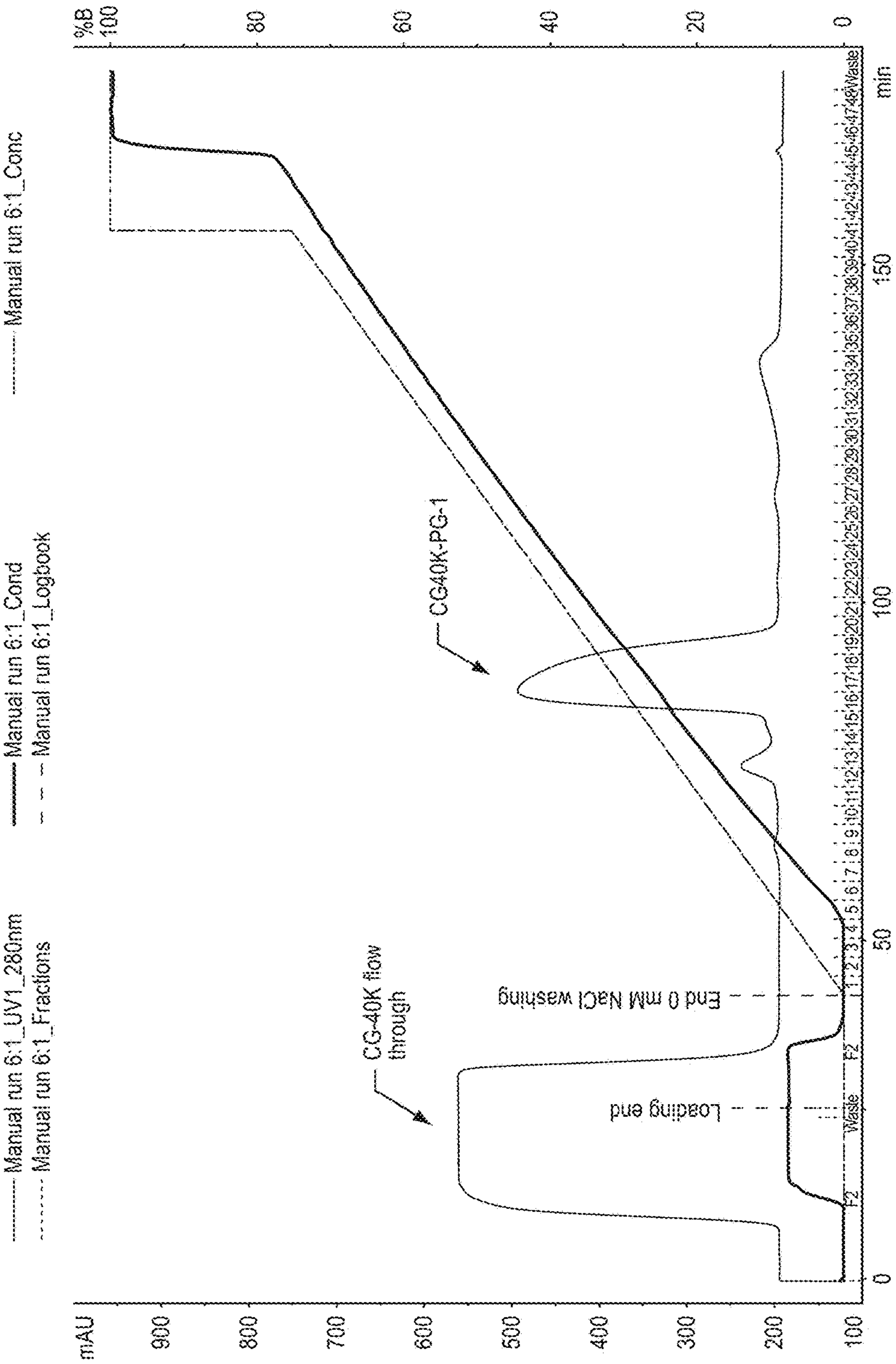
Figure PRO8.1

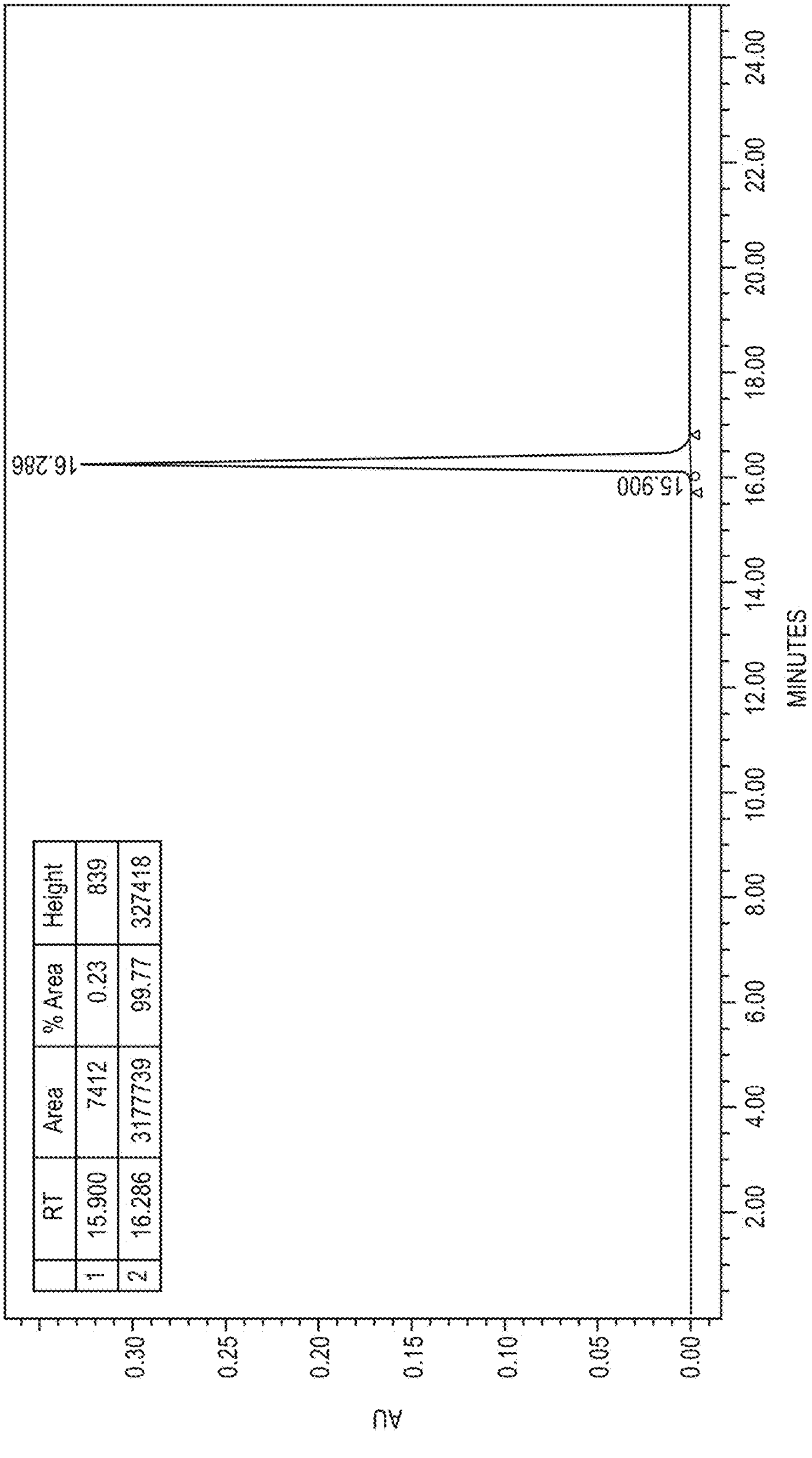
| | RT | Area | % Area | Height |
|---|---|---|---|---|
| 1 | 15.900 | 7412 | 0.23 | 839 |
| 2 | 16.286 | 3177739 | 99.77 | 327418 |
Figure PRO8.2

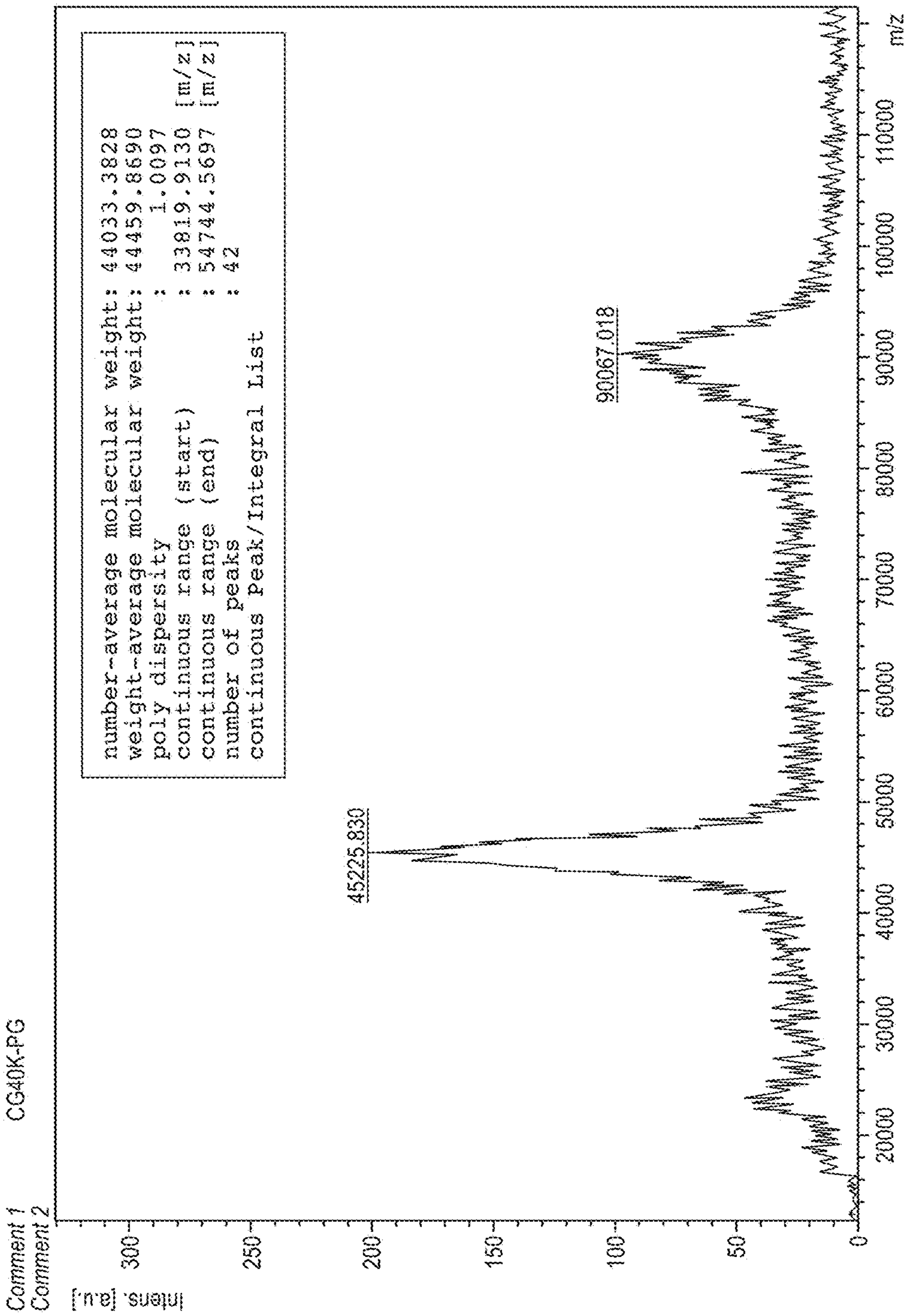
Figure PRO8.3

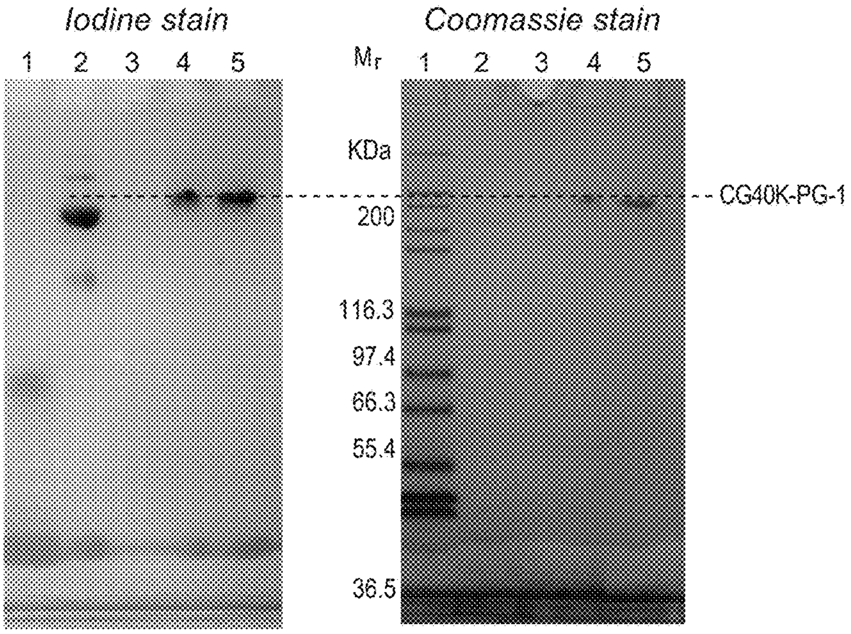
Figure PRO8.4
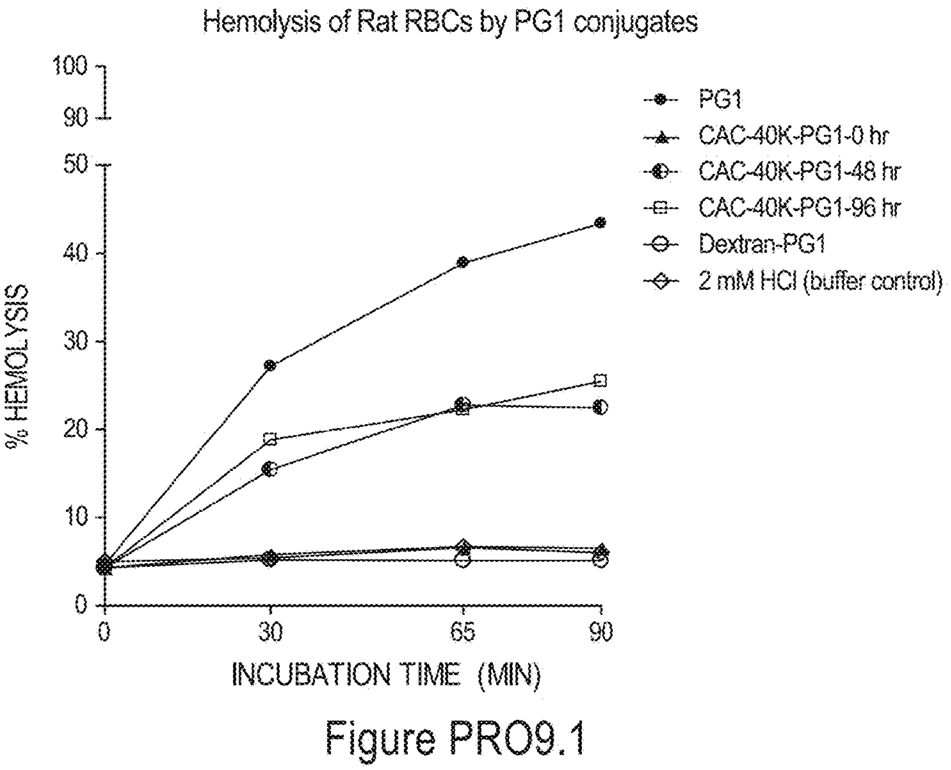
Figure PRO9.1

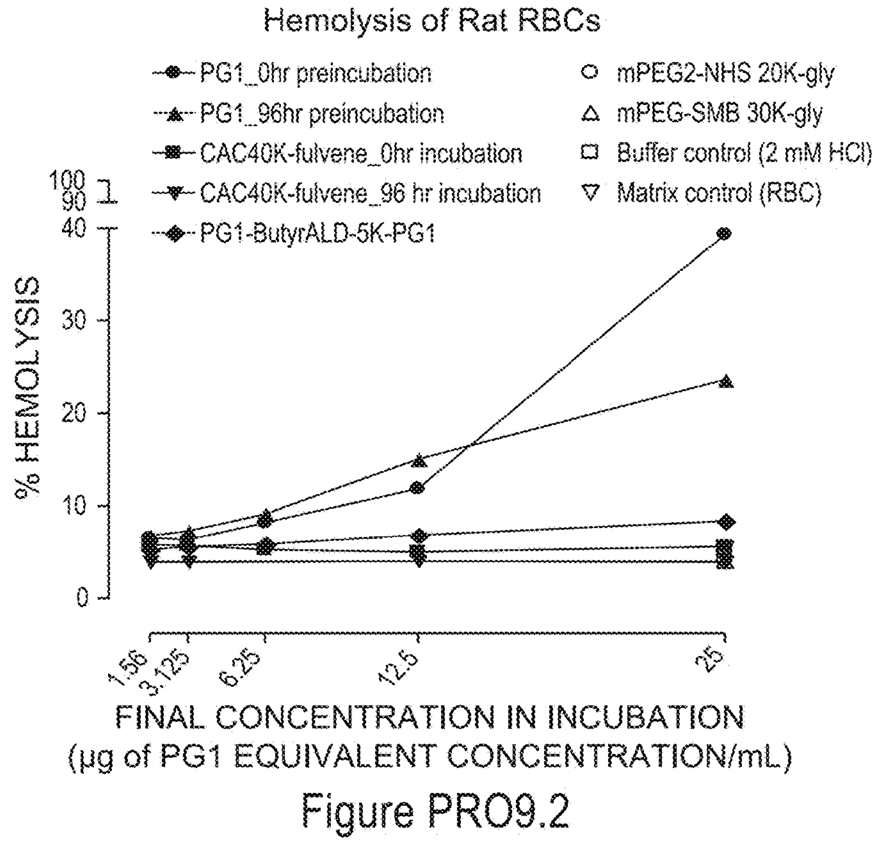
Figure PRO9.2
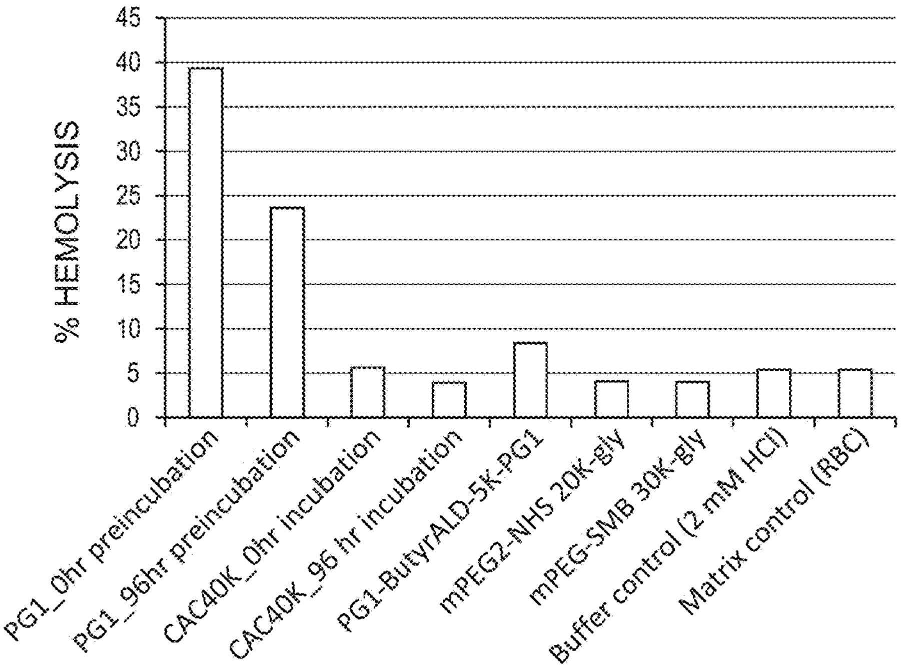
Figure PRO9.3

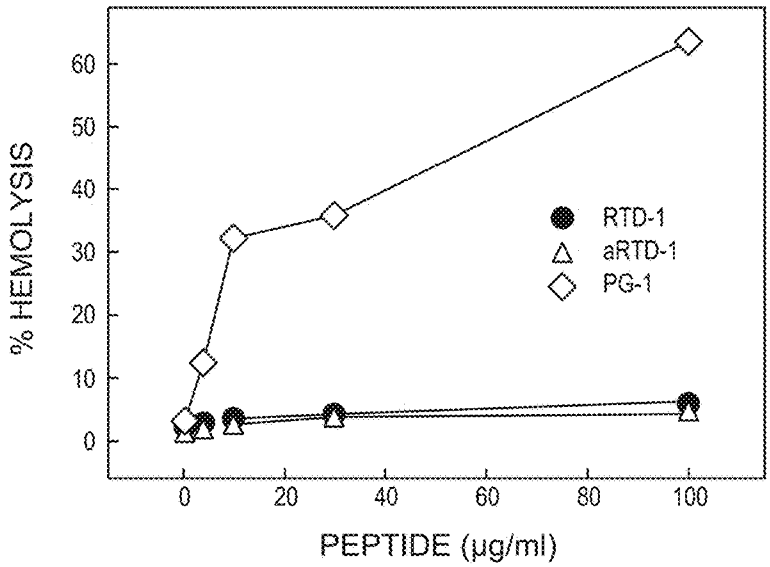
Figure PRO9.4
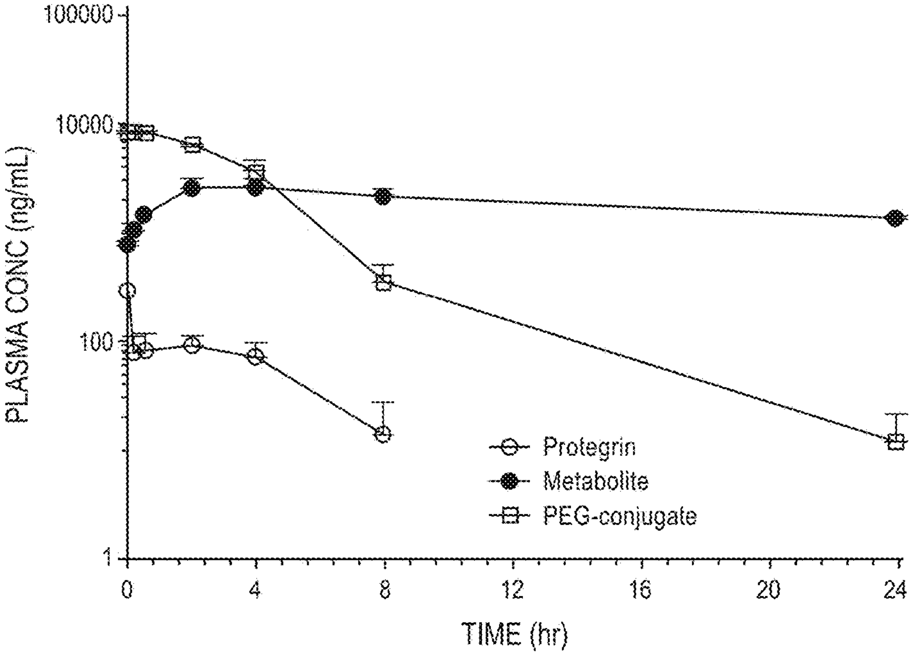
Figure PRO10.1

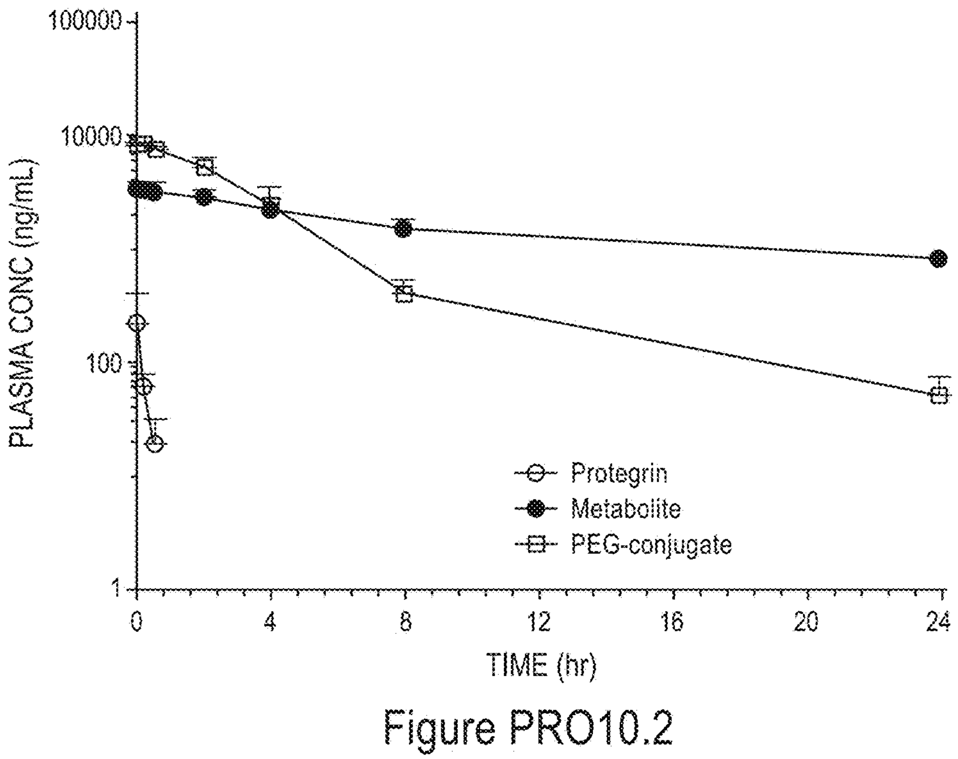
Figure PRO10.2
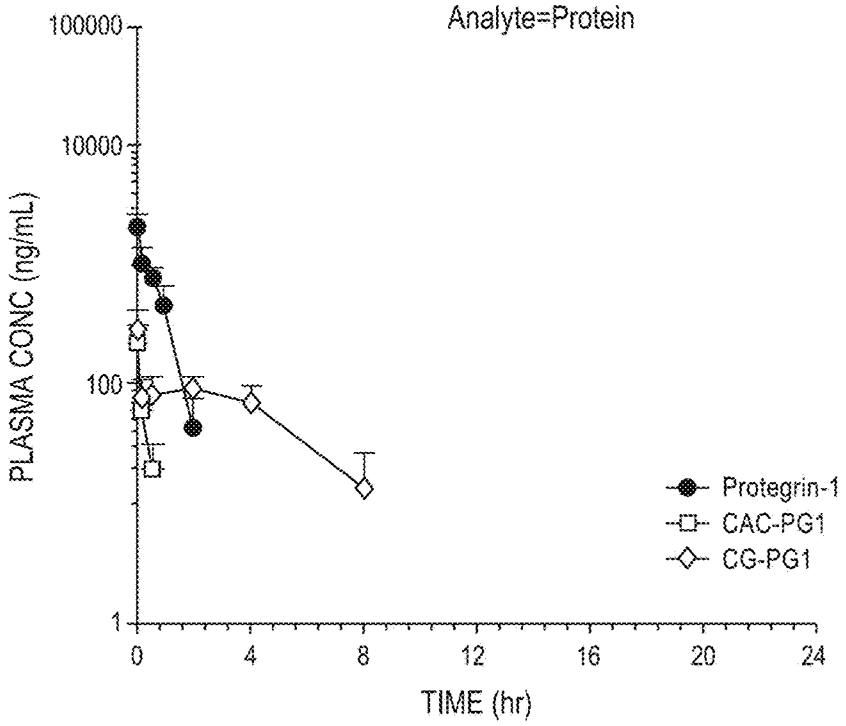
Figure PRO10.3

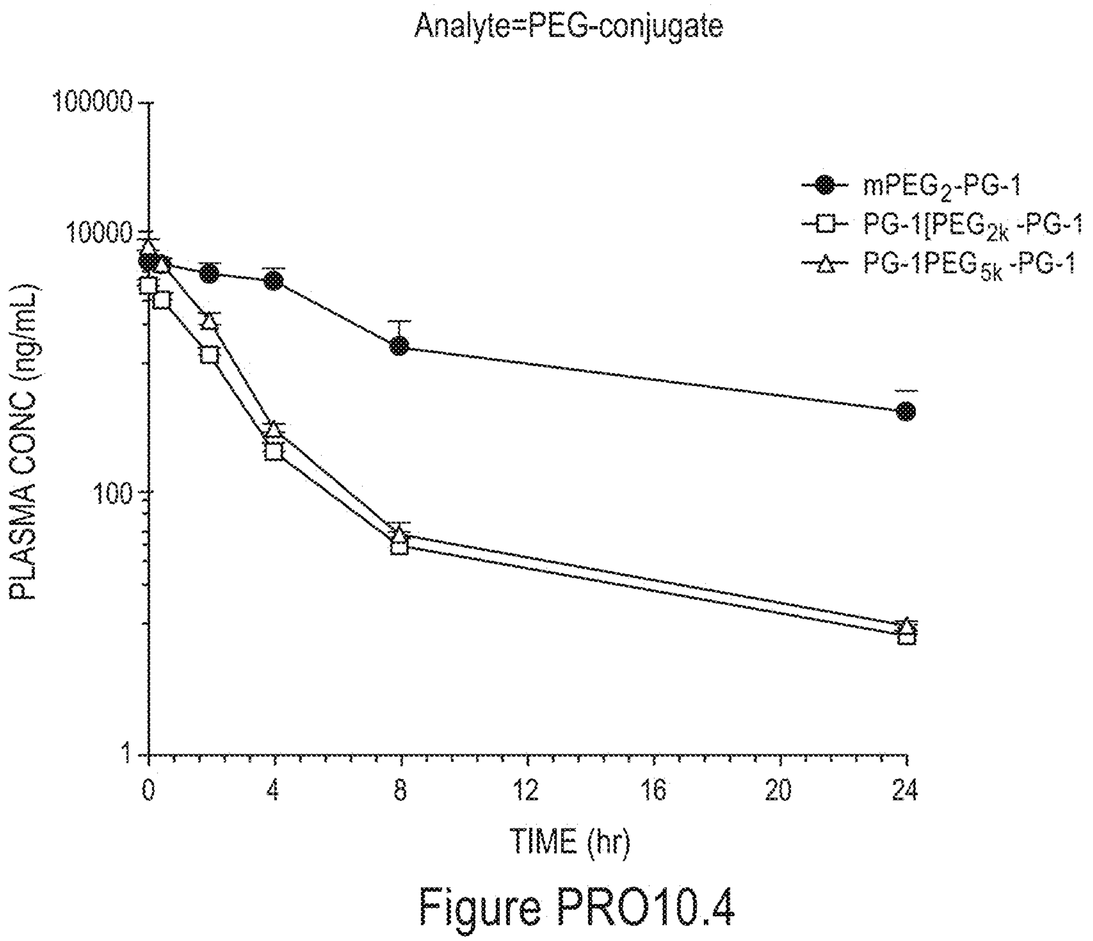
Figure PRO10.4

SEQUENCE LISTING

<160> NUMBER OF SEQ ID NOS: 6

<210> SEQ ID NO 1
<211> LENGTH: 18
<212> TYPE: PRT
<213> ORGANISM: Sus scrofa
<220> FEATURE:
<221> NAME/KEY: MOD_RES
<222> LOCATION: (18)..(18)
<223> OTHER INFORMATION: AMIDATION

<400> SEQUENCE: 1

Arg Gly Gly Arg Leu Cys Tyr Cys Arg Arg Arg Phe Cys Val Cys Val
1               5                   10                  15

Gly Arg

<210> SEQ ID NO 2
<211> LENGTH: 16
<212> TYPE: PRT
<213> ORGANISM: Sus scrofa

<400> SEQUENCE: 2

Arg Gly Gly Arg Leu Cys Tyr Cys Arg Arg Arg Phe Cys Ile Cys Val
1               5                   10                  15

<210> SEQ ID NO 3
<211> LENGTH: 19

<212> TYPE: PRT
<213> ORGANISM: Sus scrofa

<400> SEQUENCE: 3

Arg Gly Gly Gly Leu Cys Tyr Cys Arg Arg Arg Phe Cys Val Cys Val
1 5 10 15

Gly Arg Gly

<210> SEQ ID NO 4
<211> LENGTH: 19
<212> TYPE: PRT
<213> ORGANISM: Sus scrofa

<400> SEQUENCE: 4

Arg Gly Gly Arg Leu Cys Tyr Cys Arg Gly Trp Ile Cys Phe Cys Val
1 5 10 15

Gly Arg Gly

<210> SEQ ID NO 5
<211> LENGTH: 19
<212> TYPE: PRT
<213> ORGANISM: Sus scrofa

<400> SEQUENCE: 5

Arg Gly Gly Arg Leu Cys Tyr Cys Arg Pro Arg Phe Cys Val Cys Val
1 5 10 15

Gly Arg Gly

<210> SEQ ID NO 6
<211> LENGTH: 149
<212> TYPE: PRT
<213> ORGANISM: Sus scrofa

<400> SEQUENCE: 6

Met Glu Thr Gln Arg Ala Ser Leu Cys Leu Gly Arg Trp Ser Leu Trp
1 5 10 15

Leu Leu Leu Leu Gly Leu Val Val Pro Ser Ala Ser Ala Gln Ala Leu
20 25 30

Ser Tyr Arg Glu Ala Val Leu Arg Ala Val Asp Arg Leu Asn Glu Gln
35 40 45

Ser Ser Glu Ala Asn Leu Tyr Arg Leu Leu Glu Leu Asp Gln Pro Pro
50 55 60

Lys Ala Asp Glu Asp Pro Gly Thr Pro Lys Pro Val Ser Phe Thr Val
65 70 75 80

Lys Glu Thr Val Cys Pro Arg Pro Thr Arg Gln Pro Pro Glu Leu Cys
85 90 95

Asp Phe Lys Glu Asn Gly Arg Val Lys Gln Cys Val Gly Thr Val Thr
100 105 110

Leu Asp Gln Ile Lys Asp Pro Leu Asp Ile Thr Cys Asn Glu Val Gln
115 120 125

Gly Val Arg Gly Gly Arg Leu Cys Tyr Cys Arg Pro Arg Phe Cys Val
130 135 140

Cys Val Gly Arg Gly
145

POLYMER CONJUGATES OF PROTEGRIN PEPTIDES

CROSS REFERENCE TO RELATED APPLICATION

This application claims the benefit of priority under 35 U.S.C. §119(e) to U.S. Provisional Patent Application Ser. No. 61/192,586, filed 19 Sep. 2008, the disclosure of which is incorporated herein by reference in its entirety.

FIELD OF THE INVENTION

Among other things, the present invention relates to conjugates comprising a protegrin peptide moiety covalently attached to one or more water-soluble polymers.

BACKGROUND OF THE INVENTION

Several hundreds of proteins/peptides are known to cause membrane damage and to lead to cell death. They are found in many organisms such as plants, insects, frogs, snakes, and humans. Many such peptides are used by nature as either host defense (antimicrobial peptides) or offense (toxins from spider and snake venom). Since the body produces peptides that act against its own cells, the cytotoxic peptides are involved in "autocytotoxic" conditions. In addition to the wild-type cytolytic peptides, synthetic peptides modified from naturally occurring cytolytic peptides can also be cytotoxic, with mutation-sensitive activities. The size of the protein ranges from a short peptide to several hundreds of amino acids. Both large proteins and small peptides share a common feature, the ability to create a leakage pathway for molecules and ions to cross lipid bilayers.

The monomeric structures of small cytolytic peptides can be classified into three groups: α-helix, β-sheet, and loop-strand. These peptides adopt totally different structures under different conditions, allowing the conformation to adjust to the surrounding environment. Most α-helical cytolytic peptides are largely random coil in solution and change to an α-helix within the membrane. Theft-strand and loop-strand peptides often have disulfide S—S bond(s) that constrain the peptide conformation. Even though it is uncertain whether these disulfide bond-constrained peptides will have similar conformations in solution and in the membrane, it is commonly assumed that the disulfide bonds will keep the β-sheet structure unchanged. The most prominent characteristic of the small cytolytic peptides is that they are largely amphipathic, with hydrophobic and positively charged hydrophilic regions (with an excess of Lys and Arg residues). Positively charged residues can facilitate an initial contact between the peptides and the polyanionic sites in the membrane. Amphipathicity is essential for the membrane disruption effects by these peptides.

One of the best characterized β-sheet cytolytic peptide is protegrin. Native protegrins were originally purified from porcine leukocytes. There are five known porcine protegrins, PG-1-PG-5. These peptides share a common feature and conformation. Protegrin (PG-1) forms the f-hairpin conformation, which is composed of 18 amino acids (RGGRL-CYCRR-RFCVC-VGR) with a high content of cysteine (Cys) and positively charged arginine (Arg) residues. Formation of two disulfide bonds between the cysteine residues in PG-1 is crucial for the peptide activity, since the activity can be restored by stabilizing the peptide structure. It was noted that the translocation ability of PG-1 is coupled to its pore-formation capacity and depends on its folding to the β-hairpin conformation. PG-1 is a very potent antibiotic peptide, and experimental NMR study has revealed the three-dimensional structure of PG-1 in solution.

The interaction of protegrin with the membrane strongly depends on its lipid composition. Recent experimental studies have shown that PG-1 inserts readily into a membrane composed of negatively charged anionic lipids with the phosphatidylglycerol (PG) headgroup but significantly less into a membrane composed of neutrally charged lipids with the phosphatidylcholine (PC) or phosphatidylethanolamine (PE) headgroups. The major role of protegrins in the membrane is a channel formation that causes an ion leakage. Recently, it has been reported that either PG-1 or PG-3 can induce weak anion-selective channels and potassium leakage from liposomes and that PG-3 formed moderately cation-selective channels in the presence of bacterial lipopolysaccharide in planar phospholipid bilayers. Formation of protegrin channels disrupts the membrane surface by creating a pore across the membrane. PG-1 adopts a dimeric structure in DPC (dodecylphosphocholine) micelles, and a channel is formed by the association of several dimmers.

Normally, peptides suffer from a short in vivo half life, sometimes mere minutes, making them generally impractical, in their native form, for protegrin administration. Thus there exists a need in the art for modified protegrin peptides having an enhanced half-life and/or reduced clearance as well as additional protegrin advantages as compared to the protegrin peptides in their unmodified form.

SUMMARY OF THE INVENTION

Accordingly, the present invention provides conjugates comprising a protegrin peptide moiety covalently attached to one or more water-soluble polymers. The water-soluble polymer may be stably bound to the protegrin peptide moiety, or it may be releasably attached to the protegrin peptide moiety.

The invention further provides methods of synthesizing such protegrin peptide polymer conjugates and compositions comprising such conjugates. The invention further provides methods of treating, preventing, or ameliorating a disease, disorder or condition in a mammal comprising administering a therapeutically effective amount of a protegrin peptide polymer conjugate of the invention.

BRIEF DESCRIPTION OF THE DRAWINGS

FIG. PRO2.1. Typical cation exchange purification profile of mono-[mPEG2-CAC-FMOC-40K]-[PG-].

FIG. PRO2.2. SDS-PAGE of purified [mono]-[CAC-PEG2-FOMC-NHS-40K]-[Protegrin-1].

FIG. PRO2.3. Purity analysis of [mono]-[CAC-PEG2-FOMC-40K]-[Protegrin-1] by Reversed Phase HPLC.

FIG. PRO2.4. MALDI-TOF spectrum of purified mono-[CAC-PEG2-FMOC-40K]-[Protegrin-1].

FIG. PRO3.1 Typical cation exchange purification profile of mono-[mPEG-SBC-30K]-[PG-1].

FIG. PRO3.2. SDS-PAGE of purified [mono]-[mPEG-SBC-30K-]-[Protegrin-1].

FIG. PRO3.3. Purity analysis of [mono]-[mPEG-SBC-30K-]-[Protegrin-1] by reversed phase HPLC.

FIG. PRO3.4. MALDI-TOF spectrum of purified [mono]-[mPEG-SBC-30K-]-[Protegrin-1].

FIG. PRO4.1 Typical reversed phase purification profile of [Protegrin-1]-[PEG-di-ButvrAldehyde-5K]-[Protegrin-1].

FIG. PRO4.2. SDS-PAGE of purified [Protegrin-1]-[PEG-di-butyraldehyde-5K]-[Protegrin-1].

FIG. PRO4.3. Purity analysis of [Protegrin-1]-[PEG-di-butyraldehyde-5K]-[Protegrin-1] by reversed phase HPLC.

FIG. PRO4.4. MALDI-TOF spectrum of [Protegrin-1]-[PEG-di-butyraldehyde-5K]-[Protegrin-1].

FIG. PRO5.1. Typical cation-exchange chromatography profile of dextran-butyraldehyde-40K-protegrin-1.

FIG. PRO5.2. SDS-PAGE of purified dextran-butyraldehyde-40K-protegrin-1.

FIG. PRO6.1: PG-1 and $(ALD)_2 2K$ conjugates purification with CM Sepharose FF resin.

FIG. PRO6.2: RP-HPLC analysis of (PG-1)-$(ALD)_2 2K$-(PG-1).

FIG. PRO6.3: MALDI analysis of (PG-1)-$(ALD)_2 2K$-(PG-1).

FIG. PRO7.1.1 and 7.1.2: ALD40K-PG-1 purification with SP Sepharose HP resin.

FIG. PRO7.2. SDS-PAGE of the purified and concentrated ALD40K-PG-1.

FIG. PRO7.3: RP-HPLC analysis of ALD40K-PG-1 (lot #YW-pgALD40K-01).

FIG. PRO7.4: MALDI analysis of ALD40K-PG-1 (lot #YW-pgALD40K-01).

FIG. PRO8.1: CG40K-PG-1 purification with SP Sepharose HP resin.

FIG. PRO8.2: RP-HPLC analysis of purified CG40K-PG-1.

FIG. PRO8.3: MALDI-TOF analysis of purified CG40K-PG-1.

FIG. PRO8.4: SDS-PAGE of purified CG40K-PG-1.

FIG. PRO9.1. Hemolysis relative to the 100% hemolysis produced by 0.25% Triton X-100.

FIG. PRO9.2. Hemolysis by PEG reagent controls.

FIG. PRO9.3. Hemolysis at the maximum concentration.

FIG. PRO9.4. Hemolytic activities of PG-1.

FIG. PRO10.1 and PRO10.2 show the mean plasma concentration-time profiles for CG-$PEG_2$-FMOC-40K-PG-1 and CAC-$PEG_2$-FMOC-40K-PG-1, their corresponding PEG-metabolite and released Protegrin-1.

FIG. PRO10.3 shows the released Protegrin-1 levels after the administration of the two releasable PEG constructs and the level of Protegrin-1 at the same dose.

FIG. PRO10.4 shows the mean plasma concentration-time profiles for $mPEG_2$-PG-1, PG-1 [$PEG_{2k}$-PG-1, PG-1-PEGSk-PG-1.

DETAILED DESCRIPTION

As used in this specification and the intended claims, the singular forms "a." "an," and "the" include plural referents unless the context clearly dictates otherwise. Thus, for example, reference to "a polymer" includes a single polymer as well as two or more of the same or different polymers; reference to "an optional excipient" or to "a pharmaceutically acceptable excipient" refers to a single optional excipient as well as two or more of the same or different optional excipients, and the like.

In describing and claiming one or more embodiments of the present invention, the following terminology will be used in accordance with the definitions described below.

As used herein, the terms "protegrin peptide" and "protegrin peptides" mean one or more peptides having demonstrated or potential use in treating, preventing, or ameliorating one or more diseases, disorders, or conditions in a subject in need thereof, as well as related peptides. These terms may be used to refer to protegrin peptides prior to conjugation to a water-soluble polymer as well as following the conjugation. Protegrin peptides include, but are not limited to, those disclosed herein, including in Table 1. Protegrin peptides include peptides found to have use in treating, preventing, or ameliorating one or more diseases, disorders, or conditions after the time of filing of this application. Related peptides include fragments of protegrin peptides, protegrin peptide variants, and protegrin peptide derivatives that retain some or all of the protegrin activities of the protegrin peptide. As will be known to one of skill in the art, as a general principle, modifications may be made to peptides that do not alter, or only partially abrogate, the properties and activities of those peptides. In some instances, modifications may be made that result in an increase in protegrin activities. Thus, in the spirit of the invention, the terms "protegrin peptide" and "protegrin peptides" are meant to encompass modifications to the protegrin peptides defined and/or disclosed herein that do not alter, only partially abrogate, or increase the protegrin activities of the parent peptide.

TABLE 1

| Name | Sequence ($-NH_2$ indicates amidation at the C-terminal) | SEQ ID NO: |
|---|---|---|
| Protegrin-1 | RGGRLCYCRRRFCVCVGR-NH2 | 1 |
| Protegrin-2 | RGGRLCYCRRRFCICV | 2 |
| Protegrin-3 | RGGGLCYCRRRFCVCVGRG | 3 |
| Protegrin-4 | RGGRLCYCRGWICFCVGRG | 4 |
| Protegrin-5 | RGGRLCYCRPRFCVCVGRG | 5 |
| Preprotegrin | METQRASLCLGRWSLWLLLLGLV VPSASAQALSYREAVLRAVDRLN EQSSEANLYRLLELDQPPKADED PGTPKPVSFTVKETVCPRPTRQP PELCDFKENGRVKQCVGTVTLDQ IKDPLDITCNEVQGVRGGRLCYC RPRFCVCVGRG | 6 |

The term "protegrin activity" as used herein refers to a demonstrated or potential biological activity whose effect is consistent with a desirable protegrin outcome in humans, or to desired effects in non-human mammals or in other species or organisms. A given protegrin peptide may have one or more protegrin activities, however the term "protegrin activities" as used herein may refer to a single protegrin activity or multiple protegrin activities. "protegrin activity" includes the ability to induce a response in vitro, and may be measured in vivo or in vitro. For example, a desirable effect may be assayed in cell culture, or by clinical evaluation, $EC_{50}$ assays. $IC_{50}$ assays, or dose response curves. In vitro or cell culture assays, for example, are commonly available and known to one of skill in the art for many protegrin peptides as defined and/or disclosed herein. Protegrin activity includes treatment, which may be prophylactic or ameliorative, or prevention of a disease, disorder, or condition. Treatment of a disease, disorder or condition can include improvement of a disease, disorder or condition by any amount, including elimination of a disease, disorder or condition.

Protegrin peptides activities may be measured by cell lysis, and cell growth inhibition assays that are known in the art.

As used herein, the terms "peptide," "polypeptide," and "protein," refer to polymers comprised of amino acid monomers linked by amide bonds. Peptides may include the standard 20 α-amino acids that are used in protein synthesis by cells (i.e. natural amino acids), as well as non-natural amino acids (non-natural amino acids nay be found in nature, but not used in protein synthesis by cells, e.g., ornithine, citrulline, and sarcosine, or may be chemically synthesized), amino acid analogs, and peptidomimetics. Spatola, (1983) in Chemistry and Biochemistry of Amino Acids, Peptides, and Proteins, Weinstein, ed., Marcel Dekker, New York, p. 267. The amino acids may be D- or L-optical isomers. Peptides may be formed by a condensation or coupling reaction between the α-carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. Alternatively, the peptides may be non-linear, branched peptides or cyclic peptides. Moreover, the peptides may optionally be modified or protected with a variety of functional groups or protecting groups, including on the amino and/or carboxy terminus.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The terms "protegrin peptide fragment" or "fragments of protegrin peptides" refer to a polypeptide that comprises a truncation at the amino-terminus and/or a truncation at the carboxyl-terminus of a protegrin peptide as defined herein. The terms "protegrin peptide fragment" or "fragments of protegrin peptides" also encompasses amino-terminal and/or carboxyl-terminal truncations of protegrin peptide variants and protegrin peptide derivatives. Protegrin peptide fragments may be produced by synthetic techniques known in the art or may arise from in vivo protease activity on longer peptide sequences. It will be understood that protegrin peptide fragments retain some or all of the protegrin activities of the protegrin peptides.

As used herein, the terms "protegrin peptide variants" or "variants of protegrin peptides" refer to protegrin peptides having one or more amino acid substitutions, including conservative substitutions and non-conservative substitutions, amino acid deletions (either internal deletions and/or C- and/or N-terminal truncations), amino acid additions (either internal additions and/or C- and/or N-terminal additions, e.g., fusion peptides), or any combination thereof. Variants may be naturally occurring (e.g. homologs or orthologs), or non-natural in origin. The term "protegrin peptide variants" may also be used to refer to protegrin peptides incorporating one or more non-natural amino acids, amino acid analogs, and peptidomimetics. It will be understood that, in accordance with the invention, protegrin peptide fragments retain some or all of the protegrin activities of the protegrin peptides.

The terms "protegrin peptide derivatives" or "derivatives of protegrin peptides" as used herein refer to protegrin peptides, protegrin peptide fragments, and protegrin peptide variants that have been chemically altered other than through covalent attachment of a water-soluble polymer. It will be understood that, in accordance with the invention, protegrin peptide derivatives retain some or all of the protegrin activities of the protegrin peptides.

As used herein, the terms "amino terminus protecting group" or "N-terminal protecting group," "carboxy terminus protecting group" or "C-terminal protecting group;" or "side chain protecting group" refer to any chemical moiety capable of addition to and optionally removal from a functional group on a peptide (e.g., the N-terminus, the C-terminus, or a functional group associated with the side chain of an amino acid located within the peptide) to allow for chemical manipulation of the peptide.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "$-(OCH_2CH_2)_n-$" where (n) is 2 to 4000. As used herein, PEG also includes "$-CH_2CH_2-O(CH_2CH_2O)_n-CH_2CH_2-$" and "$-(OCH_2CH_2)_nO-$," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of $-OCH_2CH_2-$ repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or end-point of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n-$ and $CH_3(OCH_2CH_2)_n-$]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidvlcholine, arachidoylphosphatidylcholine, and lecithin.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

"Hydrophilic," e.g., in reference to a "hydrophilic polymer," refers to a polymer that is characterized by its solubility in and compatibility with water. In non-cross linked form, a hydrophilic polymer is able to dissolve in, or be dispersed in water. Typically, a hydrophilic polymer possesses a polymer backbone composed of carbon and hydrogen, and generally possesses a high percentage of oxygen in either the main polymer backbone or in pendent groups substituted along the polymer backbone, thereby leading to its "water-loving" nature. The water-soluble polymers of the present invention are typically hydrophilic. e.g., non-naturally occurring hydrophilic.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, and osmotic pressure) to determine number average molecular weight, or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a polymer segment and a protegrin peptide or an electrophile or nucleophile of a protegrin peptide. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of a protegrin peptide and a water-soluble polymer that can be attached directly or indirectly through a spacer moiety).

A "monomer" or "mono-conjugate," in reference to a polymer conjugate of a protegrin peptide, refers to a protegrin peptide having only one water-soluble polymer molecule covalently attached thereto, whereas a protegrin peptide "dimer" or "di-conjugate" is a polymer conjugate of a protegrin peptide having two water-soluble polymer molecules covalently attached thereto, and so forth.

"Alkyl" refers to a hydrocarbon, typically ranging from about 1 to 15 atoms in length. Such hydrocarbons are preferably but not necessarily saturated and may be branched or straight chain, although typically straight chain is preferred. Exemplary alkyl groups include methyl, ethyl, propyl, butyl, pentyl, 2-methylbutyl. 2-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in for example. "substituted alkyl," refers to a moiety (e.g., an alkyl group) substituted with one or more noninterfering substituents, such as, but not limited to: alkyl; $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, alkenyl, substituted alkenyl, alkynyl, substituted alkynyl, aryl, and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms.

Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

"Releasably attached," e.g., in reference to a protegrin peptide releasably attached to a water-soluble polymer, refers to a protegrin peptide that is covalently attached via a linker that includes a degradable linkage as disclosed herein, wherein upon degradation (e.g., hydrolysis), the protegrin peptide is released. The protegrin peptide thus released will typically correspond to the unmodified parent or native protegrin peptide, or may be slightly altered, e.g., possessing a short organic tag. Preferably, the unmodified parent protegrin peptide is released.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "pharmaceutically acceptable excipient" and "pharmaceutically acceptable carrier" refer to an excipient that may optionally be included in the compositions of the invention and that causes no significant adverse toxicological effects to the patient.

"Pharmacologically effective amount," "physiologically effective amount," and "therapeutically effective amount" are used interchangeably herein to mean the amount of a polymer-(protegrin peptide) conjugate that is needed to provide a desired level of the conjugate (or corresponding unconjugated protegrin peptide) in the bloodstream or in the target tissue. The precise amount will depend upon numerous factors, e.g., the particular protegrin peptide, the components and physical characteristics of the protegrin composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone. A "difunctional" polymer means a polymer having two functional groups contained therein, either the same (i.e., homodifunctional) or different (i.e., heterodifunctional).

The terms "subject." "individual," or "patient" are used interchangeably herein and refer to a vertebrate, preferably a mammal. Mammals include, but are not limited to, murines, rodents, simians, humans, farm animals, sport animals, and pets.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

Unless the context clearly dictates otherwise, when the term "about" precedes a numerical value, the numerical value is understood to mean the stated numerical value and also ±10% of the stated numerical value.

Turning now to one or more aspects of the invention, conjugates are provided, the conjugates comprising a protegrin peptide covalently attached (either directly or through a spacer moiety or linker) to a water-soluble polymer. The conjugates generally have the following formula:

protegrin-[—X-POLY]$_k$ wherein protegrin is a protegrin peptide as defined herein, X is a covalent bond or is a spacer moiety or linker, POLY is a water soluble polymer, and k in an integer ranging from 1-10, preferably 1-5, and more preferably 1-3.

Protegrin Peptides

As previously stated, the conjugates of the invention comprise a protegrin peptide as disclosed and/or defined herein. Protegrin peptides include those currently known to have demonstrated or potential use in treating, preventing, or ameliorating one or more diseases, disorders, or conditions in a subject in need thereof as well as those discovered after the filing of this application. Protegrin peptides also include related peptides.

The protegrin peptides of the invention may comprise any of the 20 natural amino acids, and/or non-natural amino acids, amino acid analogs, and peptidomimetics, in any combination. The peptides may be composed of D-amino acids or L-amino acids, or a combination of both in any proportion. In addition to natural amino acids, the protegrin peptides may contain, or may be modified to include, 1, 2, 3, 4, 5, 6, 7, 8, 9, 10, 15, 20, 25, or more non-natural amino acids. Exemplary non-natural amino acids and amino acid analogs that can be use with the invention include, but are not limited to, 2-aminobutyric acid, 2-aminoisobutyric acid, 3-(1-naphthyl)alanine, 3-(2-naphthyl)alanine, 3-methylhistidine, 3-pyridylalanine, 4-chlorophenylalanine, 4-fluorophenylalanine, 4-hydroxyproline. 5-hydroxylysine, alloisoleucine, citrulline, dehydroalanine, homoarginine, homocysteine, homoserine, hydroxyproline, N-acetylserine, N-formylmethionine. N-methylglycine, N-methylisoleucine, norleucine. N-α-methylarginine, O-phosphoserine, omithine, phenylglycine, pipecolinic acid, piperazic acid, pyroglutamine, sarcosine, valanine, β-alanine, and β-cyclohexylalanine.

The protegrin peptides may be, or may be modified to be, linear, branched, or cyclic, with our without branching.

Additionally, the protegrin peptides may optionally be modified or protected with a variety of functional groups or protecting groups, including amino terminus protecting groups and/or carboxy terminus protecting groups. Protecting groups, and the manner in which they are introduced and removed are described, for example, in "Protective Groups in Organic Chemistry," Plenum Press, London, N. Y. 1973; and Greene et al., "Protective Groups in Organic Synthesis" 3$^{rd}$ Edition, John Wiley and Sons, Inc., New York, 1999. Numerous protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethyl-chroman-6-sulphonyl. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521,184 (issued May 28, 1996).

The protegrin peptides contain, or may be modified to contain, functional groups to which a water-soluble polymer may be attached, either directly or through a spacer moiety or linker. Functional groups include, but are not limited to, the N-terminus of the protegrin peptide, the C-terminus of the protegrin peptide, and any functional groups on the side chain of an amino acid, e.g. lysine, cysteine, histidine, aspartic acid, glutamic acid, tyrosine, arginine, serine, methionine, and threonine, present in the protegrin peptide.

The protegrin peptides can be prepared by any means known in the art, including non-recombinant and recombinant methods, or they may, in some instances, be commercially available. Chemical or non-recombinant methods include, but are not limited to, solid phase peptide synthesis (SPPS), solution phase peptide synthesis, native chemical ligation, intein-mediated protein ligation, and chemical ligation, or a combination thereof. In a preferred embodiment, the protegrin peptides are synthesized using standard SPPS, either manually or by using commercially available automated SPPS synthesizers.

SPPS has been known in the art since the early 1960's (Merrifield, R. B., *J. Am. Chem. Soc.,* 85:2149-2154 (1963)), and is widely employed. (See also, Bodanszky, Principles of Peptide Synthesis, Springer-Verlag, Heidelberg (1984)). There are several known variations on the general approach. (See, for example, "Peptide Synthesis, Structures, and Applications" © 1995 by Academic Press, Chapter 3 and White (2003) *Fmoc Solid Phase Peptide Synthesis, A practical Approach*, Oxford University Press, Oxford). Very briefly, in solid phase peptide synthesis, the desired C-terminal amino acid residue is coupled to a solid support. The subsequent amino acid to be added to the peptide chain is protected on its amino terminus with Boc, Fmoc, or other suitable protecting group, and its carboxy terminus is activated with a standard coupling reagent. The free amino terminus of the support-bound amino acid is allowed to react with the carboxy-terminus of the subsequent amino acid, coupling the two amino acids. The amino terminus of the growing peptide chain is deprotected, and the process is repeated until the desired polypeptide is completed. Side chain protecting groups may be utilized as needed.

Alternatively, the protegrin peptides may be prepared recombinantly. Exemplary recombinant methods used to prepare protegrin peptides include the following, among others, as will be apparent to one skilled in the art. Typically, a protegrin peptide as defined and/or described herein is prepared by constructing the nucleic acid encoding the desired peptide or fragment, cloning the nucleic acid into an expression vector, transforming a host cell (e.g., plant, bacteria such as *Escherichia coli*, yeast such as *Saccharomyces cerevisiae*, or mammalian cell such as Chinese hamster ovary cell or baby hamster kidney cell), and expressing the nucleic acid to produce the desired peptide or fragment. The expression can occur via exogenous expression or via endogenous expression (when the host cell naturally contains the desired genetic coding). Methods for producing and expressing recombinant polypeptides in vitro and in prokaryotic and eukaryotic host cells are known to those of ordinary skill in the art. See, for example, U.S. Pat. No. 4,868,122, and Sambrook et al., Molecular Cloning—A Laboratory Manual (Third Edition), Cold Spring Harbor Laboratory Press (2001).

To facilitate identification and purification of the recombinant peptide, nucleic acid sequences that encode an epitope tag or other affinity binding sequence can be inserted or added in-frame with the coding sequence, thereby producing a fusion peptide comprised of the desired protegrin peptide and a peptide suited for binding. Fusion peptides can be identified and purified by first running a mixture containing the fusion peptide through an affinity column bearing binding moieties (e.g., antibodies) directed against the epitope tag or other binding sequence in the fusion peptide, thereby binding the fusion peptide within the column. Thereafter, the fusion peptide can be recovered by washing the column with the appropriate solution (e.g., acid) to release the bound fusion peptide. Optionally, the tag may subsequently be removed by techniques known in the art. The recombinant peptide can also be identified and purified by lysing the host cells, separating the peptide, e.g., by size exclusion chromatography, and collecting the peptide. These and other methods for identifying and purifying recombinant peptides are known to those of ordinary skill in the art.

Related Peptides

It will be appreciated and understood by one of skill in the art that certain modifications can be made to the protegrin peptides defined and/or disclosed herein that do not alter, or only partially abrogate, the properties and activities of these protegrin peptides. In some instances, modifications may be made that result in an increase in protegrin activities. Additionally, modifications may be made that increase certain biological and chemical properties of the protegrin peptides in a beneficial way, e.g. increased in vivo half life, increased stability, decreased susceptibility to proteolytic cleavage, etc. Thus, in the spirit and scope of the invention, the term "protegrin peptide" is used herein in a manner to include not only the protegrin peptides defined and/or disclosed herein, but also related peptides, i.e. peptides that contain one or more modifications relative to the protegrin peptides defined and/or disclosed herein, wherein the modification(s) do not alter, only partially abrogate, or increase the protegrin activities as compared to the parent peptide.

Related peptides include, but are not limited to, fragments of protegrin peptides, protegrin peptide variants, and protegrin peptide derivatives. Related peptides also include any and all combinations of these modifications. In a non-limiting example, a related peptide may be a fragment of a protegrin peptide as disclosed herein having one or more amino acid substitutions. Thus it will be understood that any reference to a particular type of related peptide is not limited to a protegrin peptide having only that particular modification, but rather encompasses a protegrin peptide having that particular modification and optionally any other modification.

Related peptides may be prepared by action on a parent peptide or a parent protein (e.g. proteolytic digestion to generate fragments) or through de novo preparation (e.g. solid phase synthesis of a peptide having a conservative amino acid substitution relative to the parent peptide). Related peptides may arise by natural processes (e.g. processing and other post-translational modifications) or may be made by chemical modification techniques. Such modifications are well-known to those of skill in the art.

A related peptide may have a single alteration or multiple alterations relative to the parent peptide. Where multiple alterations are present, the alterations may be of the same type or a given related peptide may contain different types of modifications. Furthermore, modifications can occur anywhere in a polypeptide, including the peptide backbone, the amino acid side-chains, and the N- or C-termini.

As previously noted, related peptides include fragments of the protegrin peptides defined and/or disclosed herein, wherein the fragment retains some of or all of at least one protegrin activity of the parent peptide. The fragment may also exhibit an increase in at least one protegrin activity of the parent peptide. In certain embodiments of the invention, protegrin peptides include related peptides having at least 2, 3, 4, 5, 6, 7, 8, 9, 10, 11, 12, 13, 14, 15, 20, 25, 30, 35, 40, 45, 50, 60, 70, 80, 90, or 100 contiguous amino acid residues, or more than 125 contiguous amino acid residues, of any of the protegrin peptides disclosed, herein, including in Table 1. In other embodiments of the invention, protegrin peptides include related peptides having 0, 1, 2, 3, 4, 5, 6, 7, 8, 9, 10, 15, 20, 25, 30, 35, 40, 45, or 50 amino acid residues deleted from the N-terminus and/or having 0, 1, 2, 3, 4, 5, 6, 7, 8, 9, 10, 15, 20, 25, 30, 35, 40, 45, or 50 amino acid residues deleted from the C-terminus of any of the protegrin peptides disclosed herein, including in Table 1.

Related peptides also include variants of the protegrin peptides defined and/or disclosed herein, wherein the variant retains some of or all of at least one protegrin activity of the parent peptide. The variant may also exhibit an increase in at least one protegrin activity of the parent peptide. In certain embodiments of the invention, protegrin peptides include variants having 1, 2, 3, 4, 5, 6, 7, 8, 9, 10, 15, 20, 25, 30, 35, 40, 45, or 50 conservative and/or non-conservative amino acid substitutions relative to the protegrin peptides disclosed herein, including in Table 1. Desired amino acid substitutions, whether conservative or non-conservative, can be determined by those skilled in the art.

In certain embodiments of the invention, protegrin peptides include variants having conservative amino substitutions; these substitutions will produce a protegrin peptide having functional and chemical characteristics similar to those of the parent peptide. In other embodiments, protegrin peptides include variants having non-conservative amino substitutions; these substitutions will produce a protegrin peptide having functional and chemical characteristics that may differ substantially from those of the parent peptide. In certain embodiments of the invention, protegrin peptide variants have both conservative and non-conservative amino acid substitutions. In other embodiments, each amino acid residue may be substituted with alanine.

Natural amino acids may be divided into classes based on common side chain properties: nonpolar (Gly, Ala, Val, Leu, Ile, Met); polar neutral (Cys. Ser, Thr, Pro, Asn, Gln); acidic (Asp, Glu); basic (His, Lys, Arg); and aromatic (Trp, Tyr, Phe). By way of example, non-conservative amino acid substitutions may involve the substitution of an amino acid of one class for that of another, and may be introduced in regions of the peptide not critical for protegrin activity.

Preferably, amino acid substitutions are conservative. Conservative amino acid substitutions may involve the substitution of an amino acid of one class for that of the same class. Conservative amino acid substitutions may also encompass non-natural amino acid residues, including peptidomimetics and other atypical forms of amino acid moieties, and may be incorporated through chemical peptide synthesis.

Amino acid substitutions may be made with consideration to the hydropathic index of amino acids. The importance of the hydropathic amino acid index in conferring interactive biological function on a protein is generally understood in the art (Kyte et al., 1982, *J. Mol. Biol.* 157:105-31). Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its biological properties. According to U.S. Pat. No. 4,554,101, incorporated herein by reference, the following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred.

In certain embodiments of the invention, protegrin peptides include variants having 1, 2, 3, 4, 5, 6, 7, 8, 9, 10, 15, 20, 25, 30, 35, 40, 45, or 50 amino acid deletions relative to the protegrin peptides disclosed herein, including in Table 1. The deleted amino acid(s) may be at the N- or C-terminus of the peptide, at both termini, at an internal location or locations within the peptide, or both internally and at one or both termini. Where the variant has more than one amino acid deletion, the deletions may be of contiguous amino acids or of amino acids at different locations within the primary amino acid sequence of the parent peptide.

In other embodiments of the invention, protegrin peptides include variants having 1, 2, 3, 4, 5, 6, 7, 8, 9, 10, 15, 20, 25, 30, 35, 40, 45, or 50 amino acid additions relative to the protegrin peptides disclosed herein, including in Table 1. The added amino acid(s) may be at the N- or C-terminus of the peptide, at both termini, at an internal location or locations within the peptide, or both internally and at one or both termini. Where the variant has more than one amino acid addition, the amino acids may be added contiguously, or the amino acids may be added at different locations within the primary amino acid sequence of the parent peptide.

Addition variants also include fusion peptides. Fusions can be made either at the N-terminus or at the C-terminus of the protegrin peptides disclosed herein, including in Table 1. In certain embodiments, the fusion peptides have 1, 2, 3, 4, 5, 6, 7, 8, 9, 10, 15, 20, 25, 30, 35, 40, 45, or 50 amino acid additions relative to the protegrin peptides disclosed herein, including in Table 1. Fusions may be attached directly to the protegrin peptide with no connector molecule or may be through a connector molecule. As used in this context, a connector molecule may be an atom or a collection of atoms optionally used to link a protegrin peptide to another peptide. Alternatively, the connector may be an amino acid sequence designed for cleavage by a protease to allow for the separation of the fused peptides.

The protegrin peptides of the invention may be fused to peptides designed to improve certain qualities of the protegrin peptide, such as protegrin activity, circulation time, or reduced aggregation. Protegrin peptides may be fused to an immunologically active domain, e.g. an antibody epitope, to facilitate purification of the peptide, or to increase the in vivo half life of the peptide. Additionally, protegrin peptides may be fused to known functional domains, cellular localization sequences, or peptide permeant motifs known to improve membrane transfer properties.

In certain embodiments of the invention, protegrin peptides also include variants incorporating one or more non-natural amino acids, amino acid analogs, and peptidomimetics. Thus the present invention encompasses compounds structurally similar to the protegrin peptides defined and/or disclosed herein, which are formulated to mimic the key portions of the protegrin peptides of the present invention. Such compounds may be used in the same manner as the protegrin peptides of the invention. Certain mimetics that mimic elements of protein secondary and tertiary structure have been previously described. Johnson et al., Biotechnology and Pharmacy, Pezzuto et al. (Eds.), Chapman and Hall, NY, 1993. The underlying rationale behind the use of peptide mimetics is that the peptide backbone of proteins exists chiefly to orient amino acid side chains in such a way as to facilitate molecular interactions. A peptide mimetic is thus designed to permit molecular interactions similar to the parent peptide. Mimetics can be constructed to achieve a similar spatial orientation of the essential elements of the amino acid side chains. Methods for generating specific structures have been disclosed in the art. For example, U.S. Pat. Nos. 5,446,128, 5,710,245, 5,840,833, 5,859,184, 5,440,013; 5,618,914, 5,670,155, 5,475,085, 5,929,237, 5,672,681 and 5,674,976, the contents of which are hereby incorporated by reference, all disclose peptidomimetics structures that may have improved properties over the parent peptide, for example they may be conformationally restricted, be more thermally stable, exhibit increased resistance to degredation, etc.

In another embodiment, related peptides comprise or consist of a peptide sequence that is at least 70% identical to any of the protegrin peptides disclosed herein, including in Table 1. In additional embodiments, related peptides are at least 75% identical, at least 80% identical, at least 85% identical, 90% identical, at least 91% identical, at least 92% identical, 93% identical, at least 94% identical, at least 95% identical, 96% identical, at least 97% identical, at least 98% identical, or at least 99% identical to any of the protegrin peptides disclosed herein, including in Table 1.

Sequence identity (also known as % homology) of related polypeptides can be readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1. A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988*, SIAM J. Applied Math.,* 48:1073.

Preferred methods to determine sequence identity and/or similarity are designed to give the largest match between the sequences tested. Methods to determine sequence identity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)). The particular choices to be made with regard to algorithms, gap opening penalties, gap extension penalties, comparison matrices, and thresholds of similarity will be readily apparent to those of skill in the art and will depend on the specific comparison to be made.

Related peptides also include derivatives of the protegrin peptides defined and/or disclosed herein, wherein the variant retains some of or all of at least one protegrin activity of the parent peptide. The derivative may also exhibit an increase in at least one protegrin activity of the parent peptide. Chemical alterations of protegrin peptide derivatives include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. (See, for instance, T. E. Creighton, Proteins, Structure and Molecular Properties, 2nd ed., W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-46 (1990); Rattan et al., Ann. N.Y. Acad. Sci. 663:48-62, 1992).

Protegrin peptide derivatives also include molecules formed by the deletion of one or more chemical groups from the parent peptide. Methods for preparing chemically modified derivatives of the protegrin peptides defined and/or disclosed herein are known to one of skill in the art.

In some embodiments of the invention, the protegrin peptides may be modified with one or more methyl or other lower alkyl groups at one or more positions of the protegrin peptide sequence. Examples of such groups include methyl, ethyl, propyl, isopropyl, butyl, isobutyl, pentyl, etc. In certain preferred embodiments, arginine, lysine, and histidine residues of the protegrin peptides are modified with methyl or other lower alkyl groups.

In other embodiments of the invention, the protegrin peptides may be modified with one or more glycoside moieties relative to the parent peptide. Although any glycoside can be used, in certain preferred embodiments the protegrin peptide is modified by introduction of a monosaccharide, a disaccharide, or a trisaccharide or it may contain a glycosylation sequence found in natural peptides or proteins in any mammal. The saccharide may be introduced at any position, and more than one glycoside may be introduced. Glycosylation may occur on a naturally occurring amino acid residue in the protegrin peptide, or alternatively, an amino acid may be substituted with another for modification with the saccharide.

Glycosylated protegrin peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the protegrin peptide polymer conjugates may be conjugated in vitro. The glycosylation may occur before deprotection. Preparation of aminoacid glycosides is described in U.S. Pat. No. 5,767,254, WO 2005/097158, and Doores, K., et al., *Chem. Commun.*, 1401-1403, 2006, which are incorporated herein by reference in their entireties. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated protegrin peptide conjugate made by stepwise solid phase peptide synthesis involving contacting a growing peptide chain with protected amino acids in a stepwise manner, wherein at least one of the protected amino acids is glycosylated, followed by water-soluble polymer conjugation, may have a purity of at least 95%, such as at least 97%, or at least 98%, of a single species of the glycosylated and conjugated protegrin peptide.

Monosaccharides that may by used for introduction at one or more amino acid residues of the protegrin peptides defined and/or disclosed herein include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetylneuraminic acid, fucose, N-Acetylgalactosamine, and N-Acetylglucosamine, as well as others. Glycosides, such as mono-, di-, and trisaccharides for use in modifying a protegrin peptide, may be naturally occurring or may be synthetic. Disaccharides that may by used for introduction at one or more amino acid residues of the protegrin peptides defined and/or disclosed herein include sucrose, lactose, maltose, trehalose, melibiose, and cellobiose, among others. Trisaccharides include acarbose, raffinose, and melezitose.

In further embodiments of the invention, the protegrin peptides defined and/or disclosed herein may be chemically coupled to biotin. The biotin/therapeutic peptide molecules can then to bind to avidin.

As previously noted, modifications may be made to the protegrin peptides defined and/or disclosed herein that do not alter, or only partially abrogate, the properties and activities of these protegrin peptides. In some instances, modifications may be made that result in an increase in protegrin activity. Thus, included in the scope of the invention are modifications to the protegrin peptides disclosed herein, including in Table 1, that retain at least 1%, at least 5%, at least 10%, at least 20%, at least 30%, at least 40%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and any range derivable therein, such as, for example, at least 70% to at least 80%, and more preferably at least 81% to at least 90%; or even more preferably, between at least 91% and at least 99% of the protegrin activity relative to the unmodified protegrin peptide. Also included in the scope of the invention are modification to the protegrin peptides disclosed herein, including in Table 1, that have greater than 100%, greater than 110%, greater than 125%, greater than 150%, greater than 200%, or greater than 300%, or greater than 10-fold or greater than 100-fold, and any range derivable therein, of the protegrin activity relative to the unmodified protegrin peptide.

The level of protegrin activity of a given protegrin peptide, or a modified protegrin peptide, may be determined by any suitable in vivo or in vitro assay. For example, protegrin activity may be assayed in cell culture, or by clinical evaluation, $EC_{50}$ assays, $IC_{50}$ assays, or dose response curves. In vitro or cell culture assays, for example, are commonly available and known to one of skill in the art for many protegrin peptides as disclosed herein, including in Table 1. It will be understood by one of skill in the art that the percent activity of a modified protegrin peptide relative to its unmodified parent can be readily ascertained through a comparison of the activity of each as determined through the assays disclosed herein or as known to one of skill in the art.

One of skill in the art will be able to determine appropriate modifications to the protegrin peptides defined and/or disclosed herein, including those disclosed herein, including in Table 1. For identifying suitable areas of the protegrin peptides that may be changed without abrogating their protegrin activities, one of skill in the art may target areas not believed to be essential for activity. For example, when similar peptides with comparable activities exist from the same species or across other species, one of skill in the art may compare those amino acid sequences to identify residues that are conserved among similar peptides. It will be understood that changes in areas of a protegrin peptide that are not conserved relative to similar peptides would be less likely to adversely affect the therapeutic activity. One skilled in the art would also know that, even in relatively conserved regions, one may substitute chemically similar amino acids while retaining protegrin activity. Therefore, even areas that may be important for biological activity and/or for structure may be subject to amino acid substitutions without destroying the protegrin activity or without adversely affecting the peptide structure.

Additionally, as appropriate, one of skill in the art can review structure-function studies identifying residues in similar peptides that are important for activity or structure. In view of such a comparison, one can predict the importance of an amino acid residue in a protegrin peptide that corresponds to an amino acid residue that is important for activity or structure in similar peptides. One of skill in the art may opt for amino acid substitutions within the same class of amino acids for such predicted important amino acid residues of the protegrin peptides.

Also, as appropriate, one of skill in the art can also analyze the three-dimensional structure and amino acid sequence in relation to that structure in similar peptides. In view of such information, one of skill in the art may predict the alignment of amino acid residues of a protegrin peptide with respect to its three dimensional structure. One of skill in the art may choose not to make significant changes to amino acid residues predicted to be on the surface of the peptide, since such residues may be involved in important interactions with other molecules. Moreover, one of skill in the art may generate variants containing a single amino acid substitution at each amino acid residue for test purposes. The variants could be screened using protegrin activity assays known to those with skill in the art. Such variants could be used to gather information about suitable modifications. For example, where a change to a particular amino acid residue resulted in abrogated, undesirably reduced, or unsuitable activity, variants with such a modification would be avoided. In other words, based on information gathered from routine experimentation, one of skill in the art can readily determine the amino acids where further modifications should be avoided either alone or in combination with other modifications.

One of skill in the art may also select suitable modifications based on secondary structure predication. A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978. *Adv. Enzymol. Relat. Areas Mol. Biol.* 47:45-48: Chou et al., 1978, *Ann. Rev. Biochem.* 47:251-276; and Chou et al., 1979, *Biophys.,* 26:367-84. Moreover, computer programs are currently available to assist with predicting secondary structure. One method of predicting secondary structure is based upon homology modeling. For example, two peptides or proteins which have a sequence identity of greater than 30%, or similarity greater than 40%, often have similar structural topologies. Recent growth of the protein structural database (PDB, http://www.rcsb.org/pdb/home/home.do) has provided enhanced predictability of secondary, tertiary, and quarternary structure, including the potential number of folds within the structure of a peptide or protein. See Holm et al., 1999, *Nucleic Acids Res.* 27:244-47. It has been suggested that there are a limited number of folds in a given peptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Protegrin Peptide Conjugates

As described above, a conjugate of the invention comprises a water-soluble polymer covalently attached (either directly or through a spacer moiety or linker) to a protegrin peptide. Typically, for any given conjugate, there will be about one to five water-soluble polymers covalently attached to a protegrin peptide (wherein for each water-soluble polymer, the water-soluble polymer can be attached either directly to the protegrin peptide or through a spacer moiety).

To elaborate, a protegrin peptide conjugate of the invention typically has about 1, 2, 3, or 4 water-soluble polymers individually attached to a protegrin peptide. That is to say, in certain embodiments, a conjugate of the invention will possess about 4 water-soluble polymers individually attached to a protegrin peptide, or about 3 water-soluble polymers individually attached to a protegrin peptide, or about 2 water-soluble polymers individually attached to a protegrin peptide, or about 1 water-soluble polymer attached to a protegrin peptide. The structure of each of the water-soluble polymers attached to the protegrin peptide may be the same or different. One protegrin peptide conjugate in accordance with the invention is one having a water-soluble polymer releasably attached to the protegrin peptide, particularly at the N-terminus of the protegrin peptide. Another protegrin peptide conjugate in accordance with the invention is one having a water-soluble polymer stably attached to the protegrin peptide, particularly at the N-terminus of the protegrin peptide. Another protegrin peptide conjugate is one having a water-soluble polymer releasably attached to the protegrin peptide, particularly at the C-terminus of the protegrin peptide. Another protegrin peptide conjugate in accordance with the invention is one having a water-soluble polymer stably attached to the protegrin peptide, particularly at the C-terminus of the protegrin peptide. Other protegrin peptide conjugates in accordance with the invention are those having a water-soluble polymer releasably or stably attached to an amino acid within the protegrin peptide. Additional water-soluble polymers may be releasably or stably attached to other sites on the protegrin peptide, e.g., such as one or more additional sites. For example, a protegrin peptide conjugate having a water-soluble polymer releasably attached to the N-terminus may additionally possess a water-soluble polymer stably attached to a lysine residue. In one embodiment, one or more amino acids may be inserted, at the N- or C-terminus, or within the peptide to releasably or stably attach a water soluble polymer. One preferred embodiment of the present invention is a mono-protegrin peptide polymer conjugate, i.e., a protegrin peptide having one water-soluble polymer covalently attached thereto. In an even more preferred embodiment, the water-soluble polymer is one that is attached to the protegrin peptide at its N-terminus.

In another embodiment of the invention, a protegrin peptide polymer conjugate of the invention is absent a metal ion, i.e., the protegrin peptide is not chelated to a metal ion.

For the protegrin peptide polymer conjugates described herein, the protegrin peptide may optionally possess one or more N-methyl substituents. Alternatively, for the protegrin peptide polymer conjugates described herein, the protegrin peptide may be glycosylated, e.g., having a mono- or disaccharide, or naturally-occurring amino acid glycosylation covalently attached to one or more sites thereof.

As discussed herein, the compounds of the present invention may be made by various methods and techniques known and available to those skilled in the art.

The Water-Soluble Polymer

A conjugate of the invention comprises a protegrin peptide attached, stably or releasably, to a water-soluble polymer. The water-soluble polymer is typically hydrophilic, nonpeptidic, and biocompatible. A substance is considered biocompatible if the beneficial effects associated with use of the substance alone or with another substance (e.g., an active agent such a protegrin peptide) in connection with living tissues (e.g., administration to a patient) outweighs any deleterious effects as evaluated by a clinician, e.g., a physician. A substance is considered nonimmunogenic if the intended use of the substance in vivo does not produce an undesired immune response (e.g., the formation of antibodies) or, if an immune response is produced, that such a response is not deemed clinically significant or important as evaluated by a clinician. Typically, the water-soluble polymer is hydrophilic, biocompatible and nonimmunogenic.

Further the water-soluble polymer is typically characterized as having from 2 to about 300 termini, preferably from 2 to 100 termini, and more preferably from about 2 to 50 termini. Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing, including copolymers and terpolymers thereof.

The water-soluble polymer is not limited to a particular structure and may possess a linear architecture (e.g., alkoxy PEG or bifunctional PEG), or a non-linear architecture, such as branched, forked, multi-armed (e.g., PEGs attached to a polyol core), or dendritic (i.e. having a densely branched structure with numerous end groups). Moreover, the polymer subunits can be organized in any number of different patterns and can be selected, e.g., from homopolymer, alternating copolymer, random copolymer, block copolymer, alternating tripolymer, random tripolymer, and block tripolymer.

One particularly preferred type of water-soluble polymer is a polyalkylene oxide, and in particular, polyethylene glycol (or PEG). Generally, a PEG used to prepare a protegrin peptide polymer conjugate of the invention is "activated" or reactive. That is to say, the activated PEG (and other activated water-soluble polymers collectively referred to herein as "polymeric reagents") used to form a protegrin peptide conjugate comprises an activated functional group suitable for coupling to a desired site or sites on the protegrin peptide. Thus, a polymeric reagent for use in preparing a protegrin peptide conjugate includes a functional group for reaction with the protegrin peptide.

Representative polymeric reagents and methods for conjugating such polymers to an active moiety are known in the art, and are, e.g., described in Harris, J. M. and Zalipsky, S., eds, *Poly(ethylene glycol). Chemistry and Biological Applications*, ACS, Washington, 1997; Veronese, F., and J. M Harris, eds., *Peptide and Protein PEGylation*, Advanced Drug Delivery Reviews, 54(4); 453-609 (2002). Zalipsky, S., et al., "*Use of Functionalized Poly(Ethylene Glycols) for Modification of Polypeptides*" in *Polyethylene Glycol Chemistry: Biotechnical and Biomedical Applications*. J. M. Harris, ed., Plenus Press, New York (1992); Zalipsky (1995) *Advanced Drug Reviews* 16:157-182, and in Roberts, et al., *Adv. Drug Delivery Reviews*. 54, 459-476 (2002).

Additional PEG reagents suitable for use in forming a conjugate of the invention, and methods of conjugation are described in the Pasut. G., et al., *Expert Opin. Ther. Patents* (2004), 14(5). PEG reagents suitable for use in the present invention also include those available from NOF Corporation, as described generally on the NOF website (http://nofamerica.net/store/). Products listed therein and their chemical structures are expressly incorporated herein by reference. Additional PEGs for use in forming a protegrin peptide conjugate of the invention include those available from Polypure (Norway) and from QuantaBioDesign LTD (Ohio), where the contents of their catalogs with respect to available PEG reagents are expressly incorporated herein by reference. In addition, water soluble polymer reagents useful for preparing peptide conjugates of the invention can be prepared synthetically. Descriptions of the water soluble polymer reagent synthesis can be found in, for example, U.S. Pat. Nos. 5,252,714, 5,650,234, 5,739,208, 5,932,462, 5,629,384, 5,672.662, 5,990.237, 6,448.369, 6,362.254, 6,495,659, 6,413,507, 6,376,604, 6,348,558, 6,602,498, and 7,026,440.

Typically, the weight-average molecular weight of the water-soluble polymer in the conjugate is from about 100 Daltons to about 150,000) Daltons. Exemplary ranges include weight-average molecular weights in the range of from about 250 Daltons to about 80,000 Daltons, from 500 Daltons to about 80,000 Daltons, from about 500 Daltons to about 65,000 Daltons, from about 500 Daltons to about 40,000 Daltons, from about 750 Daltons to about 40,000 Daltons, from about 1000 Daltons to about 30,000 Daltons. In a preferred embodiment, the weight average molecular weight of the water-soluble polymer in the conjugate ranges from about 1000 Daltons to about 10,000 Daltons. In certain other preferred embodiments, the range is from about 1000 Daltons to about 5000) Daltons, from about 5000 Daltons to about 10,000 Daltons, from about 2500 Daltons to about 7500 Daltons, from about 1000 Daltons to about 3000 Daltons, from about 3000 Daltons to about 7000 Daltons, or from about 7000 Daltons to about 10,000 Daltons. In a further preferred embodiment, the weight average molecular weight of the water-soluble polymer in the conjugate ranges from about 20.000 Daltons to about 40.000 Daltons. In other preferred embodiments, the range is from about 20,000 Daltons to about 30,000 Daltons, from about 30,000 Daltons to about 40,000 Daltons, from about 25,000 Daltons to about 35,000 Daltons, from about 20,000 Daltons to about 26,000 Daltons, from about 26,000 Daltons to about 34.000 Daltons, or from about 34,000 Daltons to about 40,000 Daltons.

For any given water-soluble polymer, a molecular weight in one or more of these ranges is typical. Generally, a protegrin peptide conjugate in accordance with the invention, when intended for subcutaneous or intravenous administration, will comprise a PEG or other suitable water-soluble polymer having a weight average molecular weight of about 20,000 Daltons or greater, while a protegrin peptide conjugate intended for pulmonary administration will generally, although not necessarily, comprise a PEG polymer having a weight average molecular weight of about 20,000 Daltons or less.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1.500 Daltons, about 2,000 Daltons, about 2,200 Daltons, about 2,500 Daltons, about 3,000 Daltons, about 4,000 Daltons, about 4,400 Daltons, about 4,500 Daltons, about 5.000 Daltons, about 5.500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25.000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons.

Branched versions of the water-soluble polymer (e.g., a branched 40,000 Dalton water-soluble polymer comprised of two 20,000 Dalton polymers or the like) having a total molecular weight of any of the foregoing can also be used. In one or more particular embodiments, depending upon the other features of the subject protegrin peptide polymer conjugate, the conjugate is one that does not have one or more attached PEG moieties having a weight-average molecular weight of less than about 6,000 Daltons.

In instances in which the water-soluble polymer is a PEG, the PEG will typically comprise a number of $(OCH_2CH_2)$ monomers. As used herein, the number of repeat units is typically identified by the subscript "n" in, for example, "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1.200 to about 1,900. Preferred ranges of n include from about 10 to about 700, and from about 10 to about 1800. For any given polymer in which the molecular weight is known, it is possible to determine the number of repeating units (i.e., "n") by dividing the total weight-average molecular weight of the polymer by the molecular weight of the repeating monomer.

With regard to the molecular weight of the water-soluble polymer, in one or more embodiments of the invention, depending upon the other features of the particular protegrin peptide conjugate, the conjugate comprises a protegrin peptide covalently attached to a water-soluble polymer having a molecular weight greater than about 2,000 Daltons.

A polymer for use in the invention may be end-capped, that is, a polymer having at least one terminus capped with a relatively inert group, such as a lower alkoxy group (i.e., a $C_{1-6}$alkoxy group) or a hydroxyl group. One frequently employed end-capped polymer is methoxy-PEG (commonly referred to as mPEG), wherein one terminus of the polymer is a methoxy ($—OCH_3$) group. The -PEG-symbol used in the foregoing generally represents the following structural unit: $—CH_2CH_2O—(CH_2CH_2O)_n—CH_2CH_2—$, where (n) generally ranges from about zero to about 4,000.

Multi-armed or branched PEG molecules, such as those described in U.S. Pat. No. 5,932,462, are also suitable for use in the present invention. For example, the PEG may be described generally according to the structure:

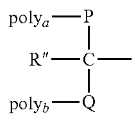

where $poly_a$ and $poly_b$ are PEG backbones (either the same or different), such as methoxy poly(ethylene glycol); R" is a non-reactive moiety, such as H, methyl or a PEG backbone; and P and Q are non-reactive linkages. In one embodiment, the branched PEG molecule is one that includes a lysine residue, such as the following reactive PEG suitable for use in forming a protegrin peptide conjugate. Although the branched PEG below is shown with a reactive succinimidyl group, this represents only one of a myriad of reactive functional groups suitable for reacting with a protegrin peptide.

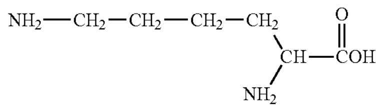

Lysine

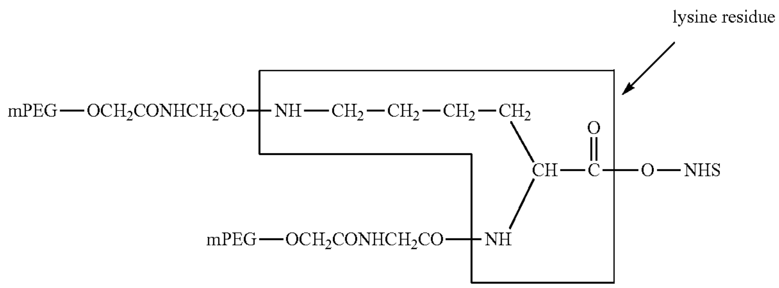

Branched mPEG Succinimidyl Derivative

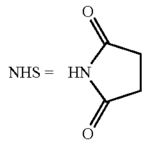

In some instances, the polymeric reagent (as well as the corresponding conjugate prepared from the polymeric reagent) may lack a lysine residue in which the polymeric portions are connected to amine groups of the lysine via a "—$OCH_2CONHCH_2CO$—" group. In still other instances, the polymeric reagent (as well as the corresponding conjugate prepared from the polymeric reagent) may lack a branched water-soluble polymer that includes a lysine residue (wherein the lysine residue is used to effect branching).

Additional branched-PEGs for use in forming a protegrin peptide conjugate of the present invention include those described in co-owned U.S. Patent Application Publication No. 2005/0009988. Representative branched polymers described therein include those having the following generalized structure:

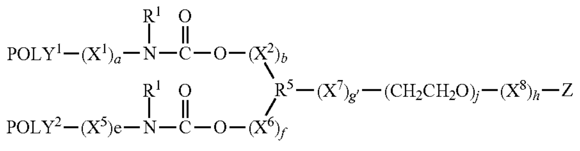

where $POLY^1$ is a water-soluble polymer: $POLY^2$ is a water-soluble polymer: (a) is 0, 1, 2 or 3; (b) is 0, 1, 2 or 3; (e) is 0, 1, 2 or 3; (f') is 0, 1, 2 or 3; (g') is 0, 1, 2 or 3; (h) is 0, 1, 2 or 3; (j) is 0 to 20; each $R^1$ is independently H or an organic radical selected from alkyl, substituted alkyl, alkenyl, substituted alkenyl, alkynyl, substituted alkynyl, aryl and substituted aryl; $X^1$, when present, is a spacer moiety; $X^2$, when present, is a spacer moiety; $X^5$, when present, is a spacer moiety; $X^6$, when present, is a spacer moiety; $X^7$, when present, is a spacer moiety; $X^8$, when present, is a spacer moiety; $R^5$ is a branching moiety; and Z is a reactive group for coupling to a protegrin peptide, optionally via an intervening spacer. $POLY^1$ and $POLY^2$ in the preceding branched polymer structure may be different or identical, i.e., are of the same polymer type (structure) and molecular weight.

A preferred branched polymer falling into the above classification suitable for use in the present invention is:

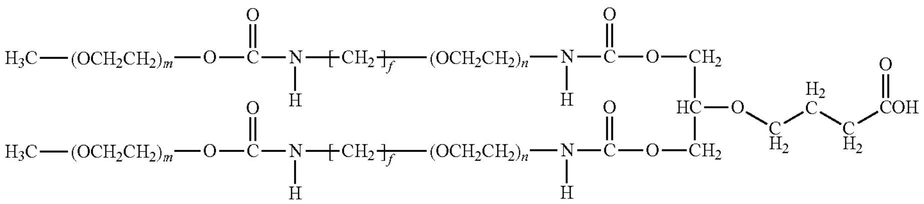

where (m) is 2 to 4000, and (f) is 0 to 6 and (n) is 0 to 20.

Branched polymers suitable for preparing a conjugate of the invention also include those represented more generally by the formula $R(POLY)_y$, where R is a central or core molecule from which extends 2 or more POLY arms such as PEG. The variable y represents the number of POLY arms, where each of the polymer arms can independently be end-capped or alternatively, possess a reactive functional group at its terminus. A more explicit structure in accordance with this embodiment of the invention possesses the structure, $R(POLY\text{-}Z)_y$, where each Z is independently an end-capping group or a reactive group, e.g., suitable for reaction with a protegrin peptide. In yet a further embodiment when Z is a reactive group, upon reaction with a protegrin peptide, the resulting linkage can be hydrolytically stable, or alternatively, may be degradable, i.e., hydrolyzable. Typically, at least one polymer arm possesses a terminal functional group suitable for reaction with, e.g., a protegrin peptide. Branched PEGs such as those represented generally by the formula, $R(PEG)_y$ above possess 2 polymer arms to about 300 polymer arms (i.e., n ranges from 2 to about 300). Preferably, such branched PEGs typically possess from 2 to about 25 polymer arms, such as from 2 to about 20 polymer arms, from 2 to about 15 polymer arms, or from 3 to about 15 polymer arms. Multi-armed polymers include those having 3, 4, 5, 6, 7 or 8 arms.

Core molecules in branched PEGs as described above include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane.

As will be described in more detail in the linker section below, although any of a number of linkages can be used to covalently attach a polymer to a protegrin peptide, in certain instances, the linkage is degradable, designated herein as $L_D$, that is to say, contains at least one bond or moiety that hydrolyzes under physiological conditions, e.g., an ester, hydrolyzable carbamate, carbonate, or other such group. In other instances, the linkage is hydrolytically stable.

Illustrative multi-armed PEGs having 3 arms, 4 arms, and 8 arms are known and are available commercially and/or can be prepared following techniques known to those skilled in the art. Multi-armed activated polymers for use in the method of the invention include those corresponding to the following structure, where E represents a reactive group suitable for reaction with a reactive group on the protegrin peptide. In one or more embodiments, E is an —OH (for reaction with a protegrin peptide carboxy group or equivalent), a carboxylic acid or equivalent (such as an active ester), a carbonic acid (for reaction with protegrin peptide —OH groups), or an amino group.

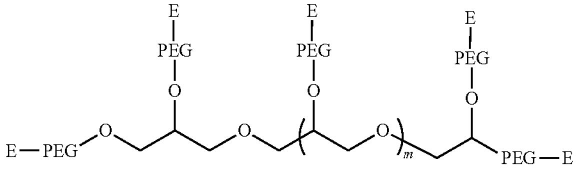

In the structure above, PEG is $-(CH_2CH_2O)_nCH_2CH_2-$, and m is selected from 3, 4, 5, 6, 7, and 8. In certain embodiments, typical linkages are ester, carboxyl and hydrolyzable carbamate, such that the polymer-portion of the conjugate is hydrolyzed in vivo to release the protegrin peptide from the intact polymer conjugate. In such instances, the linker L is designated as $L_D$.

Alternatively, the polymer may possess an overall forked structure as described in U.S. Pat. No. 6,362,254. This type of polymer segment is useful for reaction with two protegrin peptide moieties, where the two protegrin peptide moieties are positioned a precise or predetermined distance apart.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable (i.e., releasable) linkages include but are not limited to ester, carbonate ester, carbamate, sulfate, phosphate, acyloxyalkyl ether, acetal, and ketal. Such linkages when contained in a given polymer segment will often be stable upon storage and upon initial administration.

The PEG polymer used to prepare a protegrin peptide polymer conjugate may comprise a pendant PEG molecule having reactive groups, such as carboxyl or amino, covalently attached along the length of the PEG rather than at the end of the PEG chain(s). The pendant reactive groups can be attached to the PEG directly or through a spacer moiety, such as an alkylene group.

In certain embodiments, a protegrin peptide polymer conjugate according to one aspect of the invention is one comprising a protegrin peptide releasably attached, preferably at its N-terminus, to a water-soluble polymer. Hydrolytically degradable linkages, useful not only as a degradable linkage within a polymer backbone, but also, in the case of certain embodiments of the invention, for covalently attaching a water-soluble polymer to a protegrin peptide, include: carbonate; imine resulting, for example, from reaction of an amine and an aldehyde (see, e.g., Ouchi et al. (1997) *Polymer Preprints* 38(1):582-3): phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and esters, and certain urethane (carbamate) linkages.

Illustrative PEG reagents for use in preparing a releasable protegrin peptide conjugate in accordance with the invention are described in U.S. Pat. Nos. 6,348,558, 5,612,460, 5,840,900, 5,880,131, and 6,376,470.

Additional PEG reagents for use in the invention include hydrolyzable and/or releasable PEGs and linkers such as those described in U.S. Patent Application Publication No. 2006-0293499. In the resulting conjugate, the protegrin peptide and the polymer are each covalently attached to different positions of the aromatic scaffold, e.g., Fmoc or FMS structure, and are releasable under physiological conditions. Generalized structures corresponding to the polymers described therein are provided below.

For example, one such polymeric reagent comprises the following structure:

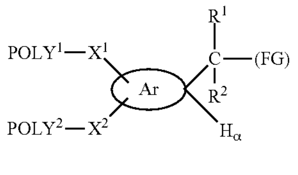

where $POLY^1$ is a first water-soluble polymer; $POLY^2$ is a second water-soluble polymer; $X^1$ is a first spacer moiety; $X^2$ is a second spacer moiety;

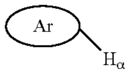

is an aromatic-containing moiety bearing an ionizable hydrogen atom, $H_\alpha$; $R^2$ is H or an organic radical; $R^2$ is H or an organic radical; and (FG) is a functional group capable of reacting with an amino group of an active agent to form a releasable linkage, such as a carbamate linkage (such as N-succinimidyloxy, 1-benzotriazolyloxy, oxycarbonylimidazole, —O—C(O)—Cl, O—C(O)—Br, unsubstituted aromatic carbonate radicals and substituted aromatic carbonate radicals). The polymeric reagent can include one, two, three, four or more electron altering groups attached to the aromatic-containing moiety.

Preferred aromatic-containing moieties are bicyclic and tricyclic aromatic hydrocarbons. Fused bicyclic and tricyclic aromatics include pentalene, indene, naphthalene, azulene, heptalene, biphenylene, as-indacene, s-indacene, acenaphthylene, fluorene, phenalene, phenanthrene, anthracene, and fluoranthene.

A preferred polymer reagent possesses the following structure.

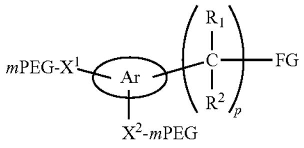

where mPEG corresponds to $CH_3O—(CH_2CH_2O)CH_2CH_2—$, $X^1$ and $X^2$ are each independently a spacer moiety having an atom length of from about 1 to about 18 atoms, n ranges from 10 to 1800, p is an integer ranging from 1 to 8. $R^1$ is H or lower alkyl, $R^2$ is H or lower alkyl, and Ar is an aromatic hydrodrocarbon, preferably a bicyclic or tricyclic aromatic hydrocarbon. FG is as defined above. Preferably, FG corresponds to an activated carbonate ester suitable for reaction with an amino group on protegrin peptide. Preferred spacer moieties, $X^1$ and $X^2$, include $—NH—C(O)—CH_2—O—$, $—NH—C(O)—(CH_2)_q—O—$, $—NH—C(O)—(CH_2)_q—C(O)—NH—$, $—NH—C(O)—(CH_2)_q—$, and —C(O)—NH—, where q is selected from 2, 3, 4, and 5. Preferably, although not necessarily, the nitrogen in the preceding spacers is proximal to the PEG rather than to the aromatic moiety.

Another such branched (2-armed) polymeric reagent comprised of two electron altering groups comprises the following structure:

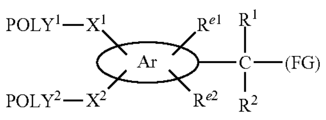

wherein each of $POLY^1$, $POLY^2$, $X^1$, $X^2$, $R^1$, $R^2$,

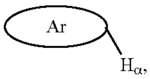

and (FG) is as defined immediately above, and $R^{e1}$ is a first electron altering group; and $R^{e2}$ is a second electron altering group. An electron altering group is a group that is either electron donating (and therefore referred to as an "electron donating group"), or electron withdrawing (and therefore referred to as an "electron withdrawing group"). When attached to the aromatic-containing moiety bearing an ionizable hydrogen atom, an electron donating group is a group having the ability to position electrons away from itself and closer to or within the aromatic-containing moiety. When attached to the aromatic-containing moiety bearing an ionizable hydrogen atom, an electron withdrawing group is a group having the ability to position electrons toward itself and away from the aromatic-containing moiety. Hydrogen is used as the standard for comparison in the determination of whether a given group positions electrons away or toward itself. Preferred electron altering groups include, but are not limited to, $—CF_3$, $—CH_2CF_3$, $—CH_2C_6F_5$, —CN, $—NO_2$, —S(O)R, —S(O)Aryl, $—S(O_2)R$, $—S(O_2)Aryl$, $—S(O_2)OR$, $—S(O_2)OAryl$, $—S(O_2)NHR$, $—S(O_2)NHAryl$, —C(O)R, —C(O)Aryl, —C(O)OR, —C(O)NHR, and the like, wherein R is H or an organic radical.

An additional branched polymeric reagent suitable for use in the present invention comprises the following structure:

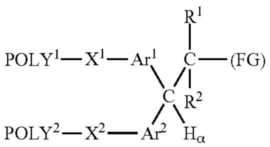

where $POLY^1$ is a first water-soluble polymer; $POLY^2$ is a second water-soluble polymer; $X^1$ is a first spacer moiety; $X^2$ is a second spacer moiety; $Ar^1$ is a first aromatic moiety; $Ar^2$ is a second aromatic moiety; $H_\alpha$ is an ionizable hydrogen atom; $R^1$ is H or an organic radical; $R^2$ is H or an organic radical; and (FG) is a functional group capable of reacting with an amino group of protegrin peptide to form a releasable linkage, such as carbamate linkage.

Another exemplary polymeric reagent comprises the following structure:

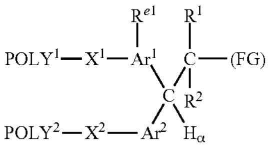

wherein each of $POLY^1$, $POLY^2$, $X^1$, $X^2$, $Ar^1$, $Ar^2$, $H_\alpha$, $R^1$, $R^2$, and (FG) is as previously defined, and $R^{e1}$ is a first electron altering group. While stereochemistry is not specifically shown in any structure provided herein, the provided structures contemplate both enantiomers, as well as compositions comprising mixtures of each enantiomer in equal amounts (i.e., a racemic mixture) and unequal amounts.

Yet an additional polymeric reagent for use in preparing a protegrin peptide conjugate possesses the following structure:

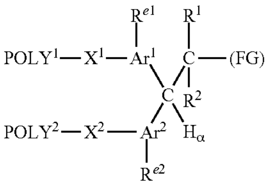

wherein each of $POLY^1$, $POLY^2$, $X^1$, $X^2$, $Ar^1$, $Ar^2$, $H_\alpha$, $R^1$, $R^2$, and (FG) is as previously defined, and $R^{e1}$ is a first electron altering group; and $R^{e2}$ is a second electron altering group.

A preferred polymeric reagent comprises the following structure:

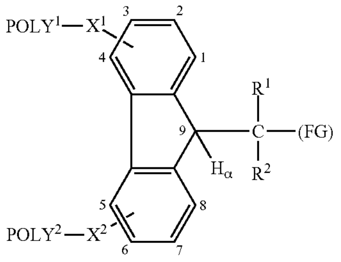

wherein each of $POLY^1$, $POLY^2$, $X^1$, $X^2$, $R^1$, $R^2$, $H_\alpha$ and (FG) is as previously defined, and, as can be seen from the structure above, the aromatic moiety is a fluorene. The POLY arms substituted on the fluorene can be in any position in each of their respective phenyl rings, i.e., $POLY^1$-$X^1$— can be positioned at any one of carbons 1, 2, 3, and 4, and $POLY^2$-$X^2$— can be in any one of positions 5, 6, 7, and 8.

Yet another preferred fluorene-based polymeric reagent comprises the following structure:

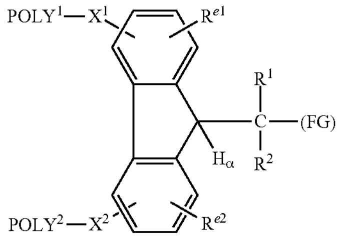

wherein each of $POLY^1$, $POLY^2$, $X^1$, $X^2$, $R^1$, $R^2$, $H_\alpha$ and (FG) is as previously defined, and $R^{e1}$ is a first electron altering group; and R is a second electron altering group as described above.

Yet another exemplary polymeric reagent for conjugating to a protegrin peptide comprises the following fluorene-based structure:

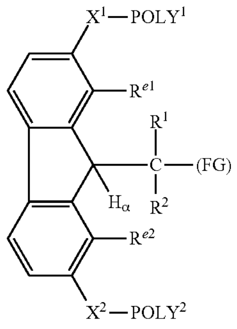

wherein each of $POLY^1$, $POLY^2$, $X^1$, $X^2$, $R^1$, $R^2$, $H_\alpha$ and (FG) is as previously defined, and $R^{e1}$ is a first electron altering group; and $R^{e2}$ is a second electron altering group.

Particular fluorene-based polymeric reagents for forming a releasable protegrin peptide polymer conjugate in accordance with the invention include the following:

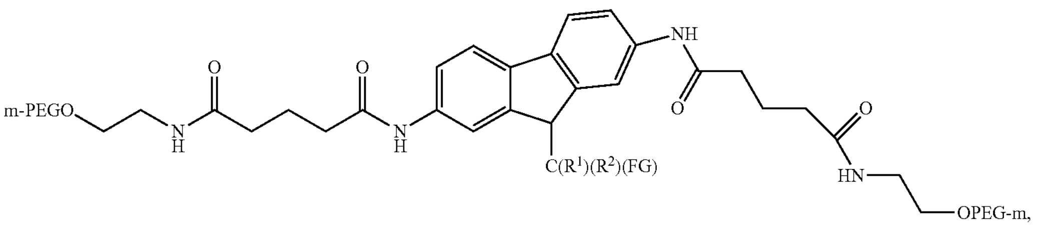

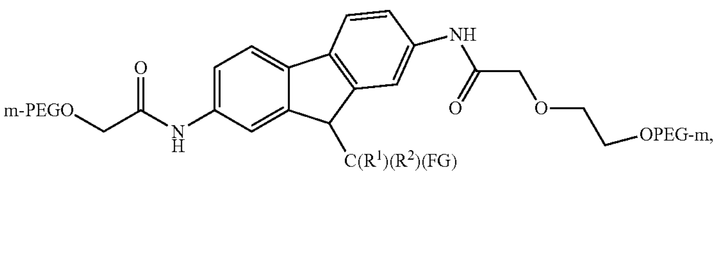

and

-continued

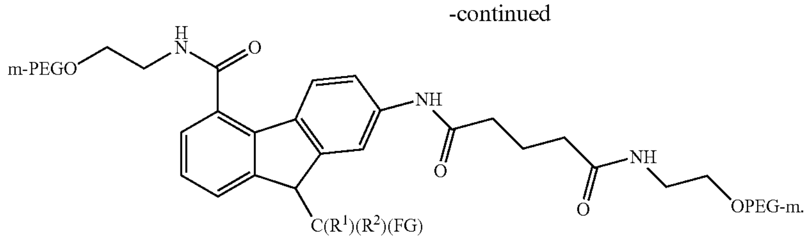

Still another exemplary polymeric reagent comprises the following structure:

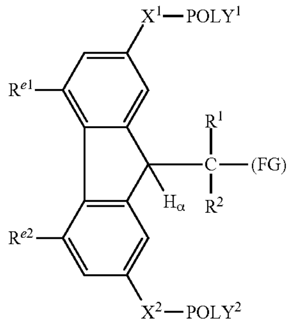

wherein each of $POLY^1$, $POLY^2$, $X^1$, $X^2$, $R^1$, $R^2$, $H_\alpha$ and (FG) is as previously defined, and $R^{e1}$ is a first electron altering group; and $R^{e2}$ is a second electron altering group. Branched reagents suitable for preparing a releasable protegrin peptide conjugate include N-{di(mPEG(20,000) oxymethylcarbonylamino)fluoren-9-ylmethoxycarbonyloxy}succinimide, N-[2,7 di(4mPEG(10, 000)aminocarbonylbutyrylamino)fluoren-9 ylmethoxycarbonyloxy]-succinimide ("G2PEG2Fmoc$_{20k}$-NHS"), and PEG2-CAC-Fmoc$_{4k}$-BTC. Of course, PEGs of any molecular weight as set forth herein may be employed in the above structures, and the particular activating groups described above are not meant to be limiting in any respect, and may be substituted by any other suitable activating group suitable for reaction with a reactive group present on the protegrin peptide.

Those of ordinary skill in the art will recognize that the foregoing discussion describing water-soluble polymers for use in forming a protegrin peptide conjugate is by no means exhaustive and is merely illustrative, and that all polymeric materials having the qualities described above are contemplated. As used herein, the term "polymeric reagent" generally refers to an entire molecule, which can comprise a water-soluble polymer segment, as well as additional spacers and functional groups.

The Linkage

The particular linkage between the protegrin peptide and the water-soluble polymer depends on a number of factors. Such factors include, for example, the particular linkage chemistry employed, the particular spacer moieties utilized, if any, the particular protegrin peptide, the available functional groups within the protegrin peptide (either for attachment to a polymer or conversion to a suitable attachment site), and the possible presence of additional reactive functional groups or absence of functional groups within the protegrin peptide due to modifications made to the peptide such as methylation and/or glycosylation, and the like.

In one or more embodiments of the invention, the linkage between the protegrin peptide and the water-soluble polymer is a releasable linkage. That is, the water-soluble polymer is cleaved (either through hydrolysis, an enzymatic processes, or otherwise), thereby resulting in an unconjugated protegrin peptide. Preferably, the releasable linkage is a hydrolytically degradable linkage, where upon hydrolysis, the protegrin peptide, or a slightly modified version thereof, is released. The releasable linkage may result in the water-soluble polymer (and any spacer moiety) detaching from the protegrin peptide in vivo (and in vitro) without leaving any fragment of the water-soluble polymer (and/or any spacer moiety or linker) attached to the protegrin peptide. Exemplary releasable linkages include carbonate, carboxylate ester, phosphate ester, thiolester, anhydrides, acetals, ketals, acyloxyalkyl ether, imines, carbamates, and orthoesters. Such linkages can be readily formed by reaction of the protegrin peptide and/or the polymeric reagent using coupling methods commonly employed in the art. Hydrolyzable linkages are often readily formed by reaction of a suitably activated polymer with a non-modified functional group contained within the protegrin peptide. Preferred positions for covalent attachment of a water-soluble polymer include the N-terminal, the C-terminal, as well as the internal lysines. Preferred releasable linkages include carbamate and ester.

Generally speaking, a preferred protegrin peptide conjugate of the invention will possess the following generalized structure:

$$[POLY—X]_k—PRO$$

where POLY is a water-soluble polymer such as any of the illustrative polymeric reagents provided in Tables 2-4 herein, X is a linker, and in some embodiments a hydrolyzable linkage ($L_D$), and k is an integer selected from 1, 2, and 3, and in some instances 4, 5, 6, 7, 8, 9 and 10. In the generalized structure above, where X is $L_D$, $L_D$ refers to the hydrolyzable linkage per se (e.g., a carbamate or an ester linkage), while "POLY" is meant to include the polymer repeat units, e.g., $CH_3(OCH_2CH_2)_n$—, and PRO is used to describe protegrin. In a preferred embodiment of the invention, at least one of the water-soluble polymer molecules is covalently attached to the N-terminus of protegrin peptide. In one embodiment of the invention, k equals 1 and X is —O—C(O)—NH—, where the —NH— is part of the protegrin peptide residue and represents an amino group thereof.

Although releasable linkages are exemplary, the linkage between the protegrin peptide and the water-soluble polymer (or the linker moiety that is attached to the polymer) may be a hydrolytically stable linkage, such as an amide, a urethane (also known as carbamate), amine, thioether (also known as sulfide), or urea (also known as carbamide). One such embodiment of the invention comprises a protegrin peptide having a water-soluble polymer such as PEG covalently attached at the N-terminus of protegrin peptide. In such instances, alkylation of the N-terminal residue permits retention of the charge on the N-terminal nitrogen.

With regard to linkages, in one or more embodiments of the invention, a conjugate is provided that comprises a protegrin peptide covalently attached at an amino acid residue, either directly or through a linker comprised of one or more atoms, to a water-soluble polymer.

The conjugates (as opposed to an unconjugated protegrin peptide) may or may not possess a measurable degree of protegrin peptide activity. That is to say, a conjugate in accordance with the invention will typically possess anywhere from about 0% to about 100% or more of the protegrin activity of the unmodified parent protegrin peptide. Typically, compounds possessing little or no protegrin activity contain a releasable linkage connecting the polymer to the protegrin peptide, so that regardless of the lack of protegrin activity in the conjugate, the active parent molecule (or a derivative thereof having protegrin activity) is released by cleavage of the linkage (e.g., hydrolysis upon aqueous-induced cleavage of the linkage). Such activity may be determined using a suitable in vivo or in vitro model, depending upon the known activity of the particular moiety having protegrin peptide activity employed.

Optimally, cleavage of a linkage is facilitated through the use of hydrolytically cleavable and/or enzymatically cleavable linkages such as urethane, amide, certain carbamate, carbonate or ester-containing linkages. In this way, clearance of the conjugate via cleavage of individual water-soluble polymer(s) can be modulated by selecting the polymer molecular size and the type of functional group for providing the desired clearance properties. In certain instances, a mixture of polymer conjugates is employed where the polymers possess structural or other differences effective to alter the release (e.g., hydrolysis rate) of the protegrin peptide, such that one can achieve a desired sustained delivery profile.

One of ordinary skill in the art can determine the proper molecular size of the polymer as well as the cleavable functional group, depending upon several factors including the mode of administration. For example, one of ordinary skill in the art, using routine experimentation, can determine a proper molecular size and cleavable functional group by first preparing a variety of polymer-protegrin peptide conjugates with different weight-average molecular weights, degradable functional groups, and chemical structures, and then obtaining the clearance profile for each conjugate by administering the conjugate to a patient and taking periodic blood and/or urine samples. Once a series of clearance profiles has been obtained for each tested conjugate, a conjugate or mixture of conjugates having the desired clearance profile(s) can be determined.

For conjugates possessing a hydrolytically stable linkage that couples the protegrin peptide to the water-soluble polymer, the conjugate will typically possess a measurable degree of protegrin activity. For instance, such conjugates are typically characterized as having a protegrin activity satisfying one or more of the following percentages relative to that of the unconjugated protegrin peptide: at least 2%, at least 5%, at least 10%, at least 15%, at least 25%, at least 30%, at least 40%, at least 50%, at least 60%, at least 80%, at least 85%, at least 90%, at least 95%, at least 97%, at least 100%, more than 105%, more than 10-fold, or more than 100-fold (when measured in a suitable model, such as those presented here and/or known in the art). Often, conjugates having a hydrolytically stable linkage (e.g., an amide linkage) will possess at least some degree of the protegrin activity of the unmodified parent protegrin peptide.

Exemplary conjugates in accordance with the invention will now be described. Amino groups on a protegrin peptide provide a point of attachment between the protegrin peptide and the water-soluble polymer. For example, a protegrin peptide may comprise one or more lysine residues, each lysine residue containing an s-amino group that may be available for conjugation, as well as the amino terminus.

There are a number of examples of suitable water-soluble polymeric reagents useful for forming covalent linkages with available amines of a protegrin peptide. Certain specific examples, along with the corresponding conjugates, are provided in Table 2 below. In the table, the variable (n) represents the number of repeating monomeric units and "PRO" represents a protegrin peptide following conjugation to the water-soluble polymer. While each polymeric portion [e.g., $(OCH_2CH_2)_n$ or $(CH_2CH_2O)_n$] presented in Table 2 terminates in a "$CH_3$" group, other groups (e.g., H or benzyl) can be substituted therefore.

As will be clearly understood by one skilled in the art, for conjugates such as those set forth below resulting from reaction with a protegrin peptide amino group, the amino group extending from the protegrin peptide designation "—NH-protegrin" represents the residue of the protegrin peptide itself in which the —NH— is an amino group of the protegrin peptide. One preferred site of attachment for the polymeric reagents shown below is the N-terminus. Further, although the conjugates in Tables 2-4 herein illustrate a single water-soluble polymer covalently attached to a protegrin peptide, it will be understood that the conjugate structures on the right are meant to also encompass conjugates having more than one of such water-soluble polymer molecules covalently attached to protegrin peptide, e.g., 2, 3, or 4 water-soluble polymer molecules.

TABLE 2

| Amine-Specific Polymeric Reagents and the protegrin Peptide Conjugates Formed Therefrom | |
|---|---|
| 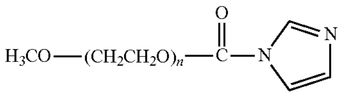<br>mPEG-Oxycarbonylimidazole Reagent | 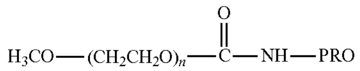<br>Carbamate Linkage |
| 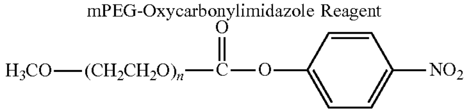<br>mPEG Nitrophenyl Reagent | 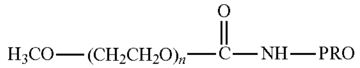<br>Carbamate Linkage |
| 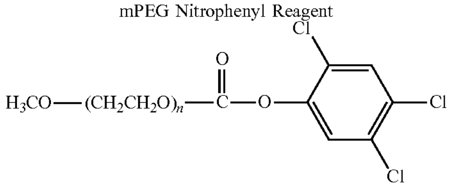<br>mPEG-Trichlorophenyl Carbonate Reagent | 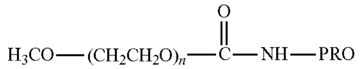<br>Carbamate Linkage |
| 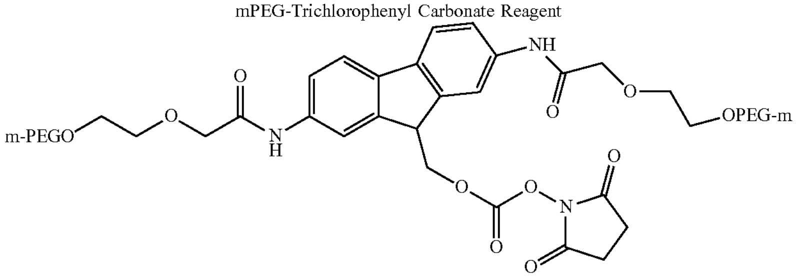<br>Fmoc-NHS Reagent | 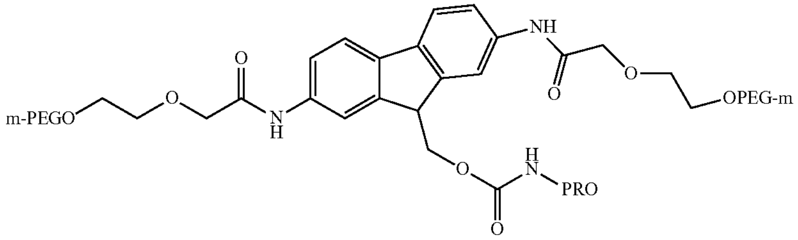<br>Carbamate Linkage |
| 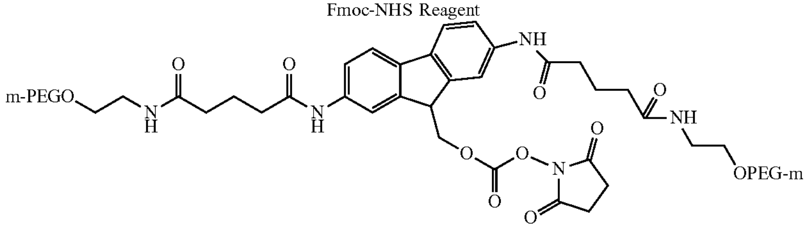<br>Fmoc-NHS Reagent | 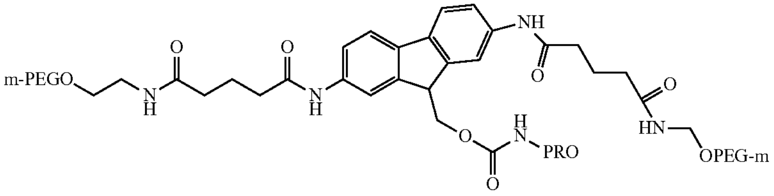<br>Carbamate Linkage |

TABLE 2-continued
Amine-Specific Polymeric Reagents and the protegrin Peptide Conjugates Formed Therefrom
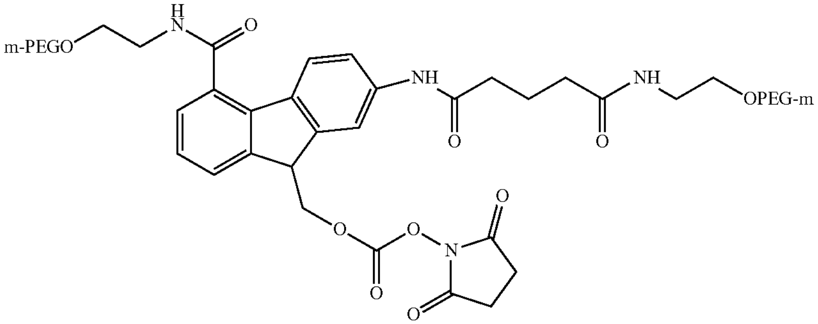
Fmoc-NHS Reagent
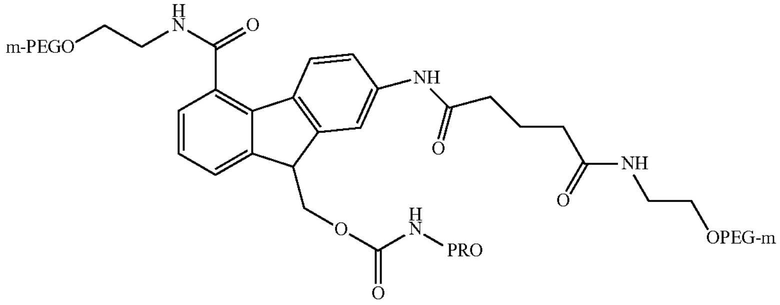
Carbamate Linkage
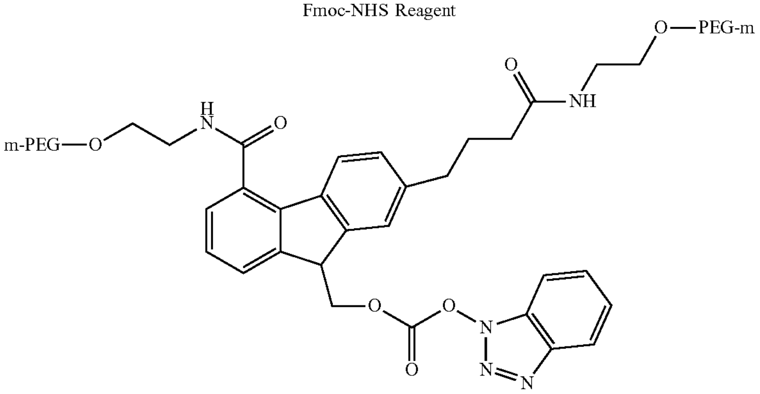
Fmoc-BTC Reagent
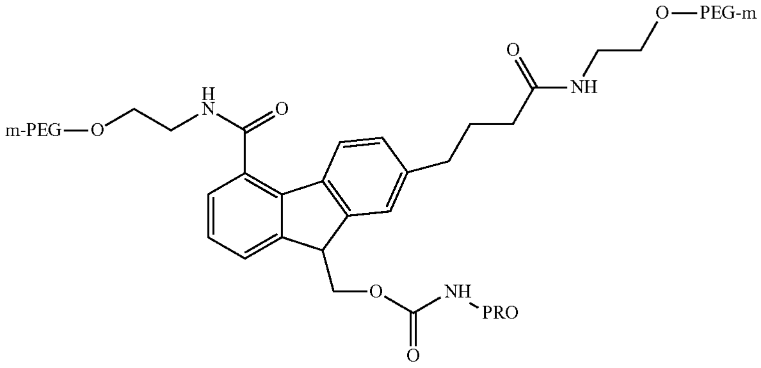
Carbamate Linkage
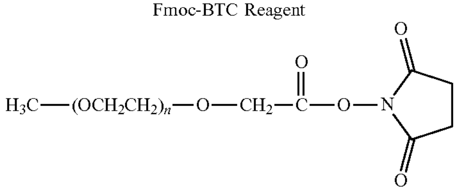
mPEG-Succinimidyl Reagent
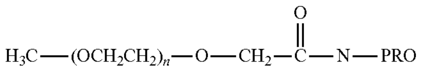
Amide Linkage TABLE 2-continued
| Amine-Specific Polymeric Reagents and the protegrin Peptide Conjugates Formed Therefrom | |
|---|---|
| 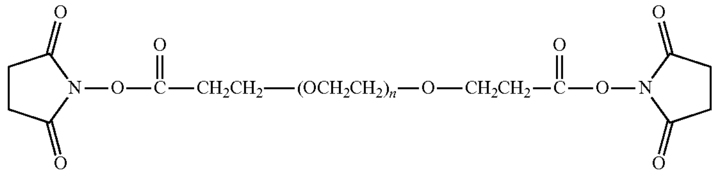<br>Homobifunctional PEG-Succinimidyl Reagent | 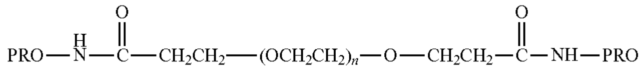<br>Amide Linkages |
| 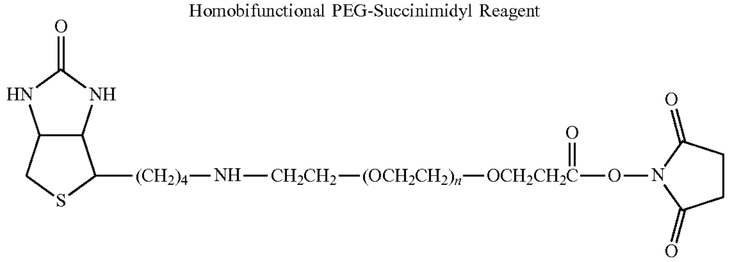<br>Heterobifunctional PEG-Succinimidyl Reagent | 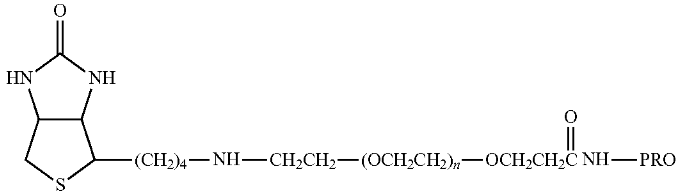<br>Amide Linkage |
| 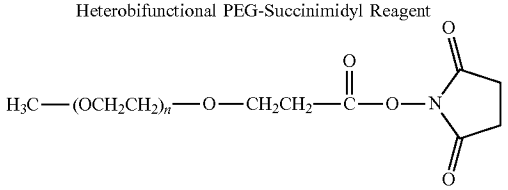<br>mPEG-Succinimidyl Reagent | 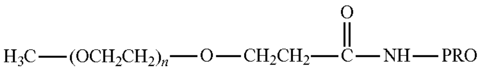<br>Amide Linkage |
| 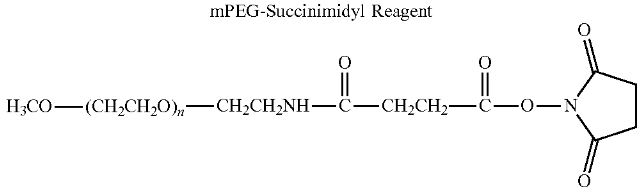<br>mPEG-Succinimidyl Reagent | 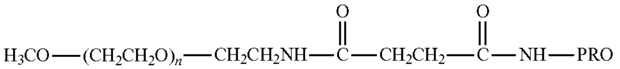<br>Amide Linkage |

TABLE 2-continued

| Amine-Specific Polymeric Reagents and the protegrin Peptide Conjugates Formed Therefrom | |
|---|---|
| 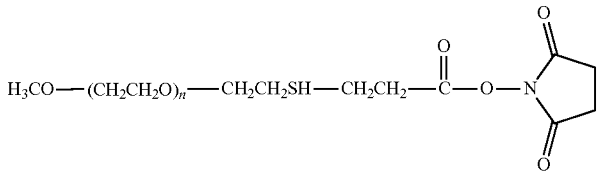<br>mPEG Succinimidyl Reagent | 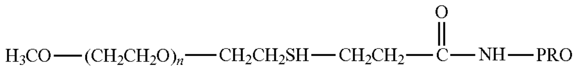<br>Amide Linkage |
| 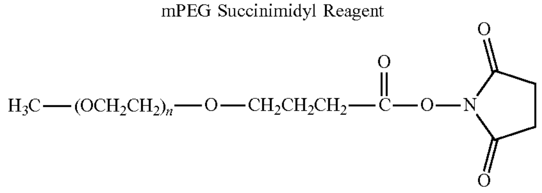<br>mPEG Succinimidyl Reagent | 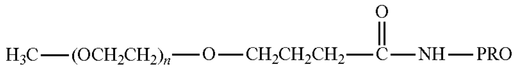<br>Amide Linkage |
| 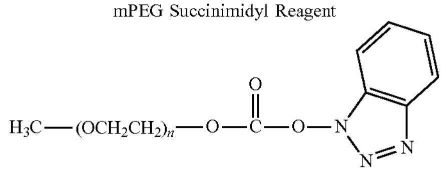<br>mPEG-Benzotriazole Carbonate Reagent | 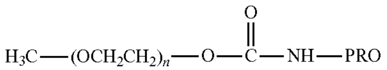<br>Carbamate Linkage |
| 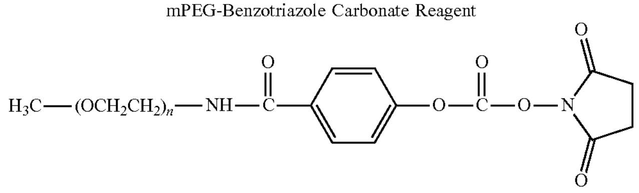<br>mPEG-Succinimidyl Reagent | 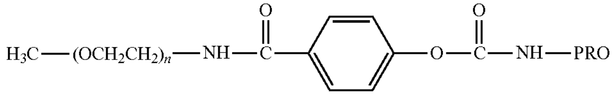<br>Carbamate Linkage |
| 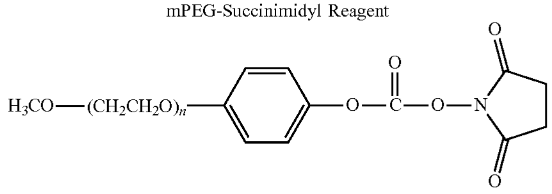<br>mPEG-Succinimidyl Reagent | 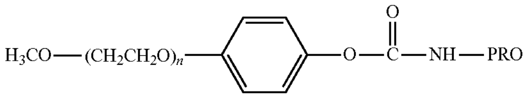<br>Amide Linkage |

TABLE 2-continued
| Amine-Specific Polymeric Reagents and the protegrin Peptide Conjugates Formed Therefrom | |
|---|---|
| 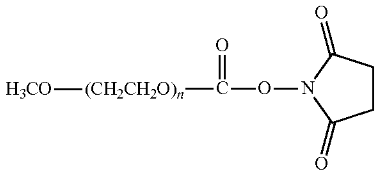<br>mPEG-Succinimidyl Reagent | 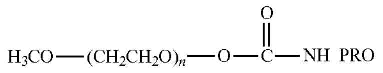<br>Amide Linkage |
| 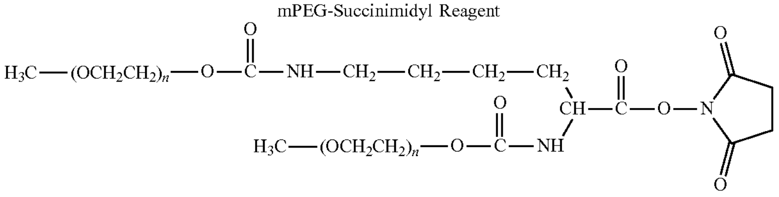<br>Branched mPEG2-N-Hydroxysuccinimide Reagent | 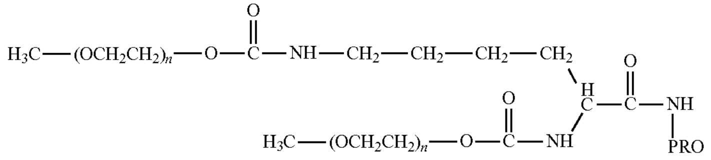<br>Amide Linkage |
| 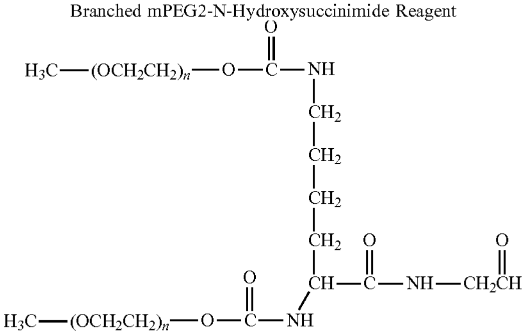<br>Branched mPEG-2-Aldehyde Reagent | 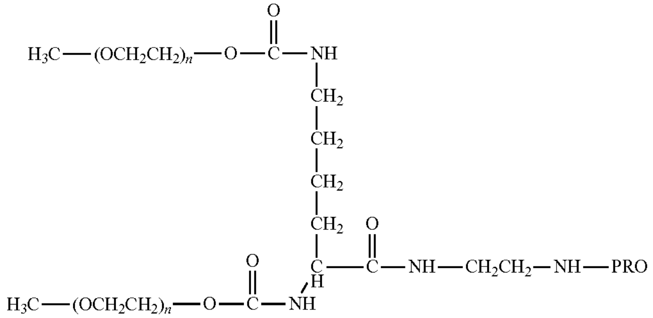<br>Secondary Amine Linkage |
| 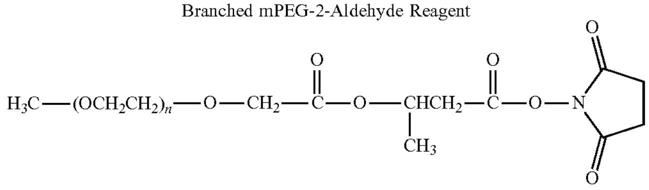<br>mPEG-Succinimidyl Reagent | 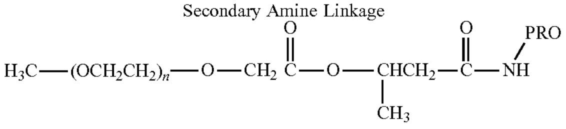<br>Amide Linkage |

TABLE 2-continued
| Amine-Specific Polymeric Reagents and the protegrin Peptide Conjugates Formed Therefrom | |
|---|---|
| 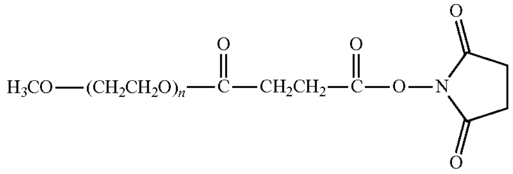<br>mPEG-Succinimidyl Reagent | 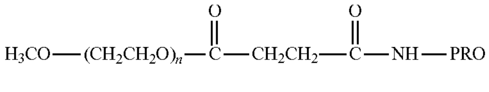<br>Amide Linkage |
| 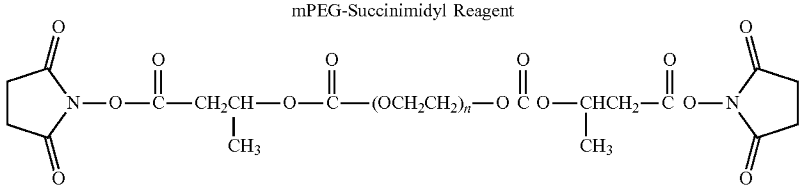<br>Homobifunctional PEG-Succinimidyl Reagent | 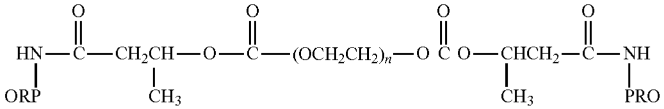<br>Amide Linkages |
| 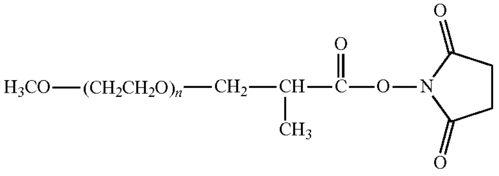<br>mPEG-Succinimidyl Reagent | 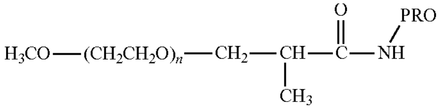<br>Amide Linkage |
| 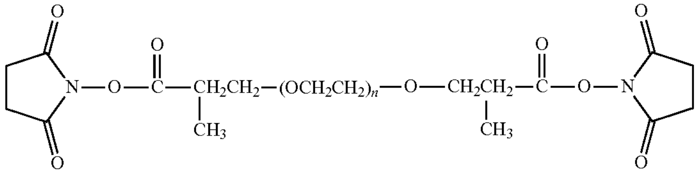<br>Homobifunctional PEG-Succinimidyl Propionate Reagent | 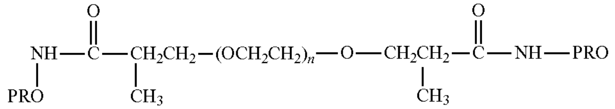<br>Amide Linkages |

TABLE 2-continued

| Amine-Specific Polymeric Reagents and the protegrin Peptide Conjugates Formed Therefrom | |
|---|---|
| 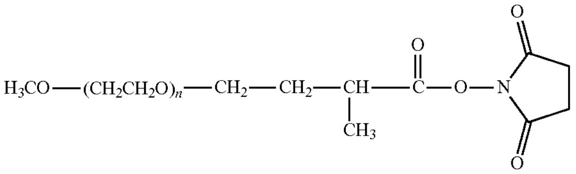 mPEG-Succinimidyl Reagent | 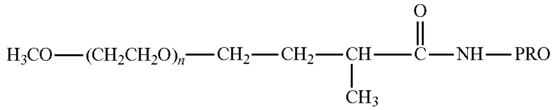 Amide Linkage |
| 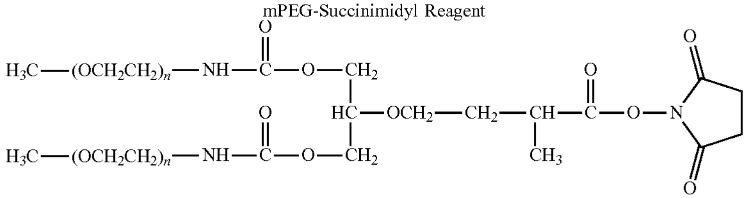 Branched mPEG2-N-Hydroxysuccinimide Reagent | 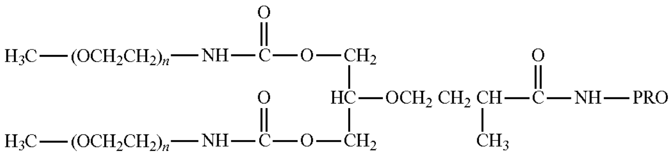 Amide Linkage |
| 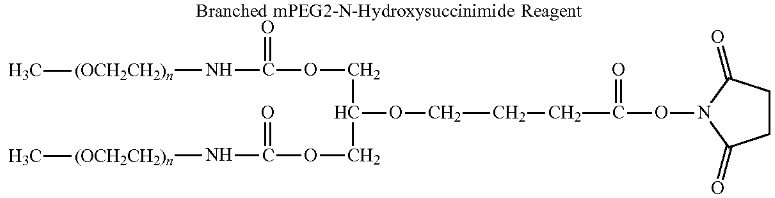 Branched mPEG2-N-Hydroxysuccinimide Reagent | 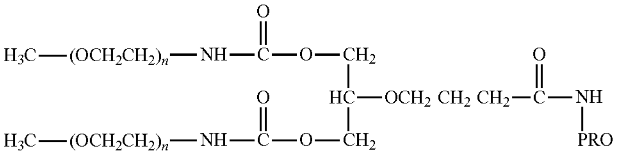 Amide Linkage |
| 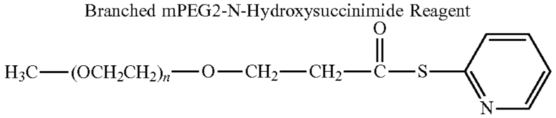 mPEG-Thioester Reagent | 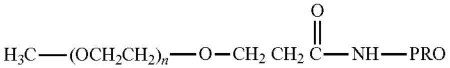 Amide Linkage (typically to protegrin moiety having an N-terminal cysteine or histidine) |
| 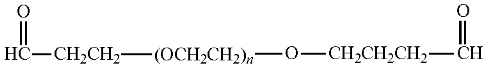 Homobifunctional PEG Propionaldehyde Reagent | 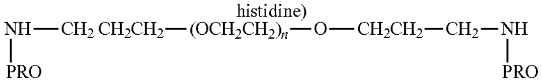 Secondary Amine Linkages |
| 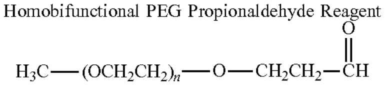 mPEG Propionaldehyde Reagent | $H_3C—(OCH_2CH_2)_n—O—CH_2CH_2—CH_2—NH—PRO$ Secondary Amine Linkage |

TABLE 2-continued

| Amine-Specific Polymeric Reagents and the protegrin Peptide Conjugates Formed Therefrom | |
|---|---|
| 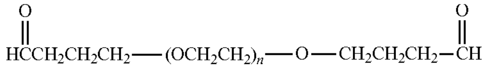<br>Homobifunctional PEG Butyraldehyde Reagent | 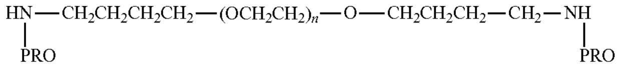<br>Secondary Amine Linkages |
| 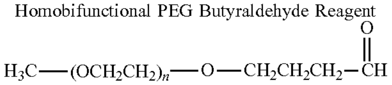<br>mPEG Butryaldehyde Reagent | $H_3C—(OCH_2CH_2)_n—O—CH_2CH_2CH_2—CH_2—NH—PRO$<br>Secondary Amine Linkage |
| 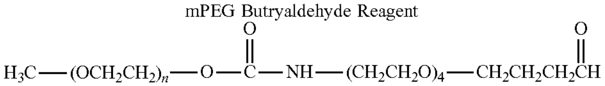<br>mPEG Butryaldehyde Reagent | 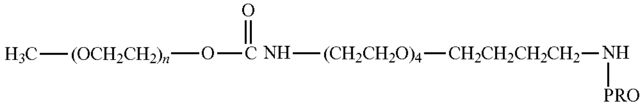<br>Secondary Amine Linkage |
| 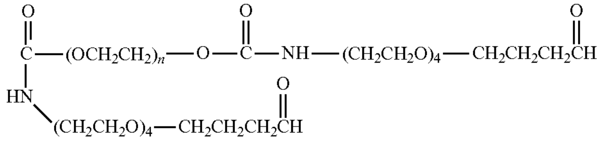<br>Homobifunctional PEG Butryaldehyde Reagent | 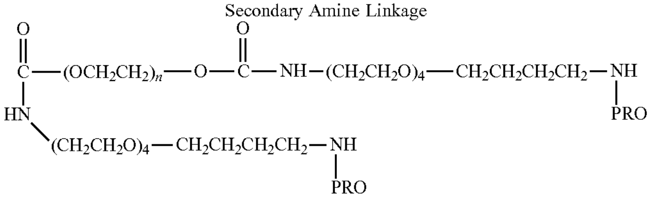<br>Secondary Amine Linkages |
| 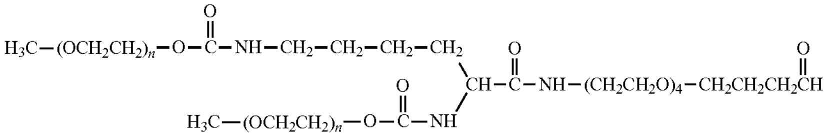<br>Branched mPEG2 Butyraldehyde Reagent | 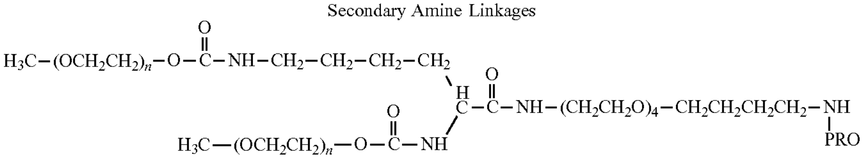<br>Secondary Amine Linkage |
| 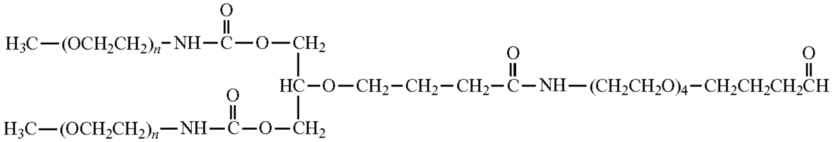<br>Branched mPEG2 Butyraldehyde Reagent | 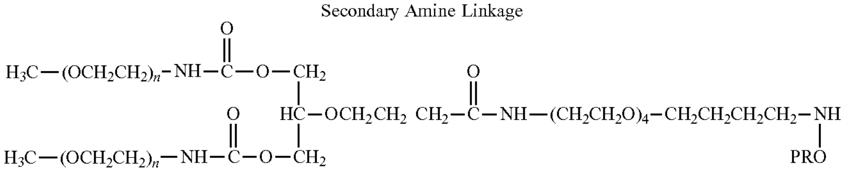<br>Secondary Amine Linkage |
| 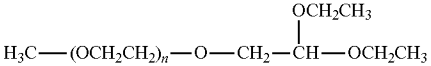<br>mPEG Acetal Reagent | 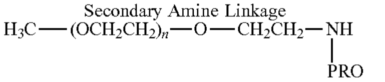<br>Secondary Amine Linkage |

TABLE 2-continued

| Amine-Specific Polymeric Reagents and the protegrin Peptide Conjugates Formed Therefrom | |
|---|---|
| 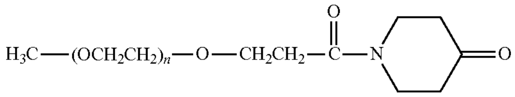<br>mPEG Piperidone Reagent | 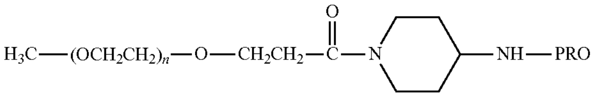<br>Secondary Amine Linkage<br>(to a secondary carbon) |
| 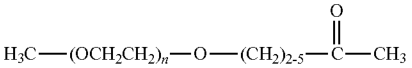<br>mPEG Methylketone Reagent | 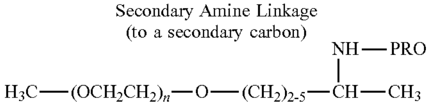<br>secondary amine linkage<br>(to a secondary carbon) |
| 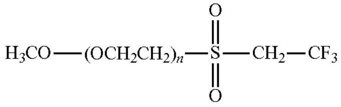<br>mPEG tresylate Reagent | $H_3CO—(CH_2CH_2O)_n—O—CH_2CH_2—NH—PRO$<br>Secondary Amine Linkage |
| 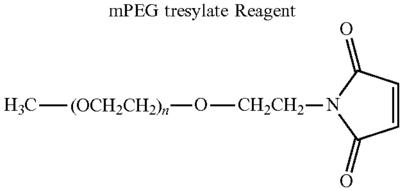<br>mPEG Maleimide Reagent<br>(under certain reaction conditions such as pH >8) | 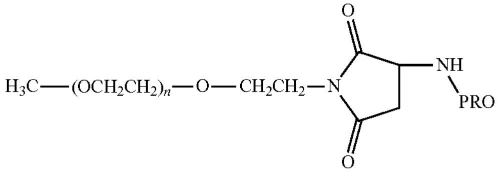<br>Secondary Amine Linkage |
| 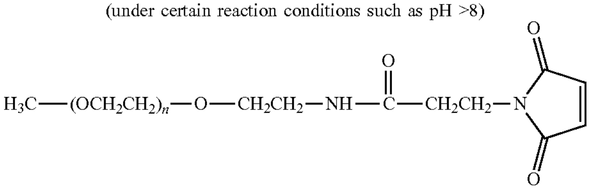<br>mPEG Maleimide Reagent<br>(under certain reaction conditions such as pH >8) | 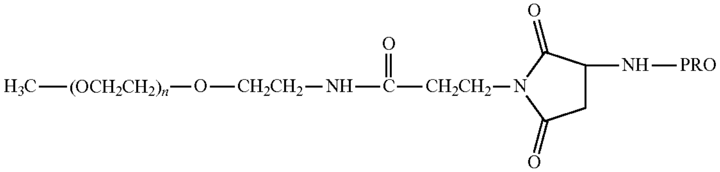<br>Secondary Amine Linkage |

TABLE 2-continued
| Amine-Specific Polymeric Reagents and the protegrin Peptide Conjugates Formed Therefrom | |
|---|---|
| 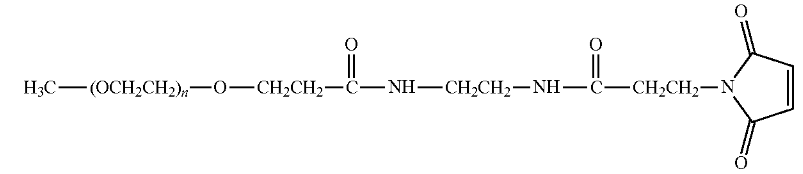<br>mPEG Maleimide Reagent<br>(under certain reaction conditions such as pH >8) | 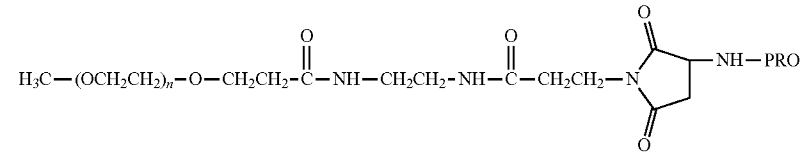<br>Secondary Amine Linkage |
| 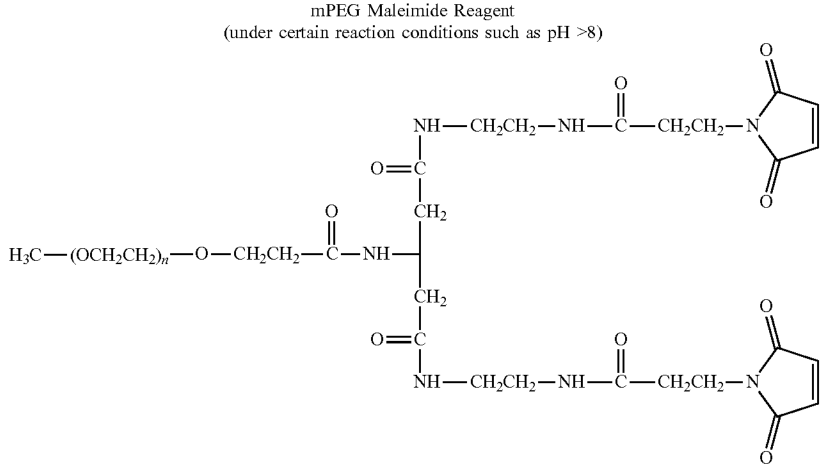<br>mPEG Forked Maleimide Reagent<br>(under certain reaction conditions such as pH >8) | 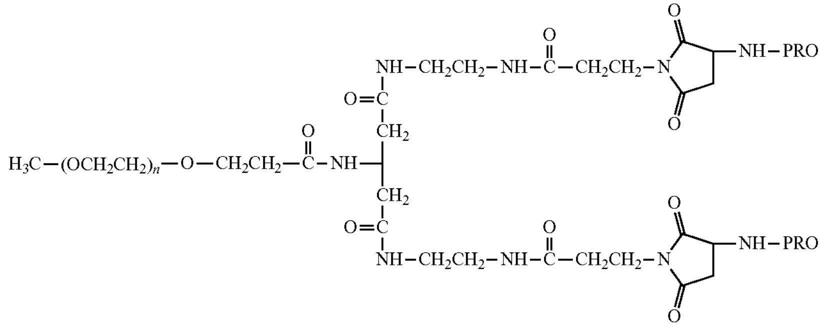<br>Secondary Amine Linkages |

TABLE 2-continued
| Amine-Specific Polymeric Reagents and the protegrin Peptide Conjugates Formed Therefrom | |
|---|---|
| 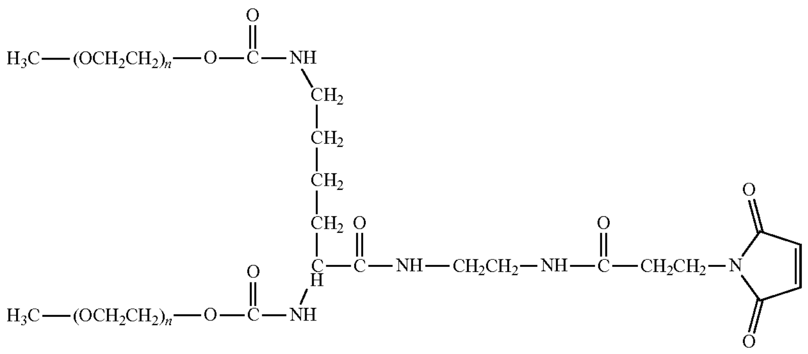 branched mPEG2 Maleimide Reagent (under certain reaction conditions such as pH >8) | 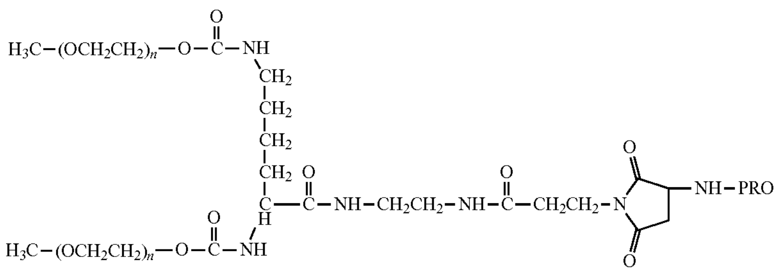 Secondary Amine Linkage |

Amine Conjugation and Resulting Conjugates

Conjugation of a polymeric reagent to an amine group of a protegrin peptide can be accomplished by a variety of techniques. In one approach, a protegrin peptide is conjugated to a polymeric reagent functionalized with an active ester such as a succinimidyl derivative (e.g., an N-hydroxysuccinimide ester) In this approach, the polymeric reagent bearing the reactive ester is reacted with the protegrin peptide in aqueous media under appropriate pH conditions, e.g. from pHs ranging from about 3 to about 8, about 3 to about 7, or about 4 to about 65. Most polymer active esters can couple to a target peptide such as protegrin peptide at physiological pH, e.g., at 7.0. However, less reactive derivatives may require a different pH. Typically, activated PEGs can be attached to a peptide such as protegrin peptide at pHs from about 7.0 to about 10.0 for covalent attachment to an internal lysine. Typically, lower pHs are used, e.g., 4 to about 5.75, for preferential covalent attachment to the N-terminus. Thus, different reaction conditions (e.g., different pHs or different temperatures) can result in the attachment of a water-soluble polymer such as PEG to different locations on the protegrin peptide (e.g., internal lysines versus the N-terminus). Coupling reactions can often be carried out at room temperature, although lower temperatures may be required for particularly labile protegrin peptide moieties. Reaction times are typically on the order of minutes, e.g., 30 minutes, to hours, e.g., from about 1 to about 36 hours), depending upon the pH and temperature of the reaction. N-terminal PEGylation, e.g., with a PEG reagent bearing an aldehyde group, is typically conducted under mild conditions, pHs from about 5-10, for about 6 to 36 hours. Varying ratios of polymeric reagent to protegrin peptide may be employed, e.g., from an equimolar ratio up to a 10-fold molar excess of polymer reagent. Typically, up to a 5-fold molar excess of polymer reagent will suffice.

In certain instances, it may be preferable to protect certain amino acids from reaction with a particular polymeric reagent if site specific or site selective covalent attachment is desired using commonly employed protection/deprotection methodologies such as those well known in the art.

In an alternative approach to direct coupling reactions, the PEG reagent may be incorporated at a desired position of the protegrin peptide during peptide synthesis. In this way, site-selective introduction of one or more PEGs can be achieved. See, e.g., International Patent Publication No. WO 95/00162, which describes the site selective synthesis of conjugated peptides.

Exemplary conjugates that can be prepared using, for example, polymeric reagents containing a reactive ester for coupling to an amino group of protegrin peptide, comprise the following alpha-branched structure:

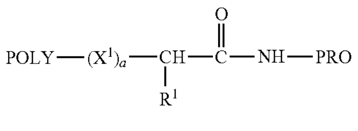

where POLY is a water-soluble polymer, (a) is either zero or one; $X^1$, when present, is a spacer moiety comprised of one or more atoms; $R^1$ is hydrogen an organic radical; and "~NH-protegrin" represents a residue of a protegrin peptide, where the underlined amino group represents an amino group of the protegrin peptide.

With respect to the structure corresponding to that referred to in the immediately preceding paragraph, any of the water-soluble polymers provided herein can be defined as POLY, any of the spacer moieties provided herein can be defined as $X^1$ (when present), any of the organic radicals provided herein can be defined as $R^1$ (in instances where $R^1$ is not hydrogen), and any of the protegrin peptides provided herein can be employed. In one or more embodiments corresponding to the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (a) is one; $X^1$ is a $C_{1-6}$ alkylene, such as one selected from methylene (i.e., —$CH_2$—), ethylene (i.e., —$CH_2$—$CH_2$—) and propylene (i.e., —$CH_2$—$CH_2$—$CH_2$—); $R^1$ is H or lower alkyl such as methyl or ethyl; and protegrin corresponds to any protegrin peptide disclosed herein, including in Table 1.

Typical of another approach for conjugating a protegrin peptide to a polymeric reagent is reductive amination. Typically, reductive amination is employed to conjugate a primary amine of a protegrin peptide with a polymeric reagent functionalized with a ketone, aldehyde or a hydrated form thereof (e.g., ketone hydrate and aldehyde hydrate). In this approach, the primary amine from the protegrin peptide (e.g., the N-terminus) reacts with the carbonyl group of the aldehyde or ketone (or the corresponding hydroxy-containing group of a hydrated aldehyde or ketone), thereby forming a Schiff base. The Schiff base, in turn, is then reductively converted to a stable conjugate through use of a reducing agent such as sodium borohydride or any other suitable reducing agent. Selective reactions (e.g., at the N-terminus) are possible, particularly with a polymer functionalized with a ketone or an alpha-methyl branched aldehyde and/or under specific reaction conditions (e.g., reduced pH).

Exemplary conjugates that can be prepared using, for example, polymeric reagents containing an aldehyde (or aldehyde hydrate) or ketone or (ketone hydrate) possess the following structure:

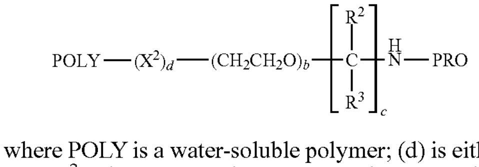

where POLY is a water-soluble polymer; (d) is either zero or one; $X^2$, when present, is a spacer moiety comprised of one or more atoms; (b) is an integer having a value of one through ten; (c) is an integer having a value of one through ten; $R^2$, in each occurrence, is independently H or an organic radical; $R^3$, in each occurrence, is independently H or an organic radical; and "~NH-protegrin" represents a residue of a protegrin peptide, where the underlined amino group represents an amino group of the protegrin peptide.

Yet another illustrative conjugate of the invention possesses the structure:

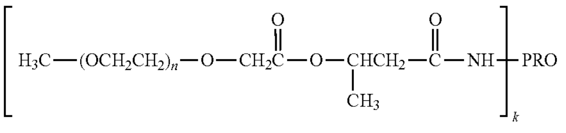

where k ranges from 1 to 3, and n ranges from 10 to about 1800.

With respect to the structure corresponding to that referred to in immediately preceding paragraph, any of the water-soluble polymers provided herein can be defined as POLY, any of the spacer moieties provided herein can be defined as $X^2$ (when present), any of the organic radicals provided herein can be independently defined as $R^2$ and $R^3$ (in instances where $R^2$ and $R^3$ are independently not hydrogen), and any of the protegrin moieties provided herein can be defined as a protegrin peptide. In one or more embodiments of the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (d) is one; $X^1$ is amide [e.g., —C(O)NH—]; (b) is 2 through 6, such as 4; (c) is 2 through 6, such as 4; each of $R^2$ and $R^3$ are independently H or lower alkyl, such as methyl when lower alkyl; and protegrin is protegrin peptide.

Another example of a protegrin peptide conjugate in accordance with the invention has the following structure:

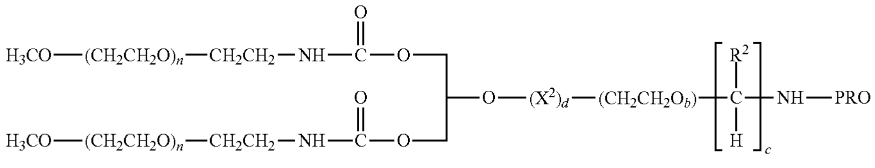

wherein each (n) is independently an integer having a value of from 3 to 4000, preferably from 10 to 1800; $X^2$ is as previously defined; (b) is 2 through 6; (c) is 2 through 6; $R^2$, in each occurrence, is independently H or lower alkyl; and "~NH-protegrin" represents a residue of a protegrin peptide, where the underlined amino group represents an amino group of the protegrin peptide.

Additional protegrin peptide polymer conjugates resulting from reaction of a water-soluble polymer with an amino group of protegrin peptide are provided below. The following conjugate structures are releasable. One such structure corresponds to:

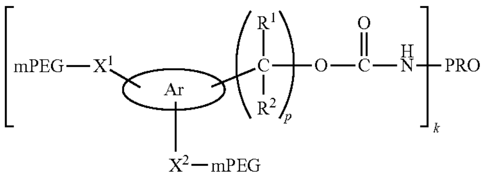

where mPEG is $CH_3O—(CH_2CH_2O)_nCH_2CH_2—$, n ranges from 10 to 1800, p is an integer ranging from 1 to 8, $R^1$ is H or lower alkyl, $R^2$ is H or lower alkyl, Ar is an aromatic hydrocarbon, such as a fused bicyclic or tricyclic aromatic hydrocarbon, $X^1$ and $X^2$ are each independently a spacer moiety having an atom length of from about 1 to about 18 atoms, NH-protegrin is as previously described, and k is an integer selected from 1, 2, and 3. The value of k indicates the number of water-soluble polymer molecules attached to different sites on the protegrin peptide. In a preferred embodiment, $R^1$ and $R^2$ are both H. The spacer moieties, $X^1$ and $X^2$, preferably each contain one amide bond. In a preferred embodiment, $X^1$ and $X^2$ are the same. Preferred spacers. i.e., $X^1$ and $X^2$, include —NH—C(O)—$CH_2$—O—, —NH—C(O)—$(CH_2)_q$—O—, —NH—C(O)—$(CH_2)_q$—C(O)—NH—, —NH—C(O)—$(CH_2)_q$—, and —C(O)—NH—, where q is selected from 2, 3, 4, and 5. Although the spacers can be in either orientation, preferably, the nitrogen is proximal to the PEG rather than to the aromatic moiety. Illustrative aromatic moieties include pentalene, indene, naphthalene, indacene, acenaphthylene, and fluorene.

Particularly preferred conjugates of this type are provided below.

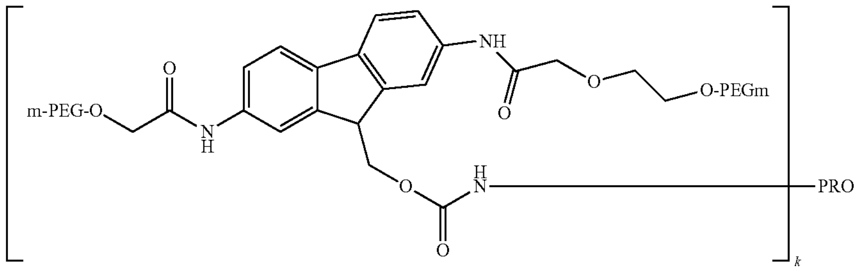

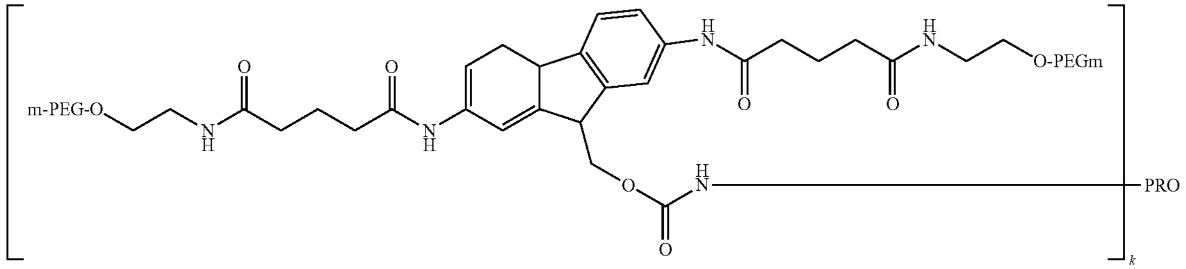

-continued

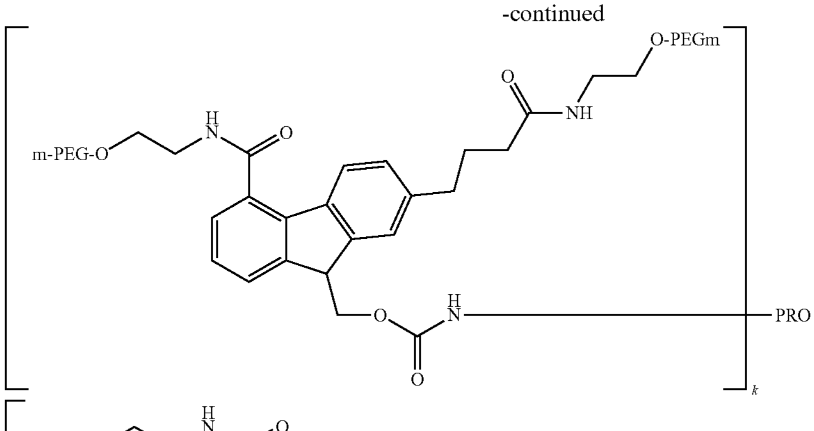

and

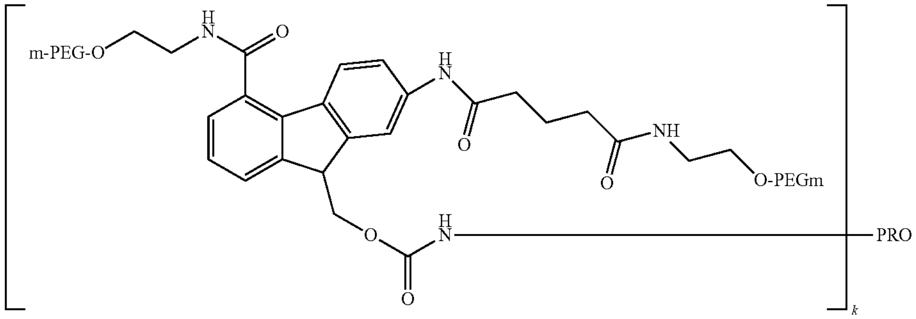

Additional protegrin peptide conjugates resulting from covalent attachment to amino groups of protegrin peptide that are also releasable include the following:

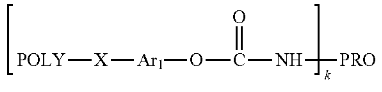

where X is either —O— or —NH—C(O)—, $Ar_1$ is an aromatic group, e.g., ortho, meta, or para-substituted phenyl, and k is an integer selected from 1, 2, and 3. Particular conjugates of this type include:

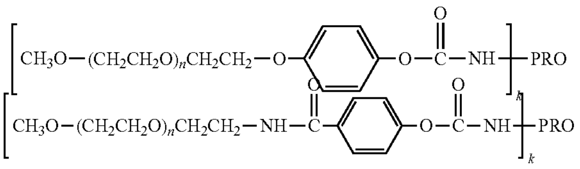

where n ranges from about 10 to about 1800.

Additional releasable conjugates in accordance with the invention are prepared using water-soluble polymer reagents such as those described in U.S. Pat. No. 6,214,966. Such water-soluble polymers result in a releasable linkage following conjugation, and possess at least one releasable ester linkage close to the covalent attachment to the active agent. The polymers generally possess the following structure, PEG-W—$CO_2$—NHS or an equivalent activated ester, where $W$ = $-O_2C-(CH_2)_b-O-$ $b = 1-5$ $-O(CH_2)_bCO_2-(CH_2)_c-$ $b = 1-5, c = 2-5$ $-O-(CH_2)_b-CO_2-(CH_2)_c-O-$ $b = 1-5, c = 2-5$ and NHS is N-hydroxysuccinimidyl. Upon hydrolysis, the resulting released active agent, e.g., protegrin peptide, will possess a short tag resulting from hydrolysis of the ester functionality of the polymer reagent. Illustrative releasable conjugates of this type include: mPEG-O—$(CH_2)_b$—$COOCH_2C(O)$—NH-protegrin peptide, and mPEG-O—$(CH_2)_b$—COO—$CH(CH_3)$—$CH_2$—C(O)—NH-protegrin peptide, where the number of water-soluble polymers attached to protegrin peptide can be anywhere from 1 to 4, or more preferably, from 1 to 3.

Carboxyl Coupling and Resulting Conjugates

Carboxyl groups represent another functional group that can serve as a point of attachment to the protegrin peptide. The conjugate will have the following structure:

PRO—C(O)—X-POLY where protegrin-C(O)~ corresponds to a residue of a protegrin peptide where the carbonyl is a carbonyl (derived from the carboxy group) of the protegrin peptide. X is a spacer moiety, such as a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing protegrin peptide. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linker structure.

Polymeric reagents containing a hydrazide moiety are also suitable for conjugation at a carbonyl. To the extent that the protegrin peptide does not contain a carbonyl moiety, a carbonyl moiety can be introduced by reducing any carboxylic acid functionality (e.g., the C-terminal carboxylic acid). Specific examples of polymeric reagents comprising a hydrazide moiety, along with the corresponding conjugates, are provided in Table 3, below. In addition, any polymeric reagent comprising an activated ester (e.g., a succinimidyl group) can be converted to contain a hydrazide moiety by reacting the polymer activated ester with hydrazine ($NH_2$—$NH_2$) or tert-butyl carbamate [$NH_2NHCO_2C(CH_3)_3$]. In the table, the variable (n) represents the number of repeating monomeric units and "═C-protegrin" represents a residue of a protegrin peptide following conjugation to the polymeric reagent were the underlined C is part of the protegrin peptide. Optionally, the hydrazone linkage can be reduced using a suitable reducing agent. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

Thiol Coupling and Resulting Conjugates

Thiol groups contained within the protegrin peptide can serve as effective sites of attachment for the water-soluble polymer. The thiol groups contained in cysteine residues of the protegrin peptide can be reacted with an activated PEG that is specific for reaction with thiol groups, e.g., an N-maleimidyl polymer or other derivative, as described in, for example, U.S. Pat. No. 5,739,208, WO 01/62827, and in Table 4 below. In certain embodiments, cysteine residues may be introduced in the protegrin peptide and may be used to attach a water-soluble polymer.

Specific examples of the reagents themselves, along with the corresponding conjugates, are provided in Table 4 below. In the table, the variable (n) represents the number of repeating monomeric units and "—S-protegrin" represents a residue of a protegrin peptide following conjugation to the water-soluble polymer, where the S represents the residue of a protegrin peptide thiol group. While each polymeric portion [e.g., $(OCH_2CH_2)_n$ or $(CH_2CH_2O)_n$] presented in Table 4 terminates in a "$CH_3$" group, other end-capping groups (such as H and benzyl) or reactive groups may be used as well.

TABLE 3

Carboxyl-Specific Polymeric Reagents and the protegrin Peptide Conjugates Formed Therefrom

| Polymeric Reagent | Corresponding Conjugate |
|---|---|
| 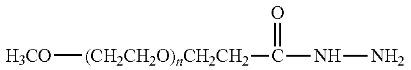 mPEG-Hydrazine Reagent | 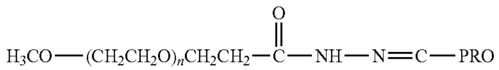 Hydrazone Linkage |
| 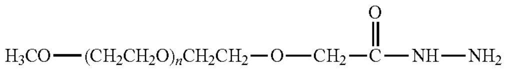 mPEG-Hydrazine Reagent | 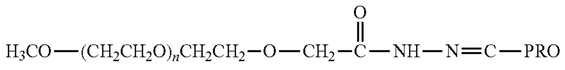 Hydrazone Linkage |
| 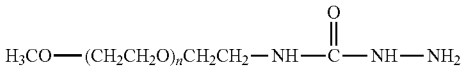 mPEG-Hydrazine Reagent | 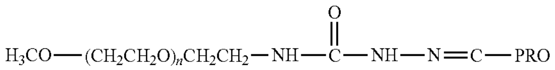 Hydrazone Linkage |
| 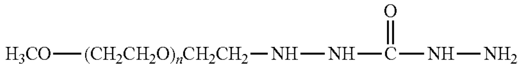 mPEG-Hydrazine Reagent | 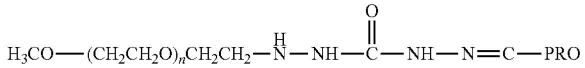 Hydrazone Linkage |
| 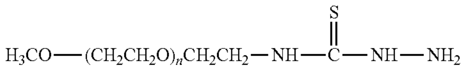 mPEG-Hydrazine Reagent | 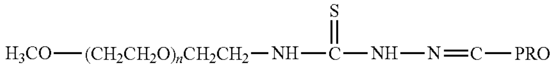 Hydrazone Linkage |
| 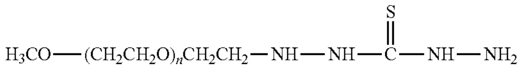 mPEG-Hydrazine Reagent | 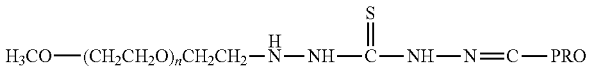 Hydrazone Linkage |
| 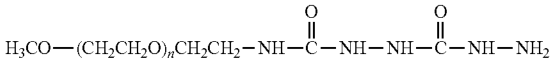 mPEG-Hydrazine Reagent | 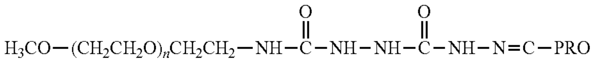 Hydrazone Linkage |
| 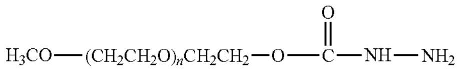 mPEG-Hydrazine Reagent | 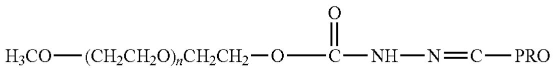 Hydrazone Linkage |

TABLE 4
Thiol-Specific Polymeric Reagents and the protegrin peptide Conjugates Formed Therefrom
| Polymeric Reagent | Corresponding Conjugate |
| --- | --- |
| 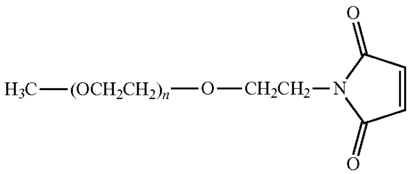 mPEG Maleimide Reagent | 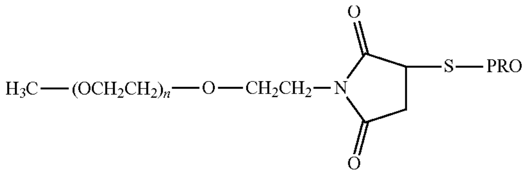 Thioether Linkage |
| 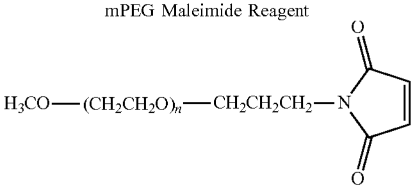 mPEG Maleimide Reagent | 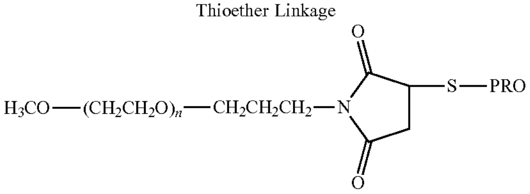 Thioether Linkage |
| 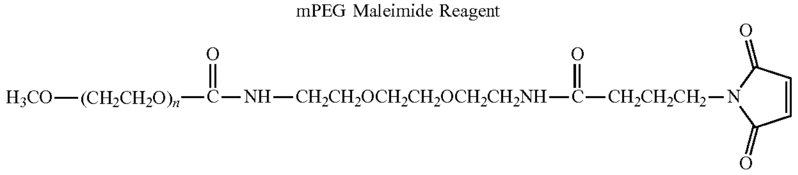 mPEG Maleimide Reagent | 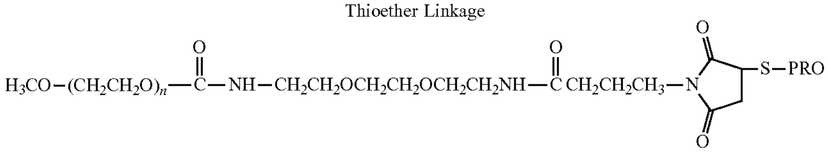 Thioether Linkage |
| 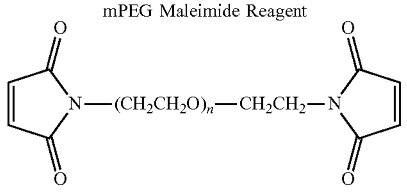 Homobifunctional mPEG Maleimide Reagent | 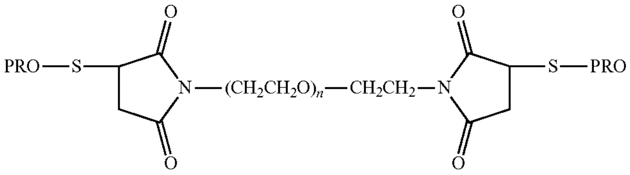 Thioether Linkages |

TABLE 4-continued
| Thiol-Specific Polymeric Reagents and the protegrin peptide Conjugates Formed Therefrom | |
|---|---|
| Polymeric Reagent | Corresponding Conjugate |
| 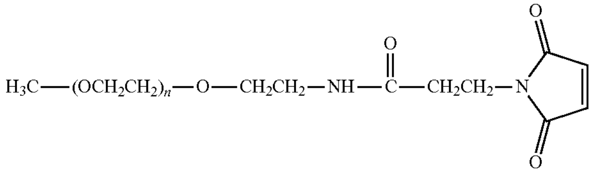 mPEG Maleimide Reagent | 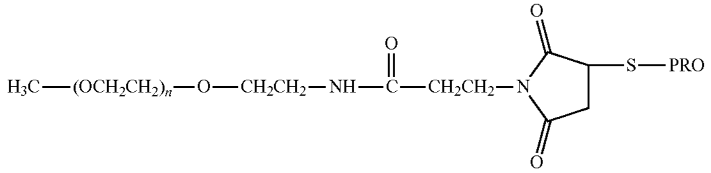 Thioether Linkage |
| 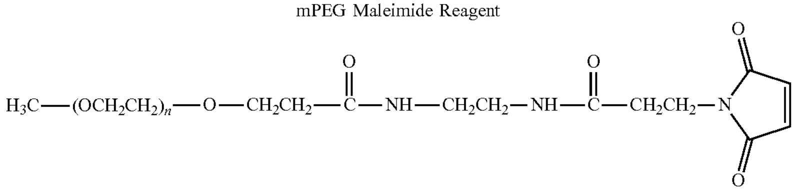 mPEG Maleimide Reagent | 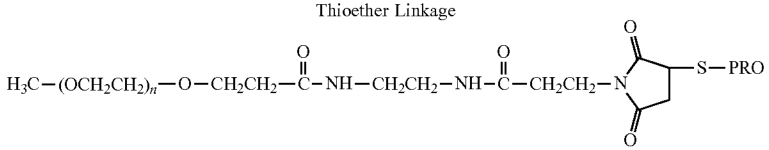 Thioether Linkage |
| 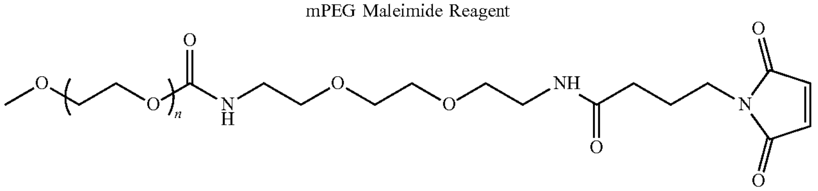 mPEG Maleimide Reagent | 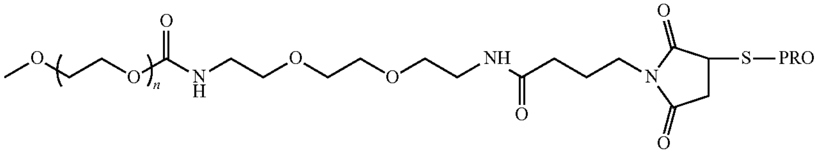 Thioether Linkage |

TABLE 4-continued
Thiol-Specific Polymeric Reagents and the protegrin peptide Conjugates Formed Therefrom
| Polymeric Reagent | Corresponding Conjugate |
| --- | --- |
| 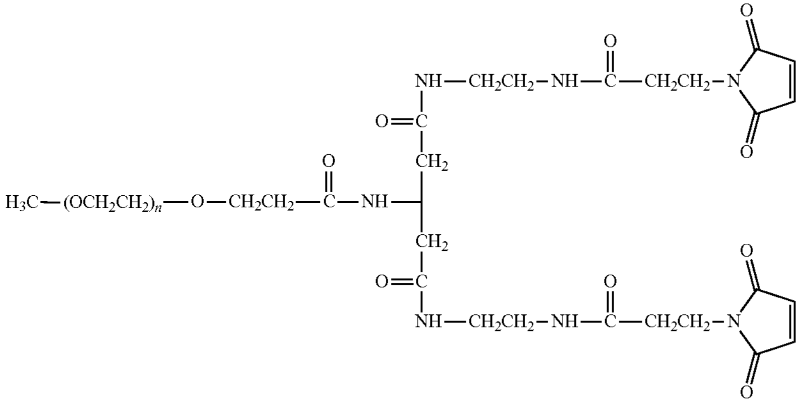<br>mPEG Forked Maleimide Reagent | 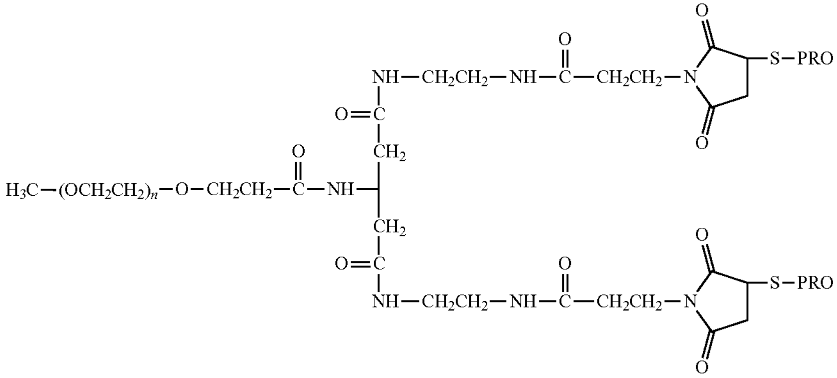<br>Thioether Linkage |
| 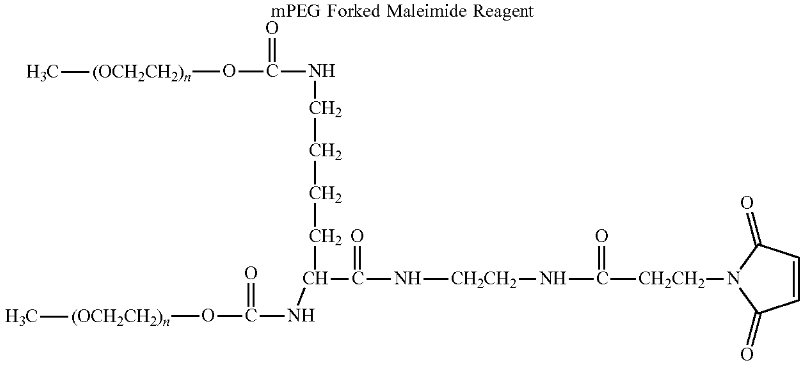<br>branched mPEG2 Maleimide Reagent | 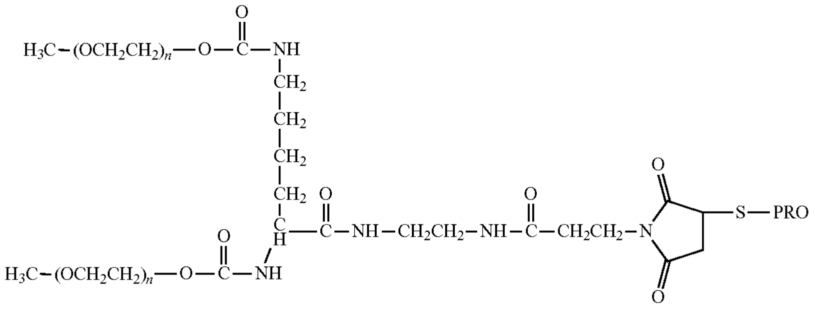<br>Thioether Linkage |
| 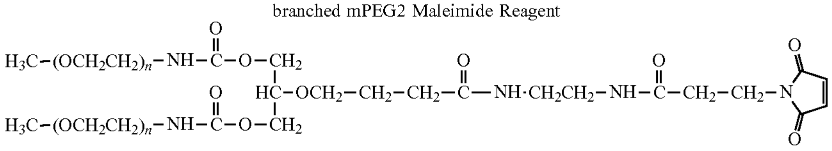<br>branched mPEG2 Maleimide Reagent | 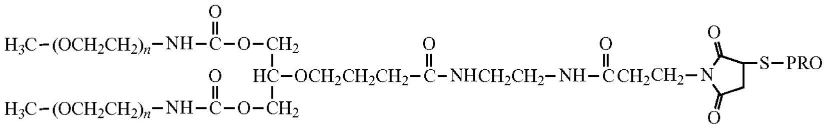<br>Thioether Linkage |

TABLE 4-continued
| Thiol-Specific Polymeric Reagents and the protegrin peptide Conjugates Formed Therefrom | |
|---|---|
| Polymeric Reagent | Corresponding Conjugate |
| 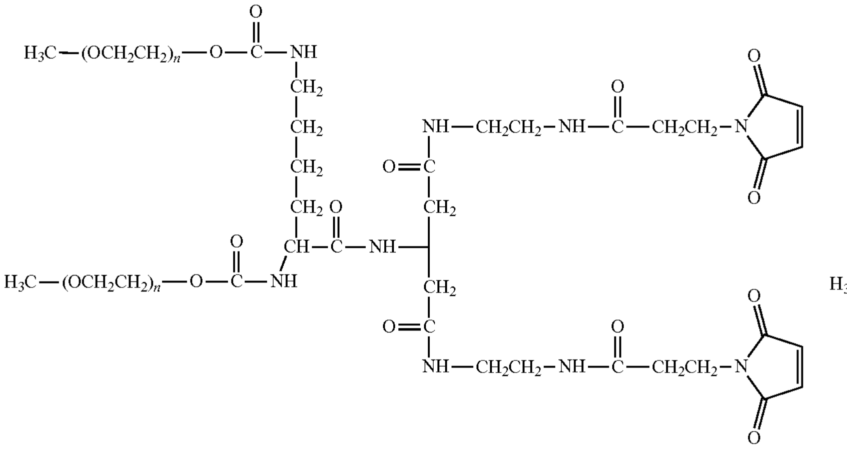<br>Branched mPEG2 Forked Maleimide Reagent | 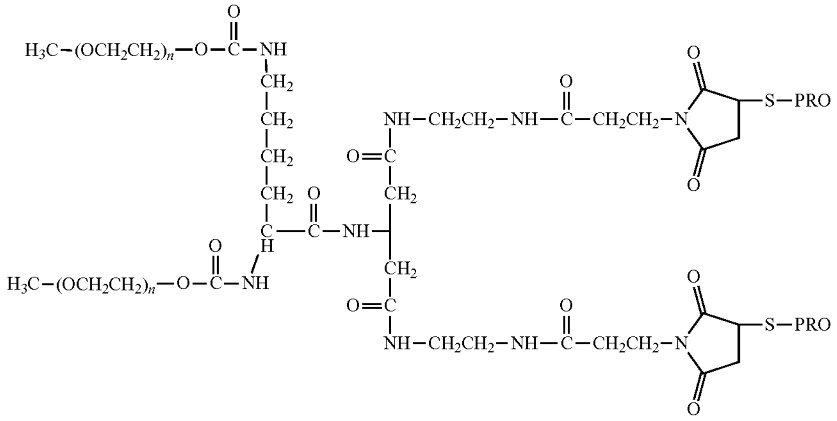<br>Thioether Linkages |
| 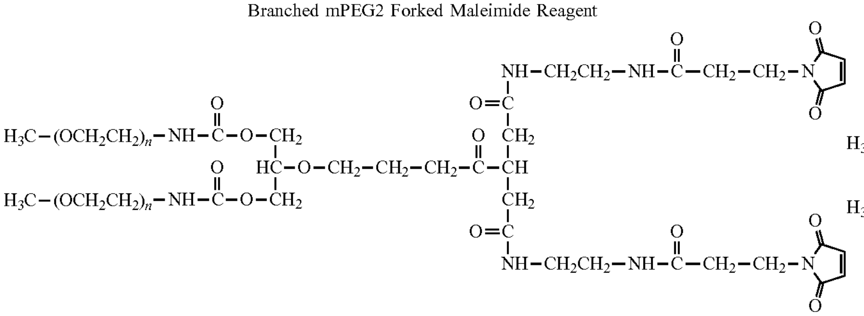<br>Branched mPEG2 Forked Maleimide Reagent | 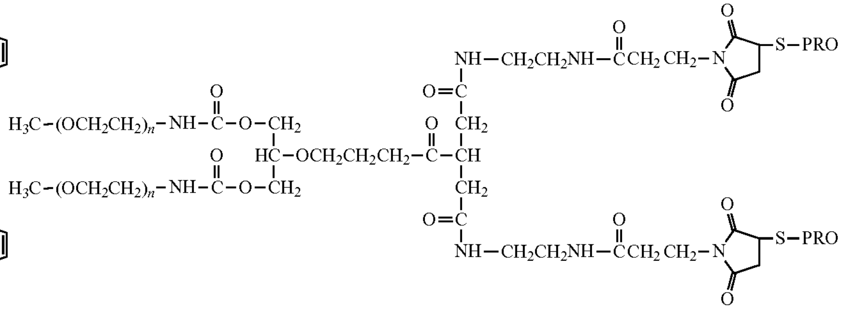<br>Thioether Linkages |
| 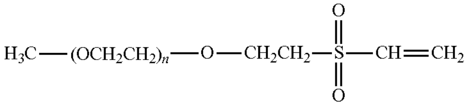<br>mPEG Vinyl Sulfone Reagent | 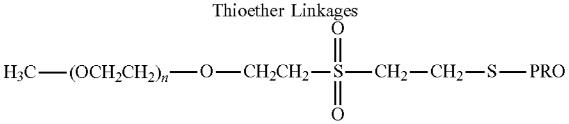<br>Thioether Linkage |

TABLE 4-continued
| Thiol-Specific Polymeric Reagents and the protegrin peptide Conjugates Formed Therefrom | |
|---|---|
| Polymeric Reagent | Corresponding Conjugate |
| 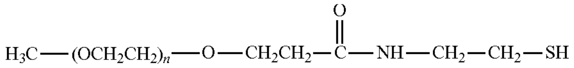 mPEG Thiol Reagent | 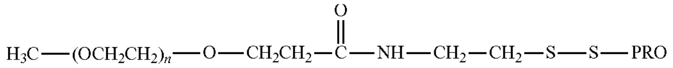 Disulfide Linkage |
| 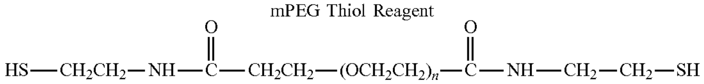 Homobifunctional PEG Thiol Reagent | 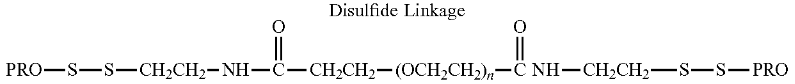 Disulfide Linkages |
| 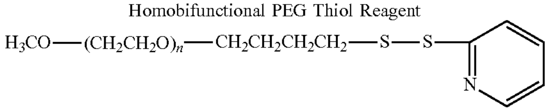 mPEG Disulfide Reagent | $H_3CO—(CH_2CH_2O)_n—CH_2CH_2CH_2CH_2—S—S—PRO$ Disulfide Linkage |

With respect to conjugates formed from water-soluble polymers bearing one or more maleimide functional groups (regardless of whether the maleimide reacts with an amine or thiol group on the protegrin peptide), the corresponding maleamic acid form(s) of the water-soluble polymer can also react with the protegrin peptide. Under certain conditions (e.g., a pH of about 7-9 and in the presence of water), the maleimide ring will "open" to form the corresponding maleamic acid. The maleamic acid, in turn, can react with an amine or thiol group of a protegrin peptide. Exemplary maleamic acid-based reactions are schematically shown below. POLY represents the water-soluble polymer, and ~S-protegrin represents a residue of a protegrin peptide, where the S is derived from a thiol group of the protegrin peptide.

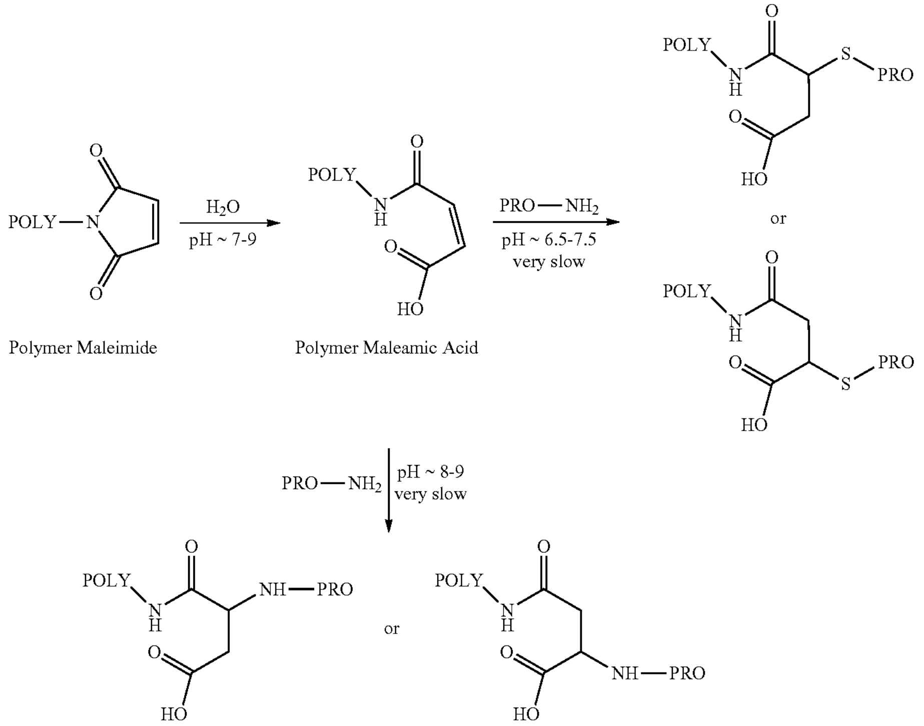

Polymer Maleimide

Polymer Maleamic Acid or or

Thiol PEGylation is specific for free thiol groups on the protegrin peptide. Typically, a polymer maleimide is conjugated to a sulfhydryl-containing protegrin peptide at pHs ranging from about 6-9 (e.g., at 6, 6.5, 7, 7.5, 8, 8.5, or 9), more preferably at pHs from about 7-9, and even more preferably at pHs from about 7 to 8. Generally, a slight molar excess of polymer maleimide is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer. Thiol-selective conjugation is preferably conducted at pHs around 7. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the protegrin peptide. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., protegrin peptide) undesired multi-conjugated species, and free or unreacted polymer. The resulting conjugates can then be further characterized using analytical methods such as MALDI, capillary electrophoresis, gel electrophoresis, and/or chromatography.

An illustrative protegrin peptide conjugate formed by reaction with one or more protegrin peptide thiol groups may possess the following structure:

$$POLY\text{-}X_{0,1}\text{—}C(O)Z\text{—}Y\text{—}S\text{—}S\text{-}PRO$$

where POLY is a water-soluble polymer, X is an optional linker, Z is a heteroatom selected from the group consisting of O, NH, and S, and Y is selected from the group consisting of $C_{2-10}$ alkyl. $C_{2-10}$ substituted alkyl, aryl, and substituted aryl, and ~S-PRO is a residue of a protegrin peptide, where the S represents the residue of a protegrin peptide thiol group. Such polymeric reagents suitable for reaction with a protegrin peptide to result in this type of conjugate are described in U.S. Patent Application Publication No. 2005/0014903, which is incorporated herein by reference.

With respect to polymeric reagents suitable for reacting with a protegrin peptide thiol group, those described here and elsewhere can be obtained from commercial sources. In addition, methods for preparing polymeric reagents are described in the literature.

Additional Conjugates and Features Thereof

As is the case for any protegrin peptide polymer conjugate of the invention, the attachment between the protegrin peptide and water-soluble polymer can be direct, wherein no intervening atoms are located between the protegrin peptide and the polymer, or indirect, wherein one or more atoms are located between the protegrin peptide and polymer. With respect to the indirect attachment, a "spacer moiety or linker" serves as a link between the protegrin peptide and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties (including "X", $X^1$, $X^2$, and $X^3$) include those selected from the group consisting of —O—, —S—, —S—S—, C(O)—, —C(O)O—, —OC(O)—, —$CH_2$—C(O)O—, —$CH_2$—OC(O)—, —C(O)O—$CH_2$—, —OC(O)—$CH_2$—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—C $H_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—C(O)—NH—$CH_2$—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—. —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—C $H_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —O—C(O)—NH—[C $H_2]_h$—$(OCH2CH2)_j$—, bivalent cycloalkyl group, —O—, —S—, an amino acid, —$N(R^6)$—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—$(CH_2)_{1-6}$—NH—C(O)—, —NH—C(O)—NH—$(CH_2)_{1-6}$—NH—C(O)—, and —O—C(O)—NH—$(CH_2)_{1-6}$—NH—C(O)—, wherein the subscript values following each methylene indicate the number of methylenes contained in the structure, e.g., $(CH_2)_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —$(CH_2CH_2O)_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

As indicated above, in some instances the water-soluble polymer-(protegrin) conjugate will include a non-linear water-soluble polymer. Such a non-linear water-soluble polymer encompasses a branched water-soluble polymer (although other non linear water-soluble polymers are also contemplated). Thus, in one or more embodiments of the invention, the conjugate comprises a protegrin peptide covalently attached, either directly or through a spacer moiety comprised of one or more atoms, to a branched water-soluble polymer, at in a non-limiting example, an internal or N-terminal amine. As used herein, an internal amine is an amine that is not part of the N-terminal amino acid (meaning not only the N-terminal amine, but any amine on the side chain of the N-terminal amino acid).

Although such conjugates include a branched water-soluble polymer attached (either directly or through a spacer moiety) to a protegrin peptide at an internal amino acid of the protegrin peptide, additional branched water-soluble polymers can also be attached to the same protegrin peptide at other locations as well. Thus, for example, a conjugate including a branched water-soluble polymer attached (either directly or through a spacer moiety) to a protegrin peptide at an internal amino acid of the protegrin peptide, can further include an additional branched water-soluble polymer covalently attached, either directly or through a spacer moiety comprised of one or more atoms, to the N-terminal amino acid residue, such as at the N-terminal amine.

One preferred branched water-soluble polymer comprises the following structure:

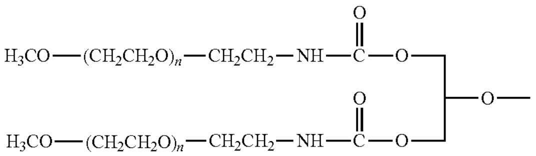

wherein each (n) is independently an integer having a value of from 3 to 4000, or more preferably, from about 10 to 1800.

Also forming part of the invention are multi-armed polymer conjugates comprising a polymer scaffold having 3 or more polymer arms each suitable for capable of covalent attachment of a protegrin peptide.

Exemplary conjugates in accordance with this embodiment of the invention will generally comprise the following structure:

$$R\text{-}(\text{-POLY—X-PRO})_y$$

wherein R is a core molecule as previously described, POLY is a water-soluble polymer, X is a cleavable, e.g., hydrolyzable linkage, and y ranges from about 3 to 15.

More particularly, such a conjugate may comprise the structure:

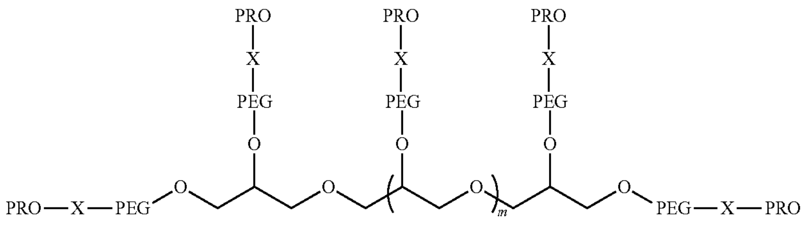

where m is selected from 3, 4, 5, 6, 7, and 8.

In yet a related embodiment, the protegrin peptide conjugate may correspond to the structure:

$$R-(POLY-X-O-PRO)_y$$

where R is a core molecule as previously described, X is —NH—P—Z—C(O) P is a spacer, Z is —O—, —NH—, or —$CH_2$—, —O-PRO is a hydroxyl residue of a protegrin peptide, and y is 3 to 15. Preferably, X is a residue of an amino acid.

Purification

The protegrin peptide polymer conjugates described herein can be purified to obtain/isolate different conjugate species. Specifically, a product mixture can be purified to obtain an average of anywhere from one, two, or three or even more PEGs per protegrin peptide. In one embodiment of the invention, preferred protegrin peptide conjugates are mono-conjugates. The strategy for purification of the final conjugate reaction mixture will depend upon a number of factors, including, for example, the molecular weight of the polymeric reagent employed, the protegrin peptide, and the desired characteristics of the product—e.g., monomer, dimer, particular positional isomers, etc.

If desired, conjugates having different molecular weights can be isolated using gel filtration chromatography and/or ion exchange chromatography. Gel filtration chromatography may be used to fractionate different protegrin peptide conjugates (e.g., 1-mer, 2-mer, 3-mer, and so forth, wherein "1-mer" indicates one polymer molecule per protegrin peptide, "2-mer" indicates two polymers attached to protegrin peptide, and so on) on the basis of their differing molecular weights (where the difference corresponds essentially to the average molecular weight of the water-soluble polymer). While this approach can be used to separate PEG and other protegrin peptide polymer conjugates having different molecular weights, this approach is generally ineffective for separating positional isomers having different polymer attachment sites within the protegrin peptide. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) or other functional groups of the protegrin peptide.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem,* 107: 60-63), and (iv) sodium dodecyl sulfate polyacrylamide gel electrophoresis (SDS PAGE), followed by staining with barium iodide.

Separation of positional isomers is typically carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose™ ion exchange column available from Amersham Biosciences. Either approach can be used to separate polymer-protegrin peptide isomers having the same molecular weight (positional isomers).

The resulting purified compositions are preferably substantially free of the non-conjugated protegrin peptide. In addition, the compositions preferably are substantially free of all other non-covalently attached water-soluble polymers.

Compositions

Compositions of Conjugate Isomers

Also provided herein are compositions comprising one or more of the protegrin peptide polymer conjugates described herein. In certain instances, the composition will comprise a plurality of protegrin peptide polymer conjugates. For instance, such a composition may comprise a mixture of protegrin peptide polymer conjugates having one, two, three and/or even four water-soluble polymer molecules covalently attached to sites on the protegrin peptide. That is to say, a composition of the invention may comprise a mixture of monomer, dimer, and possibly even trimer or 4-mer. Alternatively, the composition may possess only mono-conjugates, or only di-conjugates, etc. A mono-conjugate protegrin peptide composition will typically comprise protegrin peptide moieties having only a single polymer covalently attached thereto, e.g., preferably releasably attached. A mono-conjugate composition may comprise only a single positional isomer, or may comprise a mixture of different positional isomers having polymer covalently attached to different sites within the protegrin peptide.

In yet another embodiment, a protegrin peptide conjugate may possess multiple protegrin peptides covalently attached to a single multi-armed polymer having 3 or more polymer arms. Typically, the protegrin peptide moieties are each attached at the same protegrin peptide amino acid site, e.g., the N-terminus.

With respect to the conjugates in the composition, the composition will typically satisfy one or more of the following characteristics: at least about 85% of the conjugates in the composition will have from one to four polymers attached to the protegrin peptide; at least about 85% of the conjugates in the composition will have from one to three polymers attached to the protegrin peptide; at least about 85% of the conjugates in the composition will have from one to two polymers attached to the protegrin peptide; or at least about 85% of the conjugates in the composition will have one polymer attached to the protegrin peptide (e.g., be monoPEGylated); at least about 95% of the conjugates in the composition will have from one to four polymers attached to the protegrin peptide; at least about 95% of the conjugates in the composition will have from one to three polymers attached to the protegrin peptide; at least about 95% of the conjugates in the composition will have from one to two polymers attached to the protegrin peptide; at least about 95% of the conjugates in the composition will have one polymers attached to the protegrin peptide; at least about 99% of the conjugates in the composition will have from one to four polymers attached to the protegrin peptide; at least about 99% of the conjugates in the composition will have from one to three polymers attached to the protegrin peptide; at least about 99% of the conjugates in the composition will have from one to two polymers attached to the protegrin peptide; and at least about 99% of the conjugates in the composition will have one polymer attached to the protegrin peptide (e.g., be monoPEGylated).

In one or more embodiments, the conjugate-containing composition is free or substantially free of albumin.

In one or more embodiments of the invention, a pharmaceutical composition is provided comprising a conjugate comprising a protegrin peptide covalently attached, e.g., releasably, to a water-soluble polymer, wherein the water-soluble polymer has a weight-average molecular weight of greater than about 2,000 Daltons; and a pharmaceutically acceptable excipient.

Control of the desired number of polymers for covalent attachment to protegrin peptide is achieved by selecting the proper polymeric reagent, the ratio of polymeric reagent to the protegrin peptide, temperature, pH conditions, and other aspects of the conjugation reaction. In addition, reduction or elimination of the undesired conjugates (e.g., those conjugates having four or more attached polymers) can be achieved through purification mean as previously described.

For example, the water-soluble polymer-(protegrin peptide) conjugates can be purified to obtain/isolate different conjugated species. Specifically, the product mixture can be purified to obtain an average of anywhere from one, two, three, or four PEGs per protegrin peptide, typically one, two or three PEGs per protegrin peptide. In one or more embodiments, the product comprises one PEG per protegrin peptide, where PEG is releasably (via hydrolysis) attached to PEG polymer, e.g., a branched or straight chain PEG polymer.

Pharmaceutical Compositions

Optionally, a protegrin peptide conjugate composition of the invention will comprise, in addition to the protegrin peptide conjugate, a pharmaceutically acceptable excipient. More specifically, the composition may further comprise excipients, solvents, stabilizers, membrane penetration enhancers, etc., depending upon the particular mode of administration and dosage form.

Pharmaceutical compositions of the invention encompass all types of formulations and in particular those that are suited for injection, e.g., powders or lyophilates that can be reconstituted as well as liquids, as well as for inhalation. Examples of suitable diluents for reconstituting solid compositions prior to injection include bacteriostatic endotoxin-free water for injection, dextrose 5% in water, phosphate-buffered saline, Ringer's solution, saline, sterile water, deionized water, and combinations thereof. With respect to liquid pharmaceutical compositions, solutions and suspensions are envisioned.

Exemplary pharmaceutically acceptable excipients include, without limitation, carbohydrates, inorganic salts, antimicrobial agents, antioxidants, surfactants, buffers, acids, bases, and combinations thereof.

Representative carbohydrates for use in the compositions of the present invention include sugars, derivatized sugars such as alditols, aldonic acids, esterified sugars, and sugar polymers. Exemplary carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred, in particular for formulations intended for inhalation, are non-reducing sugars, sugars that can form a substantially dry amorphous or glassy phase when combined with the composition of the present invention, and sugars possessing relatively high glass transition temperatures, or Tgs (e.g., Tgs greater than 40° C., or greater than 50° C., or greater than 60° C., or greater than 70° C., or having Tgs of 80° C. and above). Such excipients may be considered glass-forming excipients.

Additional excipients include amino acids, peptides and particularly oligomers comprising 2-9 amino acids, or 2-5 mers, and polypeptides, all of which may be homo or hetero species.

Exemplary protein excipients include albumins such as human serum albumin (HSA), recombinant human albumin (rHA), gelatin, casein, hemoglobin, and the like. The compositions may also include a buffer or a pH-adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate, and phosphate. Amino acids such as glycine are also suitable.

The compositions of the present invention may also include one or more additional polymeric excipients/additives, e.g., polyvinylpyrrolidones, derivatized celluloses such as hydroxymethylcellulose, hydroxyethylcellulose, and hydroxypropylmethylcellulose, FICOLLs (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., zinc and other such suitable cations). The use of certain di-substituted phosphatidylcholines for producing perforated microstructures (i.e., hollow, porous microspheres) may also be employed.

Other pharmaceutical excipients and/or additives suitable for use in the compositions according to the present invention are listed in "Remington: The Science & Practice of Pharmacy," 21st ed., Williams & Williams, (2005), and in the "Physician's Desk Reference," 60th ed., Medical Economics, Montvale, N.J. (2006).

The amount of the protegrin peptide conjugate (i.e., the conjugate formed between the active agent and the polymeric reagent) in the composition will vary depending on a number of factors, but will optimally be a therapeutically effective amount when the composition is stored in a unit dose container (e.g., a vial). In addition, a pharmaceutical preparation, if in solution form, can be housed in a syringe. A therapeutically effective amount can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient or excipients will be present in the composition in an amount of about 1% to about 99% by weight, from about 5% to about 98% by weight, from about 15 to about 95% by weight of the excipient, or with concentrations less than 30% by weight. In general, a high concentration of the protegrin peptide is desired in the final pharmaceutical formulation.

Combination of Actives

A composition of the invention may also comprise a mixture of water-soluble polymer-(protegrin peptide) conjugates and unconjugated protegrin peptide, to thereby provide a mixture of fast-acting and long-acting protegrin peptide.

Additional pharmaceutical compositions in accordance with the invention include those comprising, in addition to an extended-action protegrin peptide water-soluble polymer conjugate as described herein, a rapid acting protegrin peptide polymer conjugate where the water-soluble polymer is releasably attached to a suitable location on the protegrin peptide.

Administration

The protegrin peptide conjugates of the invention can be administered by any of a number of routes including without limitation, oral, rectal, nasal, topical (including transdermal, aerosol, buccal and sublingual), vaginal, parenteral (including subcutaneous, intramuscular, intravenous and intradermal), intrathecal, and pulmonary. Preferred forms of administration include parenteral and pulmonary. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

In some embodiments of the invention, the compositions comprising the peptide-polymer conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and US Patent Applications Nos. 2005/0281781, and 2008/0044438.

In one or more embodiments of the invention, a method is provided, the method comprising delivering a conjugate to a patient, the method comprising the step of administering to the patient a pharmaceutical composition comprising a protegrin peptide polymer conjugate as provided herein. Administration can be effected by any of the routes herein described. The method may be used to treat a patient suffering from a condition that is responsive to treatment with protegrin peptide by administering a therapeutically effective amount of the pharmaceutical composition.

As previously stated, the method of delivering a protegrin peptide polymer conjugate as provided herein may be used to treat a patient having a condition that can be remedied or prevented by administration of protegrin peptide.

Certain conjugates of the invention, e.g., releasable conjugates, include those effective to release the protegrin peptide, e.g., by hydrolysis, over a period of several hours or even days (e.g., 2-7 days, 2-6 days, 3-6 days, 3-4 days) when evaluated in a suitable in-vivo model.

The actual dose of the protegrin peptide conjugate to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a conjugate of the invention will be delivered such that plasma levels of a protegrin peptide are within a range of about 0.5 picomoles/liter to about 500 picomoles/liter. In certain embodiments the conjugate of the invention will be delivered such that plasma leves of a protegrin peptide are within a range of about 1 picomoles/liter to about 400 picomoles/liter, a range of about 2.5 picomoles/liter to about 250 picomoles/liter, a range of about 5 picomoles/liter to about 200 picomoles/liter, or a range of about 10 picomoles/liter to about 100 picomoles/liter.

On a weight basis, a therapeutically effective dosage amount of a protegrin peptide conjugate as described herein will range from about 0.01 mg per day to about 1000 mg per day for an adult. For example, dosages may range from about 0.1 mg per day to about 100 mg per day, or from about 1.0 mg per day to about 10 mg/day. On an activity basis, corresponding doses based on international units of activity can be calculated by one of ordinary skill in the art.

The unit dosage of any given conjugate (again, such as provided as part of a pharmaceutical composition) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. Reagents and materials are commercially available unless specifically stated to the contrary. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Although other abbreviations known by one having ordinary skill in the art will be referenced, other reagents and materials will be used, and other methods known by one having ordinary skill in the art will be used, the following list and methods description is provided for the sake of convenience.

ABBREVIATIONS mPEG-SPA mPEG-succinimidyl propionate
mPEG-SPC mPEG-succinimidyl phenyl carbonate
mPEG-SBA mPEG-succinimidyl butanoate
mPEG-OPSS mPEG-orthopyridyl-disulfide
mPEG-MAL mPEG-maleimide, $CH_3O—(CH_2CH_2O)_n—CH_2CH_2$-MAL
mPEG-SMB mPEG-succinimidyl α-methylbutanoate, $CH_3O—(CH_2CH_2O)—CH_2CH_2—CH(CH_3)—C(O)—O$-succinimide
mPEG-ButyrALD $H_3O—(CH_2CH_2O)_n—CH_2CH_2—O—C(O)—NH—(CH_2CH_2O)_4—CH_2CH_2CH_2C(O)H$
mPEG-PIP $CH_3O—(CH_2CH_2O)_n—CH_2CH_2—C(O)$-piperidin-4-one
mPEG-CM $CH_3O—(CH_2CH_2O)_n—CH_2CH_2—O—CH_2—C(O)—OH)$
anh. Anhydrous
CV column volume
Fmoc 9-fluorenylmethoxycarbonyl
$NaCNBH_3$ sodium cyanoborohydride
HCl hydrochloric acid
HEPES 4-(2-hydroxyethyl)-1-piperazineethanesulfonic acid
NMR nuclear magnetic resonance
DCC 1,3-dicyclohexylcarbodiimide
DMF dimethylformamide
DMSO dimethyl sulfoxide
DI deionized
MW molecular weight
K or kDa kilodaltons
SEC Size exclusion chromatography
HPLC high performance liquid chromatography
FPLC fast protein liquid chromatography
SDS-PAGE sodium dodecyl sulfate-polyacrylamide gel electrophoresis
MALDI-TOF Matrix Assisted Laser Desorption Ionization Time-of-Flight
TLC Thin Layer Chromatography
THF Tetrahydrofuran Materials All PEG reagents referred to in the appended examples are commercially available unless otherwise indicated.

mPEG Reagent Preparation

Typically, a water-soluble polymer reagent is used in the preparation of peptide conjugates of the invention. For purposes of the present invention, a water-soluble polymer reagent is a water-soluble polymer-containing compound having at least one functional group that can react with a functional group on a peptide (e.g., the N-terminus, the C-terminus, a functional group associated with the side chain of an amino acid located within the peptide) to create a covalent bond. Taking into account the known reactivity of the functional group(s) associated with the water-soluble polymer reagent, it is possible for one of ordinary skill in the art to determine whether a given water-soluble polymer reagent will form a covalent bond with the functional group(s) of a peptide.

Representative polymeric reagents and methods for conjugating such polymers to an active moiety are known in the art, and are, e.g., described in Harris, J. M. and Zalipsky. S., eds, *Poly(ethylene glycol). Chemistry and Biological Applications*, ACS, Washington, 1997; Veronese, F., and J. M Harris, eds., *Peptide and Protein PEGylation*, Advanced Drug Delivery Reviews, 54(4); 453-609 (2002); Zalipsky, S., et al., "*Use of Functionalized Poly(Ethylene glycols) for Modification of Polypeptides*" in *Polyethylene Glycol Chemistry: Biotechnical and Biomedical Applications*, J. M. Harris, ed., Plenus Press, New York (1992); Zalipsky (1995) *Advanced Drug Reviews* 16:157-182, and in Roberts, et al. *Adv. Drug Delivery Reviews,* 54, 459-476 (2002).

Additional PEG reagents suitable for use in forming a conjugate of the invention, and methods of conjugation are described in Shearwater Corporation, Catalog 2001; Shearwater Polymers, Inc., Catalogs, 2000 and 1997-1998, and in Pasut. G., et al., *Expert Opin. Ther. Patents* (2004), 14(5). PEG reagents suitable for use in the present invention also include those available from NOF Corporation (Tokyo, Japan), as described generally on the NOF website (2006) under Products, High Purity PEGs and Activated PEGs. Products listed therein and their chemical structures are expressly incorporated herein by reference. Additional PEGs for use in forming a GLP-1 conjugate of the invention include those available from Polypure (Norway) and from QuantaBioDesign LTD (Powell, Ohio), where the contents of their online catalogs (2006) with respect to available PEG reagents are expressly incorporated herein by reference.

In addition, water-soluble polymer reagents useful for preparing peptide conjugates of the invention is prepared synthetically. Descriptions of the water-soluble polymer reagent synthesis can be found in, for example, U.S. Pat. Nos. 5,252,714, 5,650,234, 5,739,208, 5,932,462, 5,629,384, 5,672,662, 5,990,237, 6,448,369, 6,362,254, 6,495,659, 6,413,507, 6,376,604, 6,348,558, 6,602,498, and 7,026,440.

Example PRO1

Protegrin-mPEG Conjugates a) mPEG-$N^{ter}$-Protegrin via mPEG-SPC

Protegrin is prepared and purified according to standard automated peptide synthesis or recombinant techniques known to those skilled in the art. An illustrative polymeric reagent, mPEG-SPC reagent,

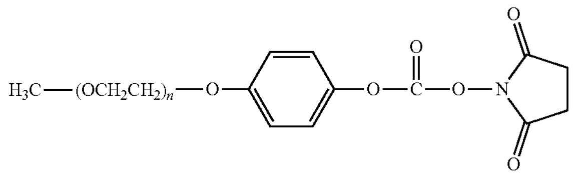

'SPC' polymer reagent is covalently attached to the N-terminus of protegrin, to provide a 1N-conjugate form of the peptide. mPEG-SPC 20 kDa, stored at −20° C. under argon, is warmed to ambient temperature. The reaction is performed at room temperature. An X-fold molar excess of mPEG-SPC 20 kDa reagent is used based upon absolute peptide content. The mPEG-SPC reagent is weighed into a glass vial containing a magnetic stirrer bar. A solution of Protegrin prepared in phosphate buffered saline, PBS, pH 7.4 is added and the mixture is stirred using a magnetic stirrer until the mPEG-SPC is fully dissolved. The stirring speed is reduced and the reaction is allowed to proceed to formation of conjugate product. The reaction is optionally quenched to terminate the reaction. The pH of the conjugate solution at the end of the reaction is measured and further acidified by addition of 0.1M HCl, if necessary, to bring the pH of the final solution to about 5.5. The conjugate solution is then analyzed by SDS-PAGE and RP-HPLC (C18) to determine the extent of mPEG-$N^{ter}$-Protegrin conjugate formation.

Using this same approach, other conjugates are prepared using mPEG derivatives having other weight-average molecular weights that also bear an N-hydroxysuccinimide moiety.

b) Protegrin-$C^{ter}$-mPEG

An illustrative polymeric reagent, mPEG-$NH_2$ reagent is covalently attached to the C-terminus of protegrin, to provide a $C^{ter}$-conjugate form of the peptide. For coupling to the C-terminus, a protected Protegrin (Prot-protegrin) is prepared and purified according to standard automated peptide synthesis techniques known to those skilled in the art. mPEG-$NH_2$ 20 kDa, stored at −20° C. under argon, is warmed to ambient temperature. The reaction is performed at room temperature. A X-fold molar excess of mPEG-$NH_2$. PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$, PyBOP, HOBt are weighed into a glass vial containing a magnetic stirrer bar. A solution of Prot-protegrin is prepared in N. N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot-Protegrin-$C^{ter}$-mPEG conjugate formation. The remaining protecting groups are removed under standard deprotection conditions to yield the protegrin-$C^{ter}$-mPEG conjugate.

Using this same approach, other conjugates are prepared using mPEG derivatives having other weight-average molecular weights that also bear an amino moiety.

c) Protegrin-Cys(S-mPEG)

mPEG-Maleimide is obtained having a molecular weight of 5 kDa and having the basic structure shown below:

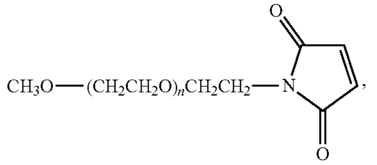

mPEG-MAL, 5 kDa

Protegrin, which has a thiol-containing cysteine residue, is dissolved in buffer. To this peptide solution is added a 3-5 fold molar excess of mPEG-MAL, 5 kDa. The mixture is stirred at room temperature under an inert atmosphere for several hours. Analysis of the reaction mixture reveals successful conjugation of this peptide.

Using this same approach, other conjugates are prepared using mPEG-MAL having other weight average molecular weights.

d) mPEG-$N^{ter}$-Protegrin via mPEG-SMB

An mPEG-N-Hydroxysuccinimide is obtained having a molecular weight of 5 kDa and having the basic structure shown below:

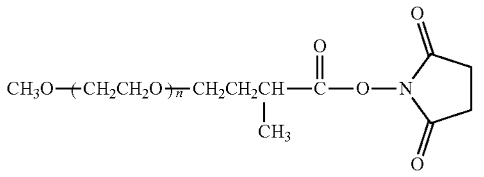

(mPEG-Succinimidyl α-Methylbutanoate Derivative, 5 kDa ("mPEG-SMB"))

mPEG-SMB, 5 kDa, stored at −20° C. under argon, is warmed to ambient temperature. A five-fold excess (relative to the amount of the peptide) of the warmed mPEG-SMB is dissolved in buffer to form a 10% reagent solution. The 10% reagent solution is quickly added to the aliquot of a stock protegrin solution and mixed well. After the addition of the mPEG-SMB, the pH of the reaction mixture is determined and adjusted to 6.7 to 6.8 using conventional techniques. To allow for coupling of the mPEG-SMB to the peptide via an amide linkage, the reaction solution is stirred for several hours (e.g., 5 hours) at room temperature in the dark or stirred overnight at 3-8° C. in a cold room, thereby resulting in a conjugate solution. The reaction is quenched with a 20-fold molar excess (with respect to the peptide) of Tris buffer.

Using this same approach, other conjugates are prepared using mPEG derivatives having other weight-average molecular weights that also bear an N-hydroxysuccinimide moiety.

e) Protegrin-Glu(O-mPEG)

An illustrative polymeric reagent, mPEG-$NH_2$ reagent is covalently attached to the Glu residue of Protegrin, to provide a Glu-conjugate form of the peptide. For coupling to the Glu residue, a protected Protegrin (Prot2-Protegrin) is prepared and purified according to standard automated peptide synthesis techniques known to those skilled in the art. Deprotection of the Glu(OBz) residue ($H_2$/Pd) yields the free-Glu carboxylate for subsequent coupling. mPEG-$NH_2$ 20 kDa, stored at −20° C. under argon, is warmed to ambient temperature. The reaction is performed at room temperature. A 5-fold molar excess of mPEG-$NH_2$, PyBOP (benzotriazol-1-yloxy)tripyrrolidinonophosphonium hexafluorophosphate), and 1-hydroxybenzotriazole (HOBt) are used, based upon absolute peptide content. The mPEG-$NH_2$. PyBOP. HOBt are weighed into a glass vial containing a magnetic stirrer bar. A solution of Prot3-Protegrin is prepared in N,N-dimethylformamide is added and the mixture is stirred using a magnetic stirrer until the mPEG-$NH_2$ is fully dissolved. The stirring speed is reduced and the reaction is allowed to proceed to formation of conjugate product. The conjugate solution is then analyzed by SDS-PAGE and RP-HPLC (C18) to determine the extent of Prot3-Protegrin-(Glu-O-mPEG) conjugate formation. The remaining protecting groups are removed under standard deprotection conditions to yield the Protegrin-Glu(O-mPEG) conjugate.

Using this same approach, other conjugates are prepared using mPEG derivatives having other weight-average molecular weights that also bear an amino moiety.

Example PRO2

PEGylation of Protegrin-1 (PG-1) with [mPEG2-CAC-FMOC-NHS-40K]

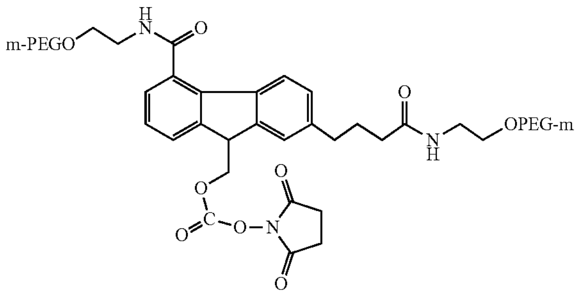

Stock solutions of 5.0 mg/mL PG-1 and 200 mG/mL mPEG2-CAC-FMOC-NHS-40K were prepared in 2 mM HCl. To initiate a reaction, the two stock solutions and a 0.5 M MES, pH 6.0, stock solution were brought to 25° C. and the three stock solutions were mixed (PEG reagent added last) to give final concentrations of 1.0 mg/mLPG-1, 50 mM MES and a 5-fold molar excess of mPEG2-CAC-FMOC-NHS-40K over PG-1. After 3.5 hours at 25° C. the reaction was quenched with 100 mM glycine in 100 mM HCl (10 mM final glycine concentration) for 1 hour. The reaction mixture was then diluted with deionized sterile water until the conductivity was below 1.0 mS/cm and the pH was adjusted to 6.0 with 1 M $Na_2CO_3$/$NaHCO_3$, pH 10.0.

The mono-PEGylated conjugate was purified from the reaction mixture by cation exchange chromatography using a column packed with SPHP media (GE Healthcare) on an AKTA Explorer 100 system (GE Healthcare). Buffer A was 20 mM MES, pH 6.0; Buffer B was 20 mM MES and 1 M NaCl, pH 6.0. The AKTA Explorer plumbing system and SPHP column were sanitized with 1 M HCl and 1 M NaOH and the resin was equilibrated with 10 column volumes Buffer A prior to sample loading. After loading, the column was washed with 10 column volumes 80% A/20% B to remove un-reacted PEG reagent. PEGylated and nonPEGylated peptides were eluted using a linear gradient from 80% A/20% B to 0% A/100% B over 20 column volumes with a linear flow rate of 90 cm/hour.

Fractions collected during cation exchange chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 20% B and conjugate separation was achieved using the gradient timetable shown in Table PRO2.1.

| Step | Time (min) | % Mobile phase B |
|---|---|---|
| 1 | 0.00 | 20.0 |
| 2 | 2.00 | 30.0 |
| 3 | 5.00 | 45.0 |
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Fractions containing pure mono-[mPEG2-CAC-FMOC-40K]-[PG-1] as determined by RP-HPLC were pooled. Glacial acetic acid was added to the pooled fractions to a final concentration of 5% (v/v) and loaded onto a CG71 S column (Rohm Haas) for Endotoxin removal and buffer exchange. Prior to sample loading, the column had been washed with 5% acetic acid in acetonitrile and equilibrated with 5% acetic acid in water (v/v). After sample loading, the column was washed with 10 column volumes of 5% acetic acid and mono-[mPEG2-CAC-FMOC-40K]-[PG-1] was eluted with a linear 0-100% gradient from 5% acetic acid to 5% acetic acid/95% Acetonitrile (vv) over 10 column volumes. Fractions containing the conjugate as determined by analytical reversed phase HPLC, were pooled, lyophilized and stored at −80° C.

A typical SPHP cation exchange chromatogram is shown in FIG. PRO2.1. SDS-PAGE analysis of purified mono-[mPEG2-CAC-FMOC-40K-]-[PG-1] is shown in FIG. PRO2.2. RP-HPLC analysis of the purified conjugate is shown in FIG. PRO2.3, and MALDI-TOF analysis of the purified conjugate is shown in FIG. PRO2.4.

The purity of the mono-PEG-conjugate was >95% by SDS-PAGE and 100% by RP-HPLC analysis. The mass as determined by MALDI-TOF was within the expected range.

FIG. PRO2.1. Typical cation exchange purification profile of mono-[mPEG2-CAC-FMOC-40K]-[PG-1]. The mono-PEGylated conjugate, unreacted peptide and PEG are indicated. The blue line represents absorbance at 280 nm and the red line represents absorbance at 225 nm.

FIG. PRO2.2. SDS-PAGE (4-12% NuPage Bis-Tris, Invitrogen, with Coomassie Blue staining) of purified [mono]-[CAC-PEG2-FOMC-NHS-40K]-[Protegrin-1]. Lane 1, Mark12 MW markers; Lane 2, purified [mono]-[CAC-PEG2-FOMC-NHS-40K]-[Protegrin-1]. Lane 3, smaller quantity of purified [mono]-[CAC-PEG2-FOMC-NHS-40K]-[Protegrin-1]. The apparent large molecular weight of the conjugate, about 95 kDa, is due to a slow mobility of the monomeric conjugate in the gel due to a high degree of PEG hydration. Impurities were not detected in Lane 2.

FIG. PRO2.3. Purity analysis of [mono]-[CAC-PEG2-FOMC-40K]-[Protegrin-1] by Reversed Phase HPLC. The purity of the purified conjugate is 100% % at 280 nm. The peak at 4.5 minutes is a column-derived species and is not included in the sample.

FIG. PRO2.4. MALDI-TOF spectrum of purified mono-[CAC-PEG2-FMOC-40K]-[Protegrin-1]. The major peak at 43.1 kDa is within the expected range for the molecular weight of the mono-PEG-conjugate. The peak at 85.4 kDa may represent the single charged conjugate dimer formed during MALDI-TOF analysis.

Example PRO3

PEGylation of Protegrin-1 (PG-1) with N-m-PEG-Benzamide-p-Succinimidyl Carbonate (SBC)-30K

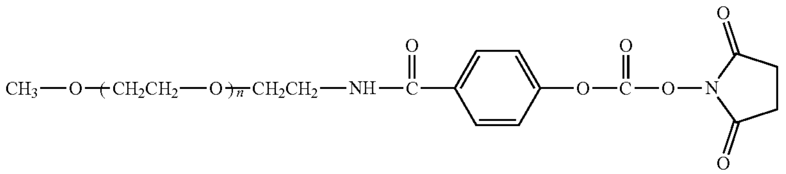

A stock solution of 1.2 mg/mL PG-1 was prepared in 2 mM HCl. To initiate a reaction, the PG-1 stock solution was brought to 25° C., a 15-fold molar excess of SBC-30K lyophilized powder was with stirring followed immediately with the addition of 1 M MES, pH 6, to give final concentrations of 1.0 mG/mL PG-1 (0.46 mM) and 50 mM MES. The reaction was allowed to proceed for 20 minutes at 25° C. After 20 min, the reaction was quenched with 100 mM glycine in 100 mM HCl (10 mM final glycine concentration) for 10 minutes. The reaction mixture was then diluted with deionized sterile water until the conductivity was below 1.0 mS/cm and the pH was adjusted to 4.0 with 1 M sodium acetate, pH 4.5 diluted.

The mono-PEGylated conjugate was purified from the reaction mixture by cation exchange chromatography using a column packed with SPHP media (GE Healthcare) on an AKTA Explorer 100 system (GE Healthcare). Buffer A was 20 mM sodium acetate, pH 4.0, Buffer B was 20 mM sodium acetate and 1 M NaCl pH 4.0. The AKTA Explorer plumbing system and SPHP column were sanitized with 1 M HCl and 1 M NaOH and the resin was equilibrated with 10 column volumes Buffer A prior to sample loading. After loading, the column was washed with 5 column volumes 100% A/0% B to remove un-reacted PEG reagent. PEGylated and nonPEGylated peptides were eluted using a linear gradient from 80% A/20% B to 0% A/100% B over 20 column volumes with a linear flow rate of 90 cm/hour.

Fractions collected during cation exchange chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 0% B and conjugate separation was achieved using the gradient timetable shown in Table PRO3.1.

| Step | Time (min) | % Mobile phase B |
| --- | --- | --- |
| 1 | 0.00 | 20.0 |
| 2 | 2.00 | 30.0 |

-continued

| Step | Time (min) | % Mobile phase B |
| --- | --- | --- |
| 3 | 5.00 | 45.0 |
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Fractions containing pure mono-[mPEG-SBC-30K]-[PG-1] as determined by RP-HPLC were pooled. Glacial acetic acid was added to the pooled fractions to a final concentration of 5% (v/v) and loaded onto a CG71S column (Rohm Haas) for Endotoxin removal and buffer exchange. Prior to sample loading, the column had been washed with 5% acetic acid in acetonitrile and equilibrated with 5% acetic acid in water (v/v). After sample loading, the column was washed with 10 column volumes of 5% acetic acid and mono-[mPEG-SBC-30K]-[PG-1] was eluted with a linear 0-100% gradient from 56 acetic acid to 5% acetic acid/95% Acetonitrile (v/v) over 10 column volumes. Fractions containing the conjugate as determined by analytical reversed phase HPLC, were pooled, lyophilized and stored at −80° C.

A typical cation exchange SP-HP chromatogram is shown in FIG. PRO3.1. SDS-PAGE analysis of purified mono-[mPEG-SBC-30K]-[PG-1] is shown in FIG. PRO3.2. RP-HPLC analysis of the purified conjugate is shown in FIG. PRO3.3, and MALDI-TOF analysis of the purified conjugate is shown in FIG. PRO3.4. The purity of the mono-PEG-conjugate was >95% by SDS-PAGE and 96.6% by RP-HPLC analysis. The mass as determined by MALDI-TOF was within the expected range.

FIG. PRO3.1 Typical cation exchange purification profile of mono-[mPEG-SBC-30K]-[PG-1]. The mono-PEGylated conjugate and unreacted PEG are indicated. The blue line represents absorbance at 280 nm and the red line represents absorbance at 225 nm.

FIG. PRO3.2. SDS-PAGE (4-12% NuPage Bis-Tris, Invitrogen, with Coomassie Blue staining) of purified [mono]-[mPEG-SBC-30K-]-[Protegrin-1]. Lane 1, Mark12 MW markers; Lane 2, purified [mono]-[mPEG-SBC-30K-]-[Protegrin-1]. The apparent large molecular weight of the conjugate, about 97 kDa, is due to a slow mobility of the monomeric conjugate in the gel due to a high degree of PEG hydration. Impurities were not detected in Lane 2.

FIG. PRO3.3. Purity analysis of [mono]-[mPEG-SBC-30K-]-[Protegrin-1] by reversed phase HPLC. The purity of the purified conjugate is 96.6% % at 280 nm. The peak with retention time at 15.3 min, is the SBC-30K PEG reagent and constitutes 3.4% of the sample. The peak at 4.5 minutes is a column-derived species and is not included in the sample FIG. PRO3.4. MALDI-TOF spectrum of purified [mono]-[mPEG-SBC-30K-]-[Protegrin-1]. The major peak at 33.3 kDa is within the expected range for the molecular weight of [mono]-[mPEG-SBC-30K-]-[Protegrin-1]. The peak at 66.1 kDa, may represent the singly charged conjugate dimer formed during MALDI-TOF analysis.

Example PRO4

PEGylation of Protegrin-1 (PG-1) with PEG-diButyrAldehyde-5K $OHCCH_2CH_2CH_2—(OCH_2CH_2)_4—NH—COO\text{-}PEG\text{-}O—CO—NH—(OCH_2CH_2)_4—CH_2CH_2CH_2—CHO$ Stock solutions of 8.0 mg/mL PG-1 and 200 mG/mL PEG-ButyAldehyde-5000 were prepared in 2 mM HCl. To initiate a reaction, the two stock solutions and a 1 M HEPES, pH 7.0, stock solution were brought to 25° C. and the three stock solutions were mixed (PEG reagent added last) to give final concentrations of 2.0 mg/mLPG-1, 50 mM HEPES and a 5-fold molar excess of PEG-diButyrAldehyde-5K over PG-1, After 15 minute reaction, a 20-fold molar excess of $NaBH_3CN$ over PEG was added and the reaction was allowed to continue for an additional 16 hours at 25° C. After 16 hr, 15 min total reaction time, the reaction was quenched with 100 mM glycine in 100 mM HCl (10 mM final glycine concentration) for 1 hour, after which glacial acetic acid was added to a final concentration of 5% (v/v).

The PEGylated conjugate was purified from the reaction mixture by reversed phase chromatography using a column packed with CG71S media (Rohm Haas) on an AKTA Explorer 100 system (GE Healthcare). Buffer A was 5% acetic acid/95% $H_2O$ (v/v), and Buffer B was 5% acetic acid/95% acetonitrile (v/v). The AKTA Explorer plumbing system and the CG71S column were sanitized with 1 M HCl and 1 M NaOH and the resin was equilibrated with 10 column volumes Buffer A prior to sample loading. After loading, the column was washed with 6 CV of 80% Buffer A/20% Buffer B and the PEGylated and nonPEGylated peptides were eluted using a linear gradient from 80% A/20% B to 0% A/100% B over 15 column volume with a linear flow rate of 90 cm/hour.

Fractions collected during CG71S reversed phase chromatography were analyzed using analytical reversed-phase HPLC. The mobile phases were: A, 0.1% TFA in water, and B, 0.05% TFA in acetonitrile. A Waters Symmetry C18 column (4.6 mm×75 mm) was used with a flow rate of 1.0 ml/min and a column temperature of 50° C. Detection was carried out at 280 nm. The column was equilibrated in 20% B and conjugate separation was achieved using the gradient timetable shown in Table PRO4.1.

| Step | Time (min) | % Mobile phase B |
|---|---|---|
| 1 | 0.00 | 20.0 |
| 2 | 2.00 | 30.0 |
| 3 | 5.00 | 45.0 |
| 4 | 6.00 | 45.0 |
| 5 | 18.00 | 80.0 |
| 6 | 18.10 | 100.0 |
| 7 | 20.10 | 100.0 |
| 8 | 20.20 | 10.0 |

Fractions containing pure [Protegrin-1]-[PEG-di-ButyrAldehyde-5K]-[Protegrin-1] as determined by RP-HPLC were pooled, lyophilized and stored at −80° C. A typical reverse phase CG71S chromatogram is shown in FIG. PRO4.1. SDS-PAGE analysis of purified [Protegrin-1]-[PEG-di-ButyAldehyde-5K]-[Protegrin-1] is shown in FIG. PRO4.2. RP-HPLC analysis of the purified conjugate is shown in FIG. PRO4.3, and MALDI-TOF analysis of the purified conjugate is shown in FIG. PRO4.4.

The purity of the [Protegrin-1]-[PEG-di-ButyrAldehyde-5K]-[Protegrin-1] conjugate was >95% by SDS-PAGE analysis and 98.7% by RP-HPLC analysis. The mass as determined by MALDI-TOF was within the expected range.

FIG. PRO4.1 Typical reversed phase purification profile of [Protegrin-1]-[PEG-di-ButyrAldehyde-5K]-[Protegrin-1]. The conjugate and unreacted peptide are indicated. The blue line represents absorbance at 280 nm.

FIG. PRO4.2. SDS-PAGE (12% NuPage Bis-Tris, Invitrogen, with Coomassie Blue staining) of purified [Protegrin-1]-[PEG-di-butyraldehyde-5K]-[Protegrin-1]. Lane 1, Mark12 MW markers; Lane 2, 17 uG of purified [Protegrin-1]-[PEG-di-butyraldehyde-5K]-[Protegrin-1], and Lane 3, 4 uG of purified [Protegrin-1]-[PEG-butyraldehyde-5K]-[Protegrin-]. The conjugate in Lane 2 migrates with a higher apparent molecular weight than the conjugate in Lane 3, which may be a result of conjugate oligomer formation at higher concentrations. Impurities were not detected (Lane 3).

FIG. PRO4.3. Purity analysis of [Protegrin-1]-[PEG-di-butyraldehyde-5K]-[Protegrin-11] by reversed phase HPLC. The purity of the purified conjugate is determined to be 98.7% at 280 nm. The peaks at 2.2 and 4.5 min are column or solvent derived species and are not included in the sample.

FIG. PRO4.4. MALDI-TOF spectrum of [Protegrin-1]-[PEG-di-butyraldehyde-5K]-[Protegrin-1]. The peak at 9.6 kDa is within the expected range for the molecular weight of the conjugate. The peak at 4.8 kDa may represent the molecular weight of the doubly charged conjugate, and the peak at 7.5 kDa may represent a conjugate containing a single peptide. The peaks at 2292 Da and 2147 Da are due to an instrument filter effect.

Example PRO5

Conjugation of Protegrin-1 with Dextran Tetra ethylene glycol-Butyraldehyde 40K

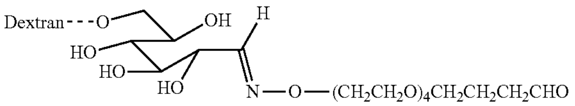

Stock solutions of 0.3 mg/mL protegrin-1 and 55 mg/mL dextran tetra ethylene glycol (TEG)-butyraldehyde 40K, both in 50 mM HEPES, pH 7.0, were prepared. To initiate a reaction, both stock solutions were brought to 25° C. and then mixed in equal volumes. The reaction mixture was stirred at 25° C. After 1 hour reaction, 100 μM sodium cyanoborohydride (final concentration) was added and the reaction was allowed to proceed for an additional 4 hours.

The dextran-protegrin-1 conjugate was purified from the reaction mixture by cation-exchange chromatography using CM Sepharose (GE Healthcare). Upon completion of the conjugation reaction, the reaction mixture was diluted 10-fold with water and loaded onto a column packed with CM Sepharose resin. Buffer A was 10 mM HEPES, pH 7, and buffer B was 10 mM HEPES, pH 7, 1M NaC. The resin was washed with buffer B and equilibrated with buffer A prior to sample loading. After loading, the column was washed with 2 column volumes buffer A. Conjugated and nonconjugated peptides were eluted in a linear gradient of 0-100% buffer B in 10 column volumes at a flow rate of 7 mL/min (FIG. 1).

FIG. PRO5.1. Typical cation-exchange chromatography profile of dextran-butryaldehyde-40K-protegrin-1. Fractions containing the conjugate are indicated in the box. The line represents absorbance at 280 nm.

Fractions containing dextran-butyraldehyde-40K-protegrin-1 were pooled, dialyzed against water, lyophilized and stored at −80° C.

FIG. PRO5.2. SDS-PAGE analysis (4-12% gel) of purified dextran-butryraldehyde-40K-protegrin-1. Dextran perturbs the gel migration of the dextran-peptide conjugate and the conjugate's band location is not indicative of its size. The marker (M) molecular weight unit is kDa.

Example PRO6

PEGylation of protegrin-1 with bi-functional mPEG-butaraldehyde-2K

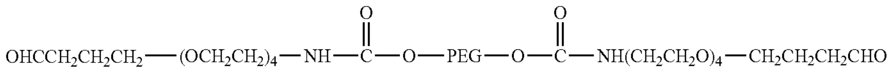

The conjugation reaction took place in an aqueous environment. 45.5 mg PG-1 was first dissolved into 9.1 mL PBS buffer to make a 5 mg/mL stock solution. 100 mg $(ALD)_2$2K was then dissolved into 1 mL PBS to make a 100 mg/mL stock solution. To initiate the conjugation, 0.867 mL $(ALD)_2$2K stock solution was slowly mixed into 9.7 mL PG-1 stock solution drop by drop under rapid stirring. 135 μl of 50 mg/mL sodium cyanoborohydride ($BaBH_3CN$) was added into the reaction mixture 30 min later to facilitate the stable secondary amine linkage formation through reductive amination. The $BaBH_3CN$ to $(ALD)_2$2K molar ratio was set at 5 with $BaBH_3CN$ in excess. The final net $(ALD)_2$2K (93% substitution) to PG-1 molar ratio was at 2 with $(ALD)_2$2K in excess. The formation of PG-1-ButyrALD-2K-PG-1 was confirmed by analytical RP-HPLC (Table PRO6.1).

TABLE PRO6.1

Analytical RP-HPLC method used to monitor PG-1-ButyrALD-2K-PG-1 production. Column: Waters Xbridge C18 5 μm 4.6 × 160 mm. Mobile Phase A: 0.1% TFA/$H_2O$ and B: 0.1% TFA/$CH_3CN$. Column temperature: 40° C. $UV_{280\ nm}$ was used to follow the elution.

| TIME (mm) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The (PG-1)-$(ALD)_2$2K-(PG-1) was purified by weak cation exchange chromatography using an AKTA Basic System. The reaction mixture was first diluted 5 fold with buffer A [20 mM acetate, pH 4.0] to reduce sample viscosity. The pH of the diluted sample was measured to be 4.0 and the conductivity to be 4.8 mS/cm. The diluted sample mixture was loaded onto a CM Sepharose FF column at 5 mL/min. After sample loading, the column was washed with 2CV 20% buffer B [20 mM acetate, 2 M NaCl, pH 4.0]. The loading and washing steps were done manually. The resin was washed until a flat $UV_{280nm}$ absorption line was observed. A linear gradient elution was applied next from 20% to 60% buffer B within 10 CV. The flow rate was held constant at 5 ml/min during the whole process. The chromatogram of the elution step is shown in FIG. PRO6.1.

FIG. PRO6.1: PG-1 and $(ALD)_2$2K conjugates purification with CM Sepharose FF resin. The $UV_{280nm}$ absorption curve is shown in blue and buffer B percentage is shown in green. The conductivity is shown in gray. Peak I contains mono-conjugate and peak 11 contains the desired di-conjugate.

The peak I and II fractions were analyzed by RP-HPLC (Table PRO6.1). The desired product was found in peak II.

Based on their high purities, peak II fractions 18 to 33 were pooled. The 210 mL purified (PG-1)-$(ALD)_2$2K-(PG-1) fraction pool was first centrifuged with a MWCO 10.000 Centricon to a final volume of 20 mL. The NaCl concentration was then lowered to less than 50 mM by dilution with 20 mM acetate, pH 4.0 buffer (final conductivity 3.8 mS/cm). The volume was reduced to less than 10 mL with a second centrifugation using a MWCO 10,000 Centricon.

The net peptide concentration in the concentrated (PG-1)-$(ALD)_2$2K-(PG-1) sample was measured to be 0.88 mg/mL by BCA. The conjugate's purity was determined at 96.2% by RP-HPLC. The number-average molecular weight was calculated to be 6888.2 Da by MALDI-TOF which is the expected mass of the di-conjugate. A final yield of 6.6 mg purified (PG-1)-$(ALD)_2$2K-(PG-1) was obtained.

FIG. PRO6.2: RP-HPLC analysis of (PG-1)-$(ALD)_2$2K-(PG-1).

FIG. PRO6.3: MALDI analysis of (PG-1)-$(ALD)_2$K-(PG-1). The 4753.6 Da peak might be the residual mono-conjugate contaminant. The 2136 Da peak represents the free peptide. The peak areas do not correspond to the relative amounts of the species in the sample.

Example PRO7

PEGylation of protegrin-1 with mPEG2-butaraldehyde-40K

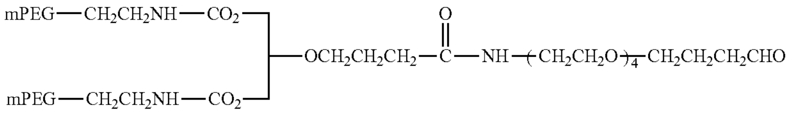

The conjugation reaction took place in an aqueous environment. 12 mg protegrin-1 (PG-1) was first dissolved into 1.2 mL PBS buffer to make a 10 mg/mL stock solution. 1500 mg ALD-40K was dissolved into 15 mL 2 mM HCl to make a 100 mg/mL stock solution. To initiate the conjugation, 11.4 mL ALD-40K stock solution was slowly mixed into 1.2 mL PG-1 stock solution drop by drop under rapid stirring. 360 μL of 50 mg/mL sodium cyanoborohydride ($BaBH_3CN$) was added into the reaction mixture immediately following PEG addition to facilitate the stable secondary amine linkage formation through reductive amination. The $BaBH_3CN$ to ALD-40K molar ration was 10 with $BaBH_3CN$ in excess. The net ALD-40K (99.5% purity) to PG-1 molar ratio was 5 with ALD-40K in excess. The reaction was allowed to proceed for 46 h at 22° C. for completion. The formation of ALD40K-PG-1 was confirmed by analytical RP-HPLC using the method described in Table PRO7.1.

TABLE PRO7.2

Analytical RP-HPLC method used to monitor ALD40K-PG-1 production. Column: Waters Xbridge C18 5 μm 4.6 × 160 mm. Mobile Phase A: 0.1% TFA/$H_2O$ and B: 0.1% TFA/$CH_3CN$. Column temperature: 40° C. $UV_{280\ nm}$ was used to follow the elution.

| TIME (min) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The ALD40K-PG-1 was purified by SP Sepharose HP resin using an AKTA Basic System. The reaction mixture was first diluted 5 fold with buffer A [20 mM MES, pH 6.0] to reduce sample viscosity. The pH of the diluted sample was measured to be 6.0 and the conductivity to be 5.2 mS/cm. The diluted sample mixture was loaded onto an SP Sepharose HP column at 5 mL/min. After sample loading, the column was washed with 100% buffer A. The column was then sequentially washed with a six step gradient (50, 100, 150, 200, 250 and 300 mM NaCl in 20 mM MES, pH 6.0 buffer]. Each wash step was controlled manually and was started only when the $UV_{280nm}$ absorbance was completely flat from the previous wash. The flow rate was constant at 5 ml/min during the whole process. The ALD40K-PG-1, peak II, was eluted at 300 mM NaCl. The chromatogram of the loading and elution is shown in FIG. PRO7.1.

FIG. PRO7.1.1 and 7.1.2: ALD40K-PG-1 purification with SP Sepharose HP resin. The $UV_{280nm}$ absorption curve is shown and buffer B percentage is shown. The conductivity is shown. The NaCl concentration in washing and eluting steps are labeled. The ALD40K-PG-1, peak II, was eluted at 300 mM NaCl.

The eluted peaks were analyzed by analytical RP-HPLC (Table PRO7.1) and SDS-PAGE (FIG. PRO7.2). The desired product, ALD40K-PG-1, was eluted in peak II. Based on their high purities, peak II fractions 18 to 33 were pooled.

The purified ALD40K-PG-1 pool was concentrated with a MWCO 10,000 Centricon. The final NaCl concentration was also lowered to 150 mM with 20 mM MES, pH 6.0 buffer dilution. SDS-PAGE of the purified and concentrated ALD40K-PG-1 is shown in FIG. PRO7.2. The net peptide concentration in the final ALD40K-PG-1 preparation was measured to be 0.8 mg/mL by BCA. The purity was determined at 96.2% by RP-HPLC (Table PRO7.1 and FIG. PRO7.3). The number-average molecular weight was calculated to be 41524 Da by MALDI-TOF, which corresponds to the expected mass of the conjugate (FIG. PRO7.4). A final yield of 7.6 mg purified ALD40K-PG-1 was obtained.

FIG. PRO7.3: RP-HPLC analysis of ALD40K-PG-1 (lot #YW-pgALD40K-01).

FIG. PRO7.4: MALDI analysis of ALD40K-PG-1 (lot #YW-pgALD40K-01). The ~85 KDa peak is believed to represent the ALD40K-PG-1 conjugate dimer formed as an artifact during MALDI analysis. The dimer is not detected by SDS-PAGE (Table 2).

Example PRO8

PEGylation of protegrin-1 with 4,7-CG-PEG2-FMOC-NHS-40K

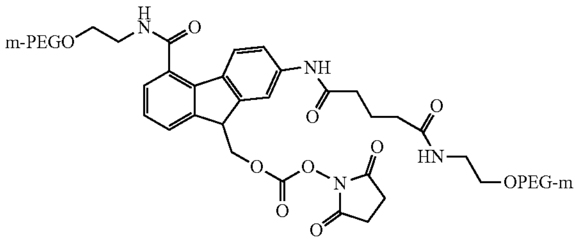

The conjugation reaction took place in an aqueous environment. 12 mg protegrin-1 (PG-1) was first dissolved into 1.2 mL PBS buffer to make a 10 mg/mL stock solution. 550 mg CG-40K was dissolved into 5.5 mL 2 mM HCl to make a 100 mg/mL stock solution. To initiate the conjugation, 5.0 mL CG-40K stock solution was slowly mixed into 1.2 mL PG-1 stock solution drop by drop under rapid stirring. 5.0 mL 10×PBS buffer was added into the reaction mixture to maintain a relatively neutral pH during the reaction (measured at 6.8). The net active CG-40K (95% purity, 77.8% substitution percentage) to PG-1 molar ratio was 1.7 with CG-40K in excess. The reaction was allowed to proceed for 330 min at 22° C. and 12 h at 4° C. for completion. The formation of CG40K-PG was confirmed by analytical RP-HPLC (Table 1).

TABLE PRO8.3

Analytical RP-HPLC method used to monitor CG40K-PG production. Column: Waters Xbridge C18 5 μm 4.6 × 160 mm. Mobile Phase A: 0.1% TFA/$H_2O$ and B: 0.1% TFA/$CH_3CN$. Column temperature: 40° C. $UV_{280\ nm}$ was used to follow the elution.

| TIME (min) | % Mobile phase B | Flow rate (mL/min) |
|---|---|---|
| 0.0 | 10 | 1.0 |
| 5 | 20 | 1.0 |
| 24 | 70 | 1.0 |
| 25 | 10 | 1.0 |

The CG40K-PG-1 was purified by SP Sepharose HP resin using an AKTA Basic System. The reaction mixture was first diluted 5 fold with buffer A [20 mM acetate, pH 4.0] to reduce sample viscosity. The diluted sample mixture was loaded onto an SP HP column at 5 mL/min. After sample loading, the column was washed with 100% buffer A until the $UV_{280nm}$ absorbance was flat. The conjugate was then eluted with a linear gradient of 0 to 80% buffer B [20 mM acetate, 1 M NaCl, pH 4.0] within 10 CV. The flow rate was constant at 5 ml/min during the whole process. The chromatogram of the loading and elution is shown in FIG. PRO8.1.

FIG. PRO8.1: CG40K-PG-1 purification with SP Sepharose HP resin. The $UV_{280nm}$ absorption curve is shown in blue and buffer B percentage is shown in green. The conductivity is shown in gray.

The CG40K-PG-1 fractions were analyzed by analytical RP-HPLC (Table PRO8.1). Based on their high purities, fractions 16 to 19 were pooled. The purified CG40K-PG-1 pool was concentrated with a MWCO 10,000 Centricon. The final NaCl concentration was also lowered to 150 mM with 20 mM acetate, pH 4.0 buffer dilution.

The net peptide concentration in the final CG40K-PG-1 preparation was measured to be 1.33 mg/mL by BCA. The purity was determined at 99.8% by RP-HPLC (Table PRO8.1 and FIG. PRO8.2). The number-average molecular weight was calculated to be 44033 Da by MALDI-TOF (FIG. PRO8.3). A final yield of 11.97 mg purified CG40K-PG-1 was obtained.

FIG. PRO8.2: RP-HPLC analysis of purified CG40K-PG-1. Analysis conditions are described in Table PRO8.1.

FIG. PRO8.3: MALDI-TOF analysis of purified CG40K-PG-1. The ~90 KDa peak is believed to represent the CG40K-PG-1 conjugate dimer formed as an artifact during MALDI analysis. The dimer is not detected by SDS-PAGE

Example PRO9

Hemolysis assay. Approximately 10 mL of blood was drawn from one adult rat into Na Heparin tube and kept in ice until use. Red blood cells were washed three times with 10 mL of cold DPBS ((−) $CaCl_2$ and (−) $MgCl_2$) and collected by sequential centrifugation at 3,000 g for 5 min at 4° C. Pellets of red blood cells were resuspended with DPBS ((−) $CaCl_2$ and (−) $MgCl_2$) and the total volume was brought up to initial volume of blood drawn. One mL of resuspended red blood cells was resuspended with 49 mL of DPBS ((−) $CaCl_2$ and (−) $MgCl_2$). Incubation mixture was prepared by 400 fold dilution of stock solution of test compounds with final volume of 800 μl. Final concentration of test compounds was equimolar to that of respective unconjugated compounds. Hemolysis incubation was done at 37° C. with mild agitation. For releasable conjugates, test compounds were preincubated in 1×PBS at 37° C. prior to hemolysis assay. Incubation mixture was centrifuged at 3,000 g for 5 min at 4° C., and the absorbance at 550 nm was read from supernatant. The percent of hemolysis was calculated relative to the 100% hemolysis produced by 0.25% Triton X-100.

| Compounds | Description | Note |
|---|---|---|
| PG1 | Protegrin 1 (PG1) | Samples were |
| CAC40K-40K-PG1 | PG1 conjugate with a releasable linker (release $t_{1/2}$ in 1XPBS at 37° C. = ~19.6 hr) | preincubated in 1XPBS at 37° C. prior to |
| CAC40K-fulvene | PEG moiety of CAC40K-PG1 | hemolysis assay. |
| PG1-ButyrALD-PG1 | PG1 conjugate with a stable linker | |
| Dextran-PG1 | PG1 conjugate with a stable linker | |
| 2 mM HCl | | Buffer control |
| Matrix control | | Matrix control |
| TritonX-100 | Detergent | Positive control |

For PG1, hemolytic effects were almost eliminated by PEG conjugation with a stable linker (PG1-ButyrALD-PG1, Dextran-PG1). (FIG. PRO9.1). Percent hemolysis of rat red blood cells by PG1 was comparable to literature data obtained from human red blood cell assay (FIG. PRO9.2). PG1-ButyrALD-5K-PG1 appeared to have little hemolytic activity. However, its hemolytic activity was significantly less than PG1. PG1 released from CAC-40K-PG1 exhibited hemolytic activity, however, hemolytic effects from CAC-40K-PG1 that had been preincubated for 96 hr (=5 times of its release $t_{1/2}$, ~19.6 hr) was 60-70% of that from PG1. This loss of activity appears to be mostly due to the degradation of PG1 during preincubation period since PG1 preincubated for 96 hr retained about 60% hemolytic activity compared to that from PG1 preincubated for 0 hr. PEG moiety itself (CAC40K-fulvene, mPEG2-NHS 20K-gly, and mPEG-SMB 30K-gly) did not cause hemolysis.

FIG. PRO9.1. Hemolysis relative to the 100% hemolysis produced by 0.25% Triton X-100.

FIG. PRO9.1. Hemolysis by PEG reagent controls.

FIG. PRO9.3. Hemolysis at the maximum concentration

FIG. PRO9.4. Hemolytic activities of PG-1: Human red blood cells were incubated with 0 to 100 μg/ml of PG-1 in PBS for 1 h at 37° C. (Tran D et al (2008) *Antimicrob. Agents Chemother* 52:944-953)

Example PRO10

Pharmacokinetic Studies of the Protegrin Conjugates

Twenty one (21) adult male Sprague-Dawley rats with indwelling jugular vein and carotid artery catheters (JVC/CAC) (Charles River Labs, Hollister, Calif.) were utilized for this study. The weight range of the animals was 313-346 grams. All animals were food fasted overnight. Prior to dosing the rats were weighed, the tails and cage cards were labeled for identification and the doses were calculated. Anesthesia was induced and maintained with 3.0-5.0% isoflurane. The JVC and CAC were externalized, flushed with HEP/saline (10 IU/mL HEP/mL saline), plugged, and labeled to identify the jugular vein and carotid artery The predose sample was collected from the JVC. When all of the animals had recovered from anesthesia and the predose samples were processed, the animals were dosed, intravenously (IV) via the JVC using a 1 mL syringe containing the appropriate test article, the dead volume of the catheter was flushed with 0.9% saline to ensure the animals received the correct dose.

Following a single IV dose, blood samples were collected at 0 (pre-dose collected as described above), 2, 10, 30, 60, 120, 240, 360 minutes for NKT-10503 (parent protegrin-1) group and 0 (pre-dose collected as described above), 2, 10, 30, 120, 240, 480, 1440 (24 hrs) minutes for the other groups via the carotid artery catheter and processed as stated in the protocol. Following the last collection point, the animals were euthanized. Bioanalytical analysis: analysis of the plasma samples was conducted using non-validated LC-MS/MS methods.

Pharmacokinetic Analyses:

Noncompartmental PK data analysis and report preparation was completed. PK analysis was performed using WinNonlin (Version 5.2, Mountain View, Calif.-94014). Concentrations in plasma that were below LLOQ were replaced with zeros prior to generating Tables and PK analysis. The following PK parameters were estimated using plasma concentration-time profile of each animal:

$C_0$ Extrapolated concentration to time "zero"

$C_{max}$ Maximum (peak) concentration $AUC_{all}$ Area under the concentration-time from zero to time of last concentration value $T_{1/2(Z)}$ Terminal elimination half-life $AUC_{inf}$ Area under the concentration-time from zero to time infinity $T_{max}$ Time to reach maximum or peak concentration following administration CL Total body clearance $V_z$ Volume of distribution based on terminal phase $V_{ss}$ Volume of distribution at steady state $MRT_{last}$ Mean residence time to last observable concentration Releasable-PEG:

FIG. PRO10.1 and PRO10.2 show the mean plasma concentration-time profiles for CG-$PEG_2$-FMOC-40K-PG-1 and CAC-$PEG_2$-FMOC-40K-PG-1, their corresponding PEG-metabolite and released Protegrin-1. FIG. PRO10.3 shows the released Protegrin-1 levels after the administration of the two releasable PEG constructs versus the level of Protegrin-1 given as native protein at the same dose (mg/kg).

Table PRO10.1 summarizes the PK parameters of protegrin-1 following equivalent protein mass of 1.6 mg/kg administered intravenously into rats via, CG-$PEG_2$-FMOC-40K-PG-1, CAC-$PEG_2$-FMOC-40K-PG-1 or native protegrin-1.

TABLE PRO10.1

Comparative PK Parameters of Protegrin-1 and PEG conjugates

| Test Compound | $C_{max}$ (ng/mL) | $T_{1/2}$ (hr) | $AUC_{INF}$ (ng · hr/mL) | $T_{max}$ (hr) | $MRT_{last}$ (hr) |
|---|---|---|---|---|---|
| Protegrin-1 | 2050 ± 601 | 0.35 ± 0.10 | 1160 ± 351 | 0.03 | 0.52 ± 0.05 |
| CAC-$PEG_2$-FMOC-40K-PG-1 | 222 ± 189 | 0.13* | 31.0* | 0.03 | 0.13 ± 0.02 |
| CG-$PEG_2$-FMOC-40K-PG-1 | 285 ± 30.0 | 1.95* | 655* | 0.03 | 2.53 ± 0.60 |

*n – 2

Non-Releasable-PEG:

FIG. PRO10.4 shows the mean plasma concentration-time profiles for NKT-10502, NKT-10519 and NKT-531 observed in this study. Table 2 summarizes the PK parameters of NKT-10502, NKT-10519 and NKT-531 following equivalent protein mass of 1.6 mg/kg administered intravenously into rats. Based on the observed data, NKT-10502 appeared to be declined slower than NKT-10519 and NKT-531.

TABLE PRO10.2

Comparative PK Parameters of Non-Releasable-PEG Protegrin-1 Conjugates Following Equivalent Protein Mass Intravenous Administration to Sprague Dawley rats (Mean ± SD)

| Test Compound | $C_{max}$ (ng/mL) | $T_{1/2}$ (hr) | $AUC_{INF}$ (ug · hr/mL) | $MRT_{last}$ (hr) | CL (mL/hr/kg) | $V_{ss}$ (mL/kg) |
|---|---|---|---|---|---|---|
| Protegrin-1 | 2050 ± 601 | 0.35 ± 0.10 | 1.16 ± 0.351 | 0.52 ± 0.05 | 1470 ± 434 | 848 ± 360 |
| m$PEG_2$-40K-PG-1 | 6110 ± 664 | 10.8 ± 3.0 | 52.7 ± 16.3 | 5.6 ± 0.83 | 32.9 ± 12.4 | 320 ± 131 |
| PG-1-PEG-2K-PG-1 | 6520 ± 679 | 7.3 ± 1.1 | 7.7 ± 1.09 | 1.7 ± 0.14 | 209 ± 27.3 | 432 ± 40.5 |
| PG-1-PEG-5K-PG-1 | 7550 ± 1680 | 6.8 ± 0.65 | 11.9 ± 0.866 | 1.6 ± 0.16 | 135 ± 9.22 | 248 ± 22.1 |

What is claimed is:

1. A conjugate of formula:

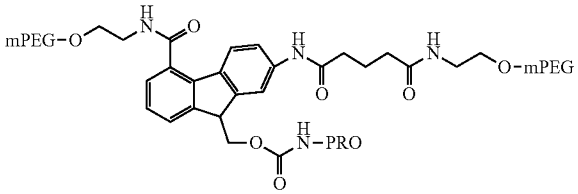

wherein PRO is a protegrin moiety having an amino acid sequence that is at least 90% identical to SEQ ID NO: 1 and each mPEG has a weight average molecular weight in a range of from about 500 Daltons to about 100,000 Daltons.

2. The conjugate of claim 1, wherein each mPEG has a weight-average molecular weight in a range of from about 500 Daltons to about 80,000 Daltons.

3. The conjugate of claim 1, wherein each mPEG has a weight-average molecular weight in a range of from about 2000 Daltons to about 50,000 Daltons.

4. The conjugate of claim 1, wherein each mPEG has a weight-average molecular weight in a range of from about 5000 Daltons to about 40,000 Daltons.

5. A pharmaceutical composition comprising a conjugate of claim 1 and a pharmaceutically acceptable excipient.

6. The conjugate of claim 1, wherein the protegrin moiety has an amino acid sequence that is at least 95% identical to SEQ ID NO: 1.

7. The conjugate of claim 1, wherein the protegrin moiety has the amino acid sequence of SEQ ID NO: 1.

8. A method for making a conjugate of claim 1 comprising contacting, under conjugation conditions, a protegrin moiety with a polymeric reagent bearing a functional group.

9. A method of treatment of a microbial infection comprising administering a conjugate of claim 1 to a subject in need thereof.

* * * * *